(12) United States Patent
Sadée et al.

(10) Patent No.: US 9,061,024 B2
(45) Date of Patent: *Jun. 23, 2015

(54) COMBINATION ANALGESIC EMPLOYING OPIOID AGONIST AND NEUTRAL ANTAGONIST

(71) Applicant: AIKO Biotechnology, Portland, ME (US)

(72) Inventors: Wolfgang Sadée, Upper Arlington, OH (US); Edward Bilsky, Biddeford, ME (US); Janet Yancey-Wrona, Freeport, ME (US)

(73) Assignee: AIKO Biotechnology, Portland, ME (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/278,576

(22) Filed: May 15, 2014

(65) Prior Publication Data

US 2014/0336212 A1    Nov. 13, 2014

Related U.S. Application Data

(63) Continuation of application No. 13/687,683, filed on Nov. 28, 2012, now Pat. No. 8,748,448, which is a continuation-in-part of application No. 12/288,347, filed on Oct. 17, 2008, now Pat. No. 8,883,817.

(60) Provisional application No. 60/981,034, filed on Oct. 18, 2007.

(51) Int. Cl.
*A61K 31/485* (2006.01)
*A61K 31/137* (2006.01)
*A61K 45/06* (2006.01)

(52) U.S. Cl.
CPC ............. *A61K 31/485* (2013.01); *A61K 31/137* (2013.01); *A61K 45/06* (2013.01)

(58) Field of Classification Search
USPC ........................................................ 514/282
See application file for complete search history.

(56) References Cited

U.S. PATENT DOCUMENTS

| | | | |
|---|---|---|---|
| 3,523,906 A | 8/1970 | Vrancken et al. | 252/316 |
| 3,691,090 A | 9/1972 | Kitajima et al. | 252/316 |
| 3,737,337 A | 6/1973 | Schnoring et al. | 117/100 |
| 3,891,570 A | 6/1975 | Fukushima et al. | 252/316 |
| 3,960,757 A | 6/1976 | Morishita et al. | 252/316 |
| 4,175,119 A | 11/1979 | Porter | 424/10 |
| 4,176,186 A | 11/1979 | Goldberg et al. | 424/260 |
| 4,389,330 A | 6/1983 | Tice et al. | 427/213.36 |
| 4,457,933 A | 7/1984 | Gordon et al. | 424/260 |
| 4,459,278 A | 7/1984 | Porter | 424/10 |
| 4,719,215 A | 1/1988 | Goldberg | 514/282 |
| 4,760,069 A | 7/1988 | Rzeszotarski et al. | 514/282 |
| 4,769,372 A | 9/1988 | Kreek | 514/282 |
| 4,861,781 A | 8/1989 | Goldberg | 514/282 |
| 5,019,400 A | 5/1991 | Gombotz et al. | 424/497 |
| 5,472,943 A | 12/1995 | Crain et al. | 514/12 |
| 5,512,578 A | 4/1996 | Crain et al. | 514/282 |
| 5,580,876 A | 12/1996 | Crain et al. | 514/282 |
| 5,650,173 A | 7/1997 | Ramstack et al. | 424/489 |
| 5,656,297 A | 8/1997 | Bernstein et al. | 424/484 |
| 5,767,125 A | 6/1998 | Crain et al. | 514/282 |
| 5,780,479 A | 7/1998 | Kim | 514/282 |
| 5,792,477 A | 8/1998 | Rickey et al. | 424/501 |
| 5,811,451 A | 9/1998 | Minoia et al. | 514/443 |
| 5,852,032 A | 12/1998 | Mason | 514/282 |
| 5,916,598 A | 6/1999 | Rickey et al. | 424/501 |
| 5,922,253 A | 7/1999 | Herbert et al. | 264/5 |
| 5,972,954 A | 10/1999 | Foss et al. | 514/282 |
| 6,004,970 A | 12/1999 | O'Malley et al. | 514/282 |
| 6,054,127 A | 4/2000 | Swain et al. | 424/194.1 |
| 6,110,503 A | 8/2000 | Rickey et al. | 424/501 |
| 6,136,817 A | 10/2000 | Schmidhammer | 514/279 |
| 6,194,006 B1 | 2/2001 | Lyons et al. | 424/489 |
| 6,228,863 B1 | 5/2001 | Palermo et al. | 514/282 |
| 6,271,240 B1 | 8/2001 | Simon | 514/282 |
| 6,274,591 B1 | 8/2001 | Foss et al. | 514/282 |
| 6,277,384 B1 | 8/2001 | Kaiko et al. | 424/400 |

(Continued)

FOREIGN PATENT DOCUMENTS

| | | | | |
|---|---|---|---|---|
| EP | 1 479 381 A1 | 11/2004 | | A61K 9/20 |
| EP | 1 263 438 B1 | 5/2006 | | A61K 31/485 |

(Continued)

OTHER PUBLICATIONS

Bilsky et al., "Antinociceptive activity of [beta-methyl-2', 6'-dimethyltyrosine(1)]-substituted cyclic [D-Pen(2), D-Pen(5)]Enkephalin and [D-Ala(2), Asp(4)]Deltorphin analogs," *J. Pharmacol. Exp. Ther.*, vol. 293, No. 1, pp. 151-158 (Apr. 2000).

Brewer et al., "Naltrexone: report of lack of hepatotoxicity in acute viral hepatitis, with a review of the literature," *Addict Bio.*, vol. 9, No. 1, pp. 81-87 (Mar. 2004).

Chatterjie et al., "Stereospecific synthesis of the 6β-Hydroxy Metabolites of Naltrexone and Naloxone," *J. Med. Chem.*, vol. 18, pp. 490-492 (May 1975).

Cone et al., "The Urinary Excretion Profile of Naltrexone and Metabolites in Man," *Drug Metab. Dispos.*, vol. 2, No. 6, pp. 506-512 (Nov. 1974).

Dunbar et al., "Single- and Multiple-Dose Pharmacokinetics of Long-acting Injectable Naltrexone," *Alcohol: Clin. Exp. Res.*, vol. 30, No. 3, pp. 480-490 (Mar. 2006).

(Continued)

*Primary Examiner* — Shirley V Gembeh

(74) *Attorney, Agent, or Firm* — Sunstein Kann Murphy & Timbers LLP

(57) ABSTRACT

In some embodiments, the invention provides a non-addictive analgesic co-formulation comprising an opioid agonist in an amount sufficient to confer analgesia in a mammalian subject (such as a human) and a neutral opioid antagonist in an amount sufficient to inhibit peripheral effects of the opioid agonist, and insufficient to block substantial central effects of the opioid agonist in the subject. The formulation may be formulated for oral administration to the subject. Such formulations, and methods of using the same, may also deter diversion, inhibit peripheral effects of the opioid agonist, and reduce addiction liability.

14 Claims, 35 Drawing Sheets

(56) References Cited

U.S. PATENT DOCUMENTS

| | | | |
|---|---|---|---|
| 6,306,425 B1 | 10/2001 | Tice et al. | 424/426 |
| 6,362,194 B1 | 3/2002 | Crain et al. | 514/285 |
| 6,375,957 B1 | 4/2002 | Kaiko et al. | 424/400 |
| 6,419,959 B1 | 7/2002 | Walter et al. | 424/490 |
| 6,451,806 B2 | 9/2002 | Farrar | 514/282 |
| 6,455,537 B1 | 9/2002 | Cooper | 514/289 |
| 6,469,030 B2 | 10/2002 | Farrar et al. | 514/331 |
| 6,475,494 B2 | 11/2002 | Kaiko et al. | 424/400 |
| 6,525,062 B2 | 2/2003 | Levine | 514/282 |
| 6,528,271 B1 | 3/2003 | Bohn et al. | 435/7.2 |
| 6,559,158 B1 | 5/2003 | Foss et al. | 514/282 |
| 6,559,159 B2 | 5/2003 | Carroll et al. | 514/282 |
| 6,569,866 B2 | 5/2003 | Simon | 514/282 |
| 6,593,367 B1 | 7/2003 | Dewey et al. | 514/561 |
| 6,608,075 B2 | 8/2003 | Foss et al. | 514/282 |
| 6,627,635 B2 | 9/2003 | Palermo et al. | 514/282 |
| 6,696,066 B2 | 2/2004 | Kaiko et al. | 424/400 |
| 6,713,488 B2 | 3/2004 | Sadée et al. | 514/282 |
| 6,716,449 B2 | 4/2004 | Oshlack et al. | 424/449 |
| 6,734,188 B1 | 5/2004 | Rhodes et al. | 514/282 |
| 6,790,854 B2 | 9/2004 | Tsushima et al. | 514/278 |
| 6,794,510 B2 | 9/2004 | Le Bourdonnec et al. | 546/192 |
| 6,825,205 B2 | 11/2004 | Kyle | 514/282 |
| 6,919,350 B2 | 7/2005 | Chang et al. | 514/282 |
| 6,992,090 B2 | 1/2006 | Le Bourdonnec et al. | 514/317 |
| 7,008,939 B2 | 3/2006 | Christoph | 514/212.01 |
| 7,026,329 B2 | 4/2006 | Crain et al. | 514/285 |
| 7,034,036 B2 | 4/2006 | Schoenhard | 514/282 |
| 7,041,320 B1 | 5/2006 | Nuwayser | 424/497 |
| 7,056,500 B2 | 6/2006 | Bentley et al. | 424/78.18 |
| 7,091,354 B2 | 8/2006 | Le Bourdonnec et al. | 546/236 |
| 7,144,587 B2 | 12/2006 | Oshlack et al. | 424/490 |
| 7,172,767 B2 | 2/2007 | Kaiko et al. | 424/468 |
| 7,196,100 B2 | 3/2007 | Benesh et al. | 514/318 |
| 7,201,920 B2 | 4/2007 | Kumar et al. | 424/454 |
| 8,748,448 B2 | 6/2014 | Sadée et al. | 514/282 |
| 8,883,817 B2 | 11/2014 | Sadée et al. | 514/282 |
| 2001/0049375 A1 | 12/2001 | Sadee et al. | 514/282 |
| 2003/0068392 A1 | 4/2003 | Sackler | 424/760 |
| 2003/0187010 A1 | 10/2003 | Foss et al. | 514/282 |
| 2003/0191147 A1 | 10/2003 | Sherman et al. | 514/282 |
| 2003/0211157 A1 | 11/2003 | Simon | 424/486 |
| 2004/0024006 A1 | 2/2004 | Simon | 514/282 |
| 2004/0162308 A1 | 8/2004 | Foss et al. | 514/282 |
| 2004/0167147 A1 | 8/2004 | Foss et al. | 514/282 |
| 2004/0167148 A1 | 8/2004 | Foss et al. | 514/282 |
| 2004/0180916 A1 | 9/2004 | Levine | 514/282 |
| 2004/0254208 A1 | 12/2004 | Weber et al. | 514/282 |
| 2005/0038062 A1 | 2/2005 | Burns et al. | 514/282 |
| 2005/0165038 A1 | 7/2005 | Gordon | 514/282 |
| 2006/0069086 A1 | 3/2006 | Michalow | 514/220 |
| 2006/0111382 A1 | 5/2006 | Shafer et al. | 514/282 |
| 2006/0235038 A1 | 10/2006 | Simon | 514/282 |
| 2007/0099947 A1 | 5/2007 | Dean, III et al. | 514/282 |
| 2007/0105863 A1 | 5/2007 | Dolle et al. | 514/249 |
| 2007/0197573 A1 | 8/2007 | Sadee et al. | 514/282 |
| 2009/0111844 A1 | 4/2009 | Sadee et al. | 514/282 |

FOREIGN PATENT DOCUMENTS

| | | | | |
|---|---|---|---|---|
| EP | 2 214 672 | | 8/2010 | A61K 31/485 |
| WO | WO 96/37775 A1 | | 11/1996 | G01N 33/53 |
| WO | WO 01/68080 A2 | | 9/2001 | A61K 31/00 |
| WO | WO 2004/050020 A2 | | 6/2004 | |
| WO | WO 2007/016108 A1 | | 2/2007 | A61K 45/06 |
| WO | WO 2009/051824 | | 4/2009 | A61K 31/485 |

OTHER PUBLICATIONS

Ferari et al., "Serum time course of naltrexone and 6β-naltrexol levels during long term treatment in drug addicts," *Drug Alcohol Depend.*, vol. 52, No. 3, pp. 211-220 (Nov. 1998).

Kiptoo et al., European Journal of Pharmaceutical Sciences 33 (2008), 371-379.

Ko et al., "Differential in Vivo Potencies of Naltrexone and 6β-Naltrexol in the Monkey," *J. Pharmacol. Exp. Therp.*, vol. 316, No. 2, pp. 772-779 (Feb. 2006).

Jayaram-Lindstrom et al., "An open clinical trial of naltrexone for amphetamine dependence: compliance and tolerability," *Nord. J. Pschy.*, vol. 59, No. 3, pp. 167-171 (2005).

Jiang et al., "Stereochemical studies on medicinal agents. 23. Synthesis and biological evaluation of 6-amino derivatives of naloxone and naltrexone," *J. Med. Chem.*, vol. 20, No. 8, pp. 1100-1102 (Aug. 1977).

Marczak et al., "[$N$-Allyl-Dmt$^1$]-Endomorphins Are μ-Opioid Receptor Antagonists Lacking Inverse Agonist Properties," *J. Pharmacol. Exp. Ther.*, vol. 323, pp. 374-380 (Jul. 2007).

Perez-Reyes et al., "A comparative study of the oral, intravenous, and subcutaneous administration of 3H-naltrexone to normal male volunteers," *NIDA Res. Mono.*, vol. 28, pp. 93-101 (1981).

Plapp, "Control of Alcholo Metabolism," *Towards a Molecular Basis of Alcohol Use and Abuse*, pp. 311-322 (1994).

Raehal et al., "In vivo characterization of 6β-naltrexol, an opioid ligand with less inverse agonist activity compared with naltrexone and naloxone in opioid-dependent mice," *J. Pharmacol. Exp. Ther.*, vol. 313, No. 3, pp. 1150-1162 (Jun. 2005).

Sadée et al., "Basal Opioid Receptor Activity, Neutral Antagonists, and Therapeutic Opportunities," *Life Sci.*, vol. 76, No. 13, pp. 1427-1437 (Feb. 2005).

Sayre et al., "Importance of C-6 chirality in conferring irreversible opioid antagonism to naltrexone-derived affinity labels," *J. Med. Chem.*, vol. 26, No. 9, Abstract Only, 2 pages (Sep. 1983).

Shoblock et al., "Constitutively Active Mu Opioid Receptors Mediate the Enhanced Conditioned Aversive Effect of Naloxone in Morphine-Dependent Mice," *Neuropsychopharmacology*, vol. 31, pp. 171-177 (2006).

Verebey, "The Clinical Pharmacology of Naltrexone: Pharmacology and Pharmacodynamics," *NIDA Res. Monogr.*, vol. 28, pp. 147-158 (1981).

Walker et al., J. Palliative Medicine 11 (80, 2008) 1103-1108.

Wall et al., "The Metabolism of Naltrexone in Man," *NIDA Res. Monogr.*, vol. 28, pp. 105-131 (1981).

Wall et al., "Metabolism and Disposition of Naltrexone in Man after Oral and Intravenous Administration," *Drug Metab. Dispos.*, vol. 9, No. 4, pp. 369-375 (Aug. 1981).

Wang et al., "Inverse Agonists and Neutral Antagonists at mu Opioid Receptor (MOR): Possible Role of Basal Receptor Signaling in Narcotic Dependence," *J. Neurochem.*, vol. 77, No. 6, pp. 1590-1600 (Jun. 2001).

Wang et al., "Basal signaling activity of mu opioid receptor in mouse brain: role in narcotic dependence," *J Pharmacol. Exp. Ther.*; vol. 308, No. 2, pp. 512-520 (Feb. 2004).

Yancey-Wrona et al., "6β-Naltrexol Prefrentially Antagonizes Opioid Effects on Gastrointestinal Transit Compared to Antinociception in Mice", *Life Sci.*, vol. 85, Nos. 11-12, pp. 413-420 (Sep. 2009).

ClinicalTrials.gov, "A Phase 2, Double-Blind, Multiple-Dose Escalation Study to Evaluate NKTR-118 (Oral PEG-Naloxol) in Patients with Opioid-Induced Constipation (OIC)," www.clinicaltrials.gov, 3 pages (Sep. 2009).

www.drugs.com, ReVia™ Label.

European Patent Office Jeans Ambrosch, Authorized Officer, Partial International Search Report—Application No. PCT/US2008/011915; dated Jun. 10, 2009 (17 pages).

European Patent Office Haider, Ursula, Authorized Officer, The International Search Report and the Written Opinion of the International Searching Authority—Application No. PCT/US2008/011915, dated Sep. 30, 2009 (34 pages).

European Patent Office Giffo-Schmitt, Beate, Authorized Officer, The International Preliminary Report on Patentability—Application No. PCT/US2008/011915, dated Apr. 20, 2010 (16 pages).

European Patent Office, Summons to Attend Oral Proceedings, pursuant to Rule 115(1) EPC—International Application No. 08839342.6, dated Jan. 5, 2012 (16 pages).

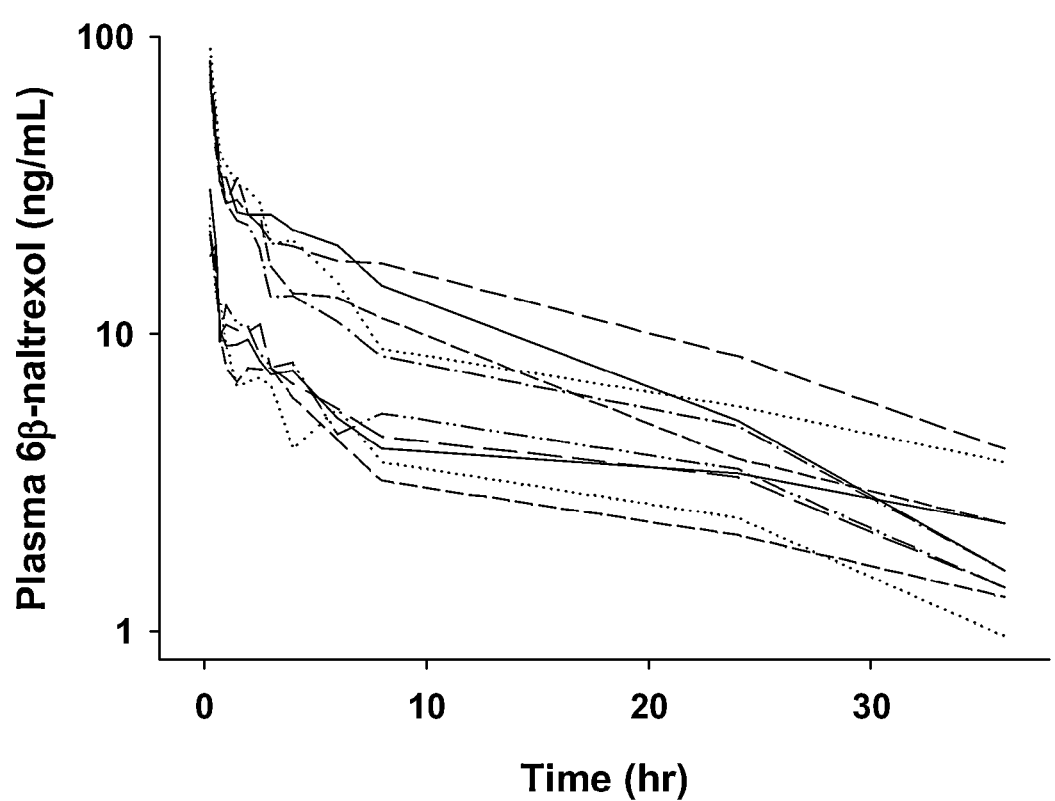
Figure 18. 6β-Naltrexol Plasma Pharmacokinetics.

Simulated Plasma Concentrations for
Oral Immediate Release Oxycodone/AIKO-150 (20/15 mg)
Fig. 19A
Fig. 19B
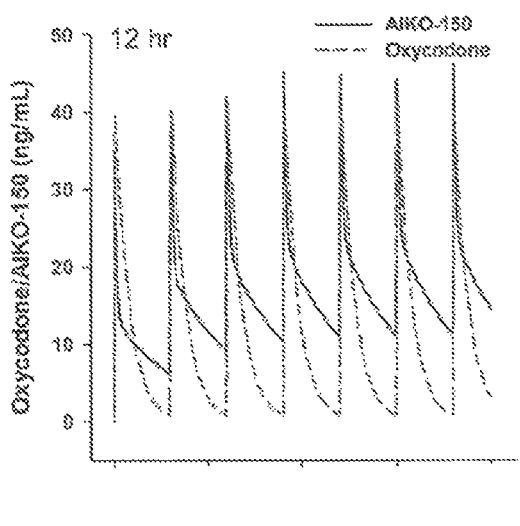
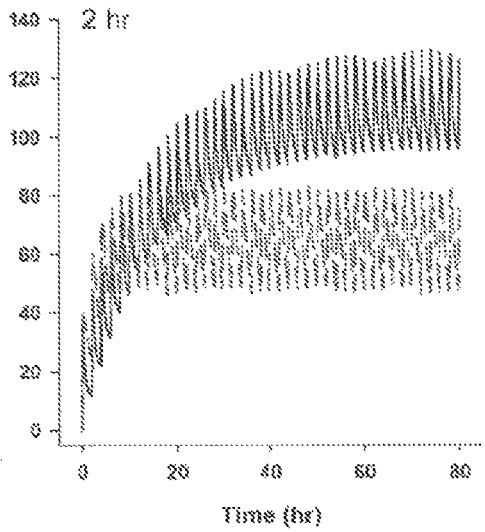
Fig. 19C
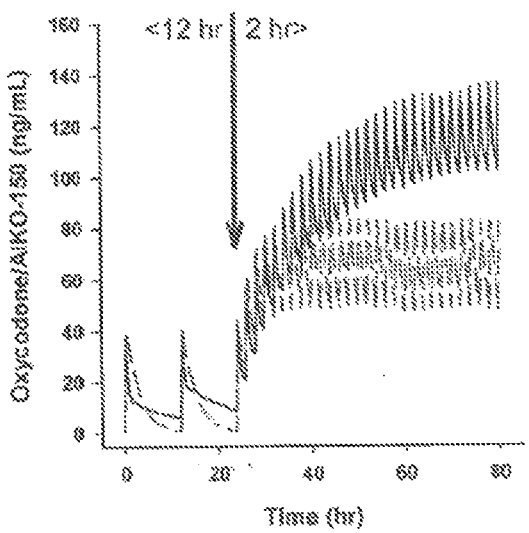
Figures 19A-19C. Combined immediate release oxycodone and 6 β-naltrexol.

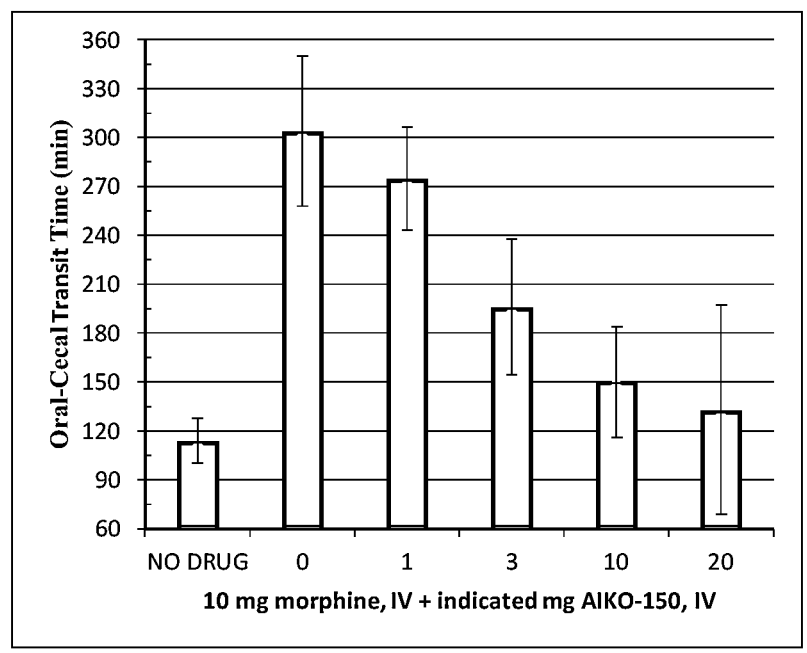
Figure 20. Oral-Cecal Transit Time Measured in Group 2 Subjects.

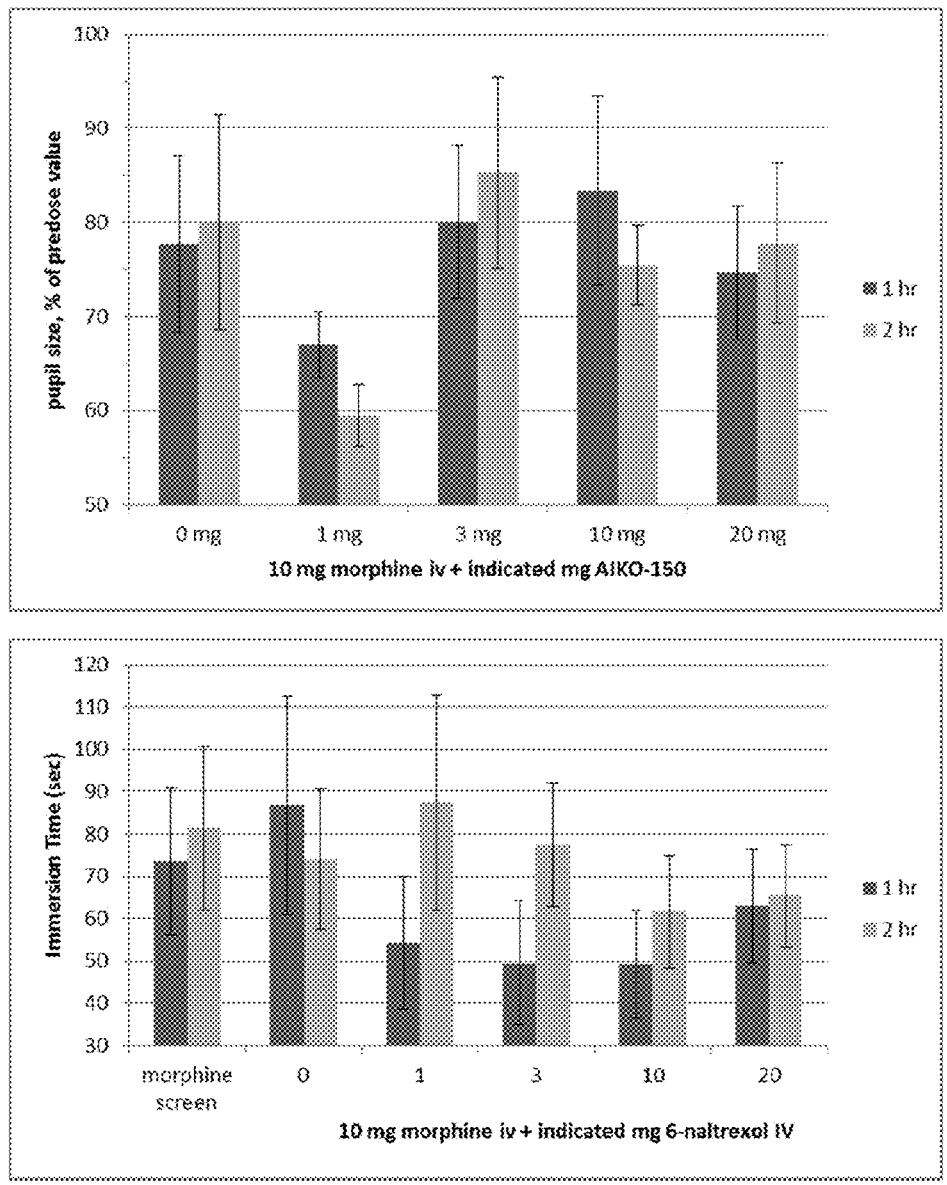
Figures 21A and 21B. Effect of 6β-Naltrexol on Opioid-Induced Pupil Constriction (Fig. 21A, upper panel) and Analgesia (Fig. 21B, lower panel).

COMBINATION ANALGESIC EMPLOYING OPIOID AGONIST AND NEUTRAL ANTAGONIST

CROSS REFERENCE TO RELATED APPLICATIONS

This application is a continuation of U.S. patent application Ser. No. 13/687,683 filed Nov. 28, 2012 (now U.S. Pat. No. 8,748,448), which is itself a continuation-in-part of U.S. application Ser. No. 12/288,347, filed Oct. 17, 2008, which itself claims priority from U.S. Provisional Application Ser. No. 60/981,034, filed Oct. 18, 2007, all of which are hereby incorporated by reference in their entireties.

TECHNICAL FIELD

The present invention relates to co-formulations of opioid agonists and opioid antagonists, and in particular to such co-formulations using neutral antagonists.

BACKGROUND ART

Opioid analgesics still rank as the most frequently prescribed drugs, with no broadly applicable alternative presently available. Opioid agonists, while creating analgesia in humans and other mammalian subjects, also have side effects. For example, opioid agonists are typically addictive, which can lead to widespread abuse, particularly for orally administered opioid analgesics such as oxycodone and hydromorphone. Addiction is characterized by tolerance, dependence, and drug craving. Another critical set of adverse effects includes respiratory depression (mostly CNS mediated), nausea, intestinal dysfunction, constipation, pruritus, bone loss, immune dysfunction, and more. The co-formulation—the subject of the present disclosure—seeks to reduce both addiction liability and peripheral adverse effects (e.g., constipation), requiring a unique set of required pharmacokinetic/pharmacological properties of the antagonist: neutral antagonist to avoid severe withdrawal, oral bioavailability, reduced access to the CNS, and a longer half-life than the agonist. In addition, oral bioavailability of the antagonist into the peripheral circulation is essential for reaching peripheral opioid receptors not residing in the gastrointestinal tract, affecting pruritus, bone loss, immune dysfunction, and more. Without considering all these qualities together, a co-formulation cannot be successful, or will at best be partially successful.

To address the addictive qualities of opioid agonists, the prior art teaches the use of co-formulations that include both opioid agonists and opioid antagonists. Most prior art co-formulations utilize opioid antagonists such as naltrexone or naloxone, which themselves have aversive effects in human and mammalian subjects. In fact, these compounds can trigger severe, and sometimes life-threatening, withdrawal symptoms. Such opioid antagonists are referred to in the present application as "aversive." In addition, natrexone does not show peripheral selectivity, entering the brain with ease while naloxone has a very short half-life and poor bioavailability, characteristics that also disqualify these antagonists and their congener for the intended formulation. U.S. Pat. No. 6,627,635 to Palermo et al. and U.S. Pat. Nos. 6,696,066, 6,475,494 and U.S. Pat. No. 6,375,957 to Kaiko et al. provide examples of co-formulations that employ aversive opioid antagonists. Recent research by Marczak et al. emphasizes the aversive effects of both naltrexone and naloxone in opioid-dependent subjects. Marczak E., Jinsmaa Y., Li T., Bryant S. D., Tsuda Y., Okada Y., Lazaraus L. H. (Jul. 12, 2007) "[N-Allyl-Dmt1]-endomorphins are µ-opioid receptor antagonists lacking inverse agonist properties," J. Pharmacol. Exp. Ther. Fast Forward.

U.S. Pat. No. 6,713,488 B2 to Wolfgang Sadée et al., which is hereby incorporated herein by reference and is hereinafter referred to as "Sadée," teaches the use of "neutral" opioid antagonists, which do not have aversive effects, to treat opioid agonist addiction. Sadée identifies as neutral antagonists certain naltrexone and naloxone analogs, including 6β-naltrexol and 6β-naltrexamide. Sadée also teaches that neutral antagonists can be used to treat other side-effects of opioid agonists, including constipation and respiratory depression.

Building on Sadée's research, United States Patent Application 2004/0024006 A1 to David Lew Simon, hereinafter referred to as "Simon," proposes non-addictive opioid agonist/antagonist co-formulations that include primarily the aversive antagonist naltrexone while also incorporating neutral opioid antagonists such as 6β-naltrexol. Simon's disclosure is prophetic in nature, however, and lacks supporting, experimental data. Simon does not disclose anything about bioavailability of naltrexol. Certainly, the results described herein of the considerable selectivity of naltrexol in inhibiting the peripheral effects of an opioid agonist as compared to the central effects of that opioid agonist (hence, naltrexol has "peripheral selectivity") are nowhere described in Simon. This lack of insight in Simon blocks the development of the co-formulation proposed here. For example, paragraphs [0107] and [0108] of Simon discuss a known effective dosage of morphine (0.15 mg/kg body weight) and then suggest a completely unknown and untested range of possible doses for 6β-naltrexol from 0.00026-0.0015 mg/kg body weight, providing no data for such a formulation ever being effective. Similarly, in paragraph [0155] of Simon's application, Simon uses data provided by Kaiko for naltrexone (not naltrexol) in the U.S. Pat. No. 6,475,494 to propose that 0.5 to 12 mg of 6β-naltrexol be administered per 15 mg hydrocodone. These ratios of naltrexol to opioid range from 0.03:1 (i.e. 15.5-fold less naltrexol than opioid) to nearly a 1:1 ratio of naltrexol to opioid. Given the complete lack of supporting data, these two suggested dosage ranges spanning several orders of magnitude are uninformative and effectively meaningless, representing mere guesses. Further, Kaiko teaches the use of antagonists that have aversive effects in humans and precipitate severe withdrawal symptoms, lacking peripheral selectivity. Simon extrapolates to propose a dosage chart in paragraph [0156] for other kinds of opioid agonists, but also fails to consider the critical antagonist dosages needed to treat peripheral opioid adverse effects while providing no guidance on treating effectively addiction liability, which is CNS related. None of the prior art considers the dual peripheral and central effects of the co-formulation proposed here, requiring a unique set of properties.

SUMMARY OF THE INVENTION

The present invention teaches the use of an opioid agonist/neutral opioid antagonist co-formulation, co-administration of the agonist with the antagonist, or separate but overlapping administration of the agonist with the neutral antagonist, wherein such co-formulation, co-administration or separate administration is uniquely designed to address both addiction liability of the opioid and peripheral side effects, such as constipation.

In some embodiments, the invention provides unit dosage of an analgesic composition comprising, consisting essentially of, or consisting of: an opioid agonist in a first amount sufficient to confer analgesia in a subject; a neutral opioid antagonist in a second amount sufficient to substantially inhibit peripheral effects and insufficient to block substantial central effects of the agonist in the subject, wherein a weight/weight (w/w) ratio of the first amount to the second amount is at least 1:1 and the opioid antagonist is selected to have a blood half-life that is substantially longer than the blood half-life of the opioid agonist, so as to deter abuse resulting from overly frequent administration of the unit dosage; and a pharmaceutically acceptable carrier. In some embodiments, the w/w ratio of the first amount to the second amount is at least 2:1, or at least 3:1 or at least 5:1 or at least 7.5 to 1 or at least 10:1, or at least 15:1, or at least 20:1.

In some embodiments, the unit dosage is formulated for oral administration to a subject. In some embodiments, the unit dosage is formulated for transdermal administration to a subject, or for parenteral administration (e.g., subcutaneous injection, intravenous injection, etc.) to a subject. In some embodiments, the subject is a mammalian subject. In some embodiments, the subject is a human subject. In some embodiments, the subject is a domesticated animal (e.g., cat, dog, horse, cow, goat, sheep, bird, or reptile).

In some embodiments, the agonist is morphine. In some embodiments, the morphine is administered orally and the first amount is 10 mg to a 70 kg subject.

In some embodiments, the agonist is not morphine. In some embodiments where the agonist is not morphine, the first amount is a morphine equivalent amount, said morphine equivalent amount corresponding to 10 mg morphine administered orally to a 70 kg subject.

In some embodiments, the antagonist is 6β-naltrexol. In some embodiments, the 6β-naltrexol is administered orally and the second amount is 1.5 mg to 5 mg 6β-naltrexol to a 70 kg subject. In some embodiments, the 6β-naltrexol is administered orally and the second amount is 1.5 mg to 10 mg 6β-naltrexol to a 70 kg subject.

In some embodiments, the antagonist is not 6β-naltrexol. In some embodiments where the antagonist is not 6β-naltrexol, the second amount is a 6β-naltrexol equivalent amount, said 6β-naltrexol equivalent amount corresponding to 1.5 mg to 5 mg 6β-naltrexol administered orally to a 70 kg subject. In some embodiments where the antagonist is not 6β-naltrexol, the second amount is a 6β-naltrexol equivalent amount, said 6β-naltrexol equivalent amount corresponding to 1.5 mg to 10 mg 6β-naltrexol administered orally to a 70 kg subject.

In some embodiments, the blood half-life of the antagonist is at least 2-fold greater than the blood half-life of the agonist in a subject to which the formulation is administered. In some embodiments, the blood half-life of the antagonist is at least 2-fold greater than the blood half-life of the agonist in a subject to which the formulation is administered.

In some embodiments, the agonist is alfentanil, allylprodine, alphaprodine, anileridine, benzylmorphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, fentanyl, heroin, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, narceine, nicomorphine, norlevorphanol, normethadone, noroxycodone, nalorphine, nalbuphene, normorphine, norpipanone, opium, oxycodone, oxymorphone, papaveretum, pentazocine, phenadoxone, phenomorphan, phenazocine, phenoperidine, piminodine, piritramide, propheptazine, promedol, properidine, propoxyphene, sufentanil, tilidine, tramadol, or a combination of two or more of the foregoing.

In some embodiments, the antagonist is a naltrexone analog. In some embodiments, the naltrexone analog is represented by the chemical structures set forth herein.

In some embodiments, the antagonist is a naloxone analog. In some embodiments, the naloxone analog is represented by the chemical structures set forth herein.

In some embodiments, the antagonist is selected from the group consisting of 6β-naltrexol, 6β-naltrexamide, 6β-naloxol, 6α-naltrexol, 6α-naloxol, 6α-naltrexamine, 6β-naltrexamine, 6-deoxynaltrexone, 6α-naltrexamide, a pharmaceutically acceptable physical isomorph of one of the foregoing, a pharmaceutically acceptable salt of one of the foregoing, or a combination of two or more of the foregoing.

In a related embodiment of the invention, there is provided a unit dosage of an analgesic composition comprising an opioid agonist in an amount sufficient to confer analgesia in a mammalian subject and a neutral opioid antagonist in an amount sufficient to inhibit peripheral effects, and insufficient to block substantial central effects, of the opioid agonist in the subject.

In a related embodiment of the invention, the analgesic composition comprises an opioid agonist, which is selected from the group consisting of alfentanil, allylprodine, alphaprodine, anileridine, benzylmorphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, fentanyl, heroin, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, narceine, nicomorphine, norlevorphanol, normethadone, noroxycodone, nalorphine, nalbuphene, normorphine, norpipanone, opium, oxycodone, oxymorphone, papaveretum, pentazocine, phenadoxone, phenomorphan, phenazocine, phenoperidine, piminodine, piritramide, propheptazine, promedol, properidine, propoxyphene, sufentanil, tilidine and tramadol, in an amount sufficient to confer analgesia in a mammalian subject. In addition, the neutral opioid antagonist may be a naloxone or naltrexone analog showing neutral nonaversive properties.

Naltrexone analogs may be represented by formula Iα or Iβ, including pharmaceutically acceptable salts thereof:

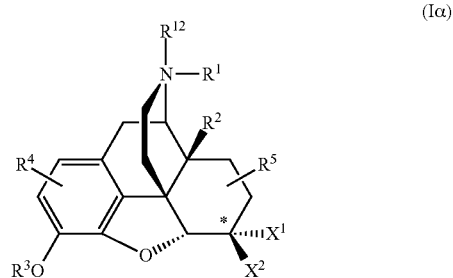

(Iα)

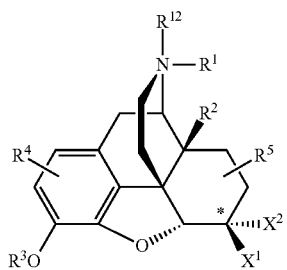

(Iβ)

wherein:

$R^1$ is cycloalkyl(alkyl), for example, $C_3$-$C_7$ (cycloalkyl) alkyl, for example, $C_3$-$C_7$ (cycloalkyl)methyl such as (cyclopropyl)methyl or $C_5$-$C_7$ (cycloalkenyl)alkyl;

$R^2$ is H, OH or esters thereof, such as —OAc($O_2$C(alkyl)), for example $O_2$($C_1$-$C_6$ alkyl);

$R^3$ is H, alkyl for example, $C_1$-$C_6$ alkyl, or (alkyl)C=O for example, (($C_1$-$C_6$)alkyl)-C=O;

$R^4$ and $R^5$ are independently H, halogen (F, Cl, Br or I), alkyl, for example $C_1$-$C_6$ alkyl, alkoxy, such as $C_1$-$C_4$ alkoxy, nitro, amino, cyano, carboxyl or acyl which may be substituted for one or more hydrogens on the ring;

$X^1$ and $X^2$ are the same or different, and may be H, $C_1$-$C_6$ alkyl, —$OR_6$, —$NR^7R^8R^9$, —$NCOR^{10}$, —$NO_2$, or —$SR^{11}$,
wherein, $R^6$ and $R^{11}$ are independently H, alkyl, for example $C_1$-$C_6$ alkyl, substituted alkyl, cycloalkyl, for example $C_3$-$C_7$ cycloalkyl, substituted cycloalkyl, aryl, for example phenyl, naphthyl, imidazole, quinoline, isoquinoline, oxazole, benzoxazole, thiazole, pyrimidyl, pyrazolyl, indole, substituted aryl, acyl, for example $C_1$-$C_n$ acyl such as —C(O)—$C_1$-$C_6$ alkyl wherein n is typically 6-10 but may be 10-20 or greater, aroyl, for example benzoyl, naphthoyl, imidazoyl, quinolinoyl, isoquinolinoyl, oxazoyl, benzoxazoyl, thiazoyl, indoyl, and pyrimidoyl, polyethyleneglycyl (PEGyl), or other similar substitutions such as polyether groups;

$R^7$, $R^8$ and $R^{10}$ are independently hydrogen, alkyl, for example $C_1$-$C_6$ alkyl, substituted alkyl, cycloalkyl for example $C_3$-$C_7$ cycloalkyl, substituted cycloalkyl, aryl, substituted aryl;

$R^9$ and $R^{12}$ can be present or absent and are independently hydrogen, alkyl, for example $C_1$-$C_6$ alkyl, substituted alkyl, cycloalkyl for example $C_3$-$C_7$ cycloalkyl, substituted cycloalkyl, aryl, for example phenyl, naphthyl, imidazole, quinoline, isoquinoline, oxazole, benzoxazole, thiazole, pyrimidyl, pyrazolyl, indole, substituted aryl;
and pharmaceutically acceptable salts thereof.

Naloxone analogs may be represented by formula Iα or Iβ, including pharmaceutically acceptable salts thereof:

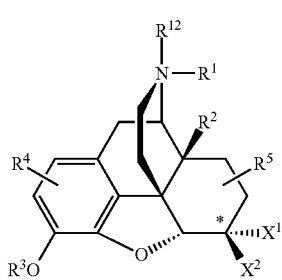

(Iα)

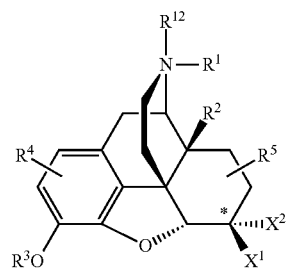

(Iβ)

wherein:

$R^1$ is alkenyl, for example $C_3$-$C_6$ alkenyl, such as allyl;

$R^2$ is H, OH or esters thereof, such as —OAc($O_2$C(alkyl)), for example $O_2$($C_1$-$C_6$ alkyl);

$R^3$ is H, alkyl for example, $C_1$-$C_6$ alkyl, or (alkyl)C=O for example, (($C_1$-$C_6$)alkyl)-C=O;

$R^4$ and $R^5$ are independently H, halogen (F, Cl, Br or I), alkyl, for example $C_1$-$C_6$ alkyl, alkoxy, such as $C_1$-$C_4$ alkoxy, nitro, amino, cyano, carboxyl or acyl which may be substituted for one or more hydrogens on the ring;

$X^1$ and $X^2$ are the same or different, and may be H, alkyl, —$OR_6$, —$NR^7R^8R^9$, —$NCOR^{10}$, —$NO_2$, or —$SR^{11}$,
wherein, $R^6$ and $R^{11}$ are independently H, alkyl, for example $C_1$-$C_6$ alkyl, substituted alkyl, cycloalkyl, for example $C_3$-$C_7$ cycloalkyl, substituted cycloalkyl, aryl, for example phenyl, naphthyl, imidazole, quinoline, isoquinoline, oxazole, benzoxazole, thiazole, pyrimidyl, pyrazolyl, indole, substituted aryl, acyl, for example $C_1$-$C_n$ acyl such as —C(O)—$C_1$-$C_6$ alkyl wherein n is typically 6-10 but may be 10-20 or greater, aroyl, for example benzoyl, naphthoyl, imidazoyl, quinolinoyl, isoquinolinoyl, oxazoyl, benzoxazoyl, thiazoyl, indoyl, and pyrimidoyl, polyethyleneglycyl (PEGyl), or other similar substitutions such as polyether groups;

$R^7$, $R^8$ and $R^{10}$ are independently hydrogen, alkyl, for example $C_1$-$C_6$ alkyl, substituted alkyl, cycloalkyl for example $C_3$-$C_7$ cycloalkyl, substituted cycloalkyl, aryl, substituted aryl;

$R^9$ and $R^{12}$ can be present or absent and are independently hydrogen, alkyl, for example $C_1$-$C_6$ alkyl, substituted alkyl, cycloalkyl for example $C_3$-$C_7$ cycloalkyl, substituted cycloalkyl, aryl, for example phenyl, naphthyl, imidazole, quinoline, isoquinoline, oxazole, benzoxazole, thiazole, pyrimidyl, pyrazolyl, indole, substituted aryl;
and pharmaceutically acceptable salts thereof.

For generic formulae Iα and Iβ, when $X^1$ and $X^2$ are the same, the stereocenter at this position, marked by an asterisk, goes away.

In related embodiments, the naloxone or naltrexone analog may include 6β-naltrexol, 6β-naltrexamide, 6β-naloxol, 6α-naltrexol, 6α-naloxol, 6α-naltrexamine, 6-deoxynaltrexone, 6β-naltrexamine, and 6α-naltrexamide, their derivatives named in 000 and 0011, pharmaceutically acceptable physical isomorphs thereof, and pharmaceutically acceptable salts thereof.

In a further related embodiment of the invention described above, the mammalian subject is a human.

In another related embodiment of the invention described above, the unit dosage is for oral or intravenous administration and the neutral opioid antagonist is 6β-naltrexol. Dosage ranges for the neutral antagonist relative to the analgesic, in separate formulations for co-administration, may range from a dosage of approximately 0.0008-0.08 mg of the neutral antagonist (e.g., 6β-naltrexol) per kg of body weight of the subject for i.v. administration of 6β-naltrexol given together with a standard dose of morphine (10 mg intravenously or 30-40 mg orally, assuming approximately 25% bioavailability of the orally administered opioid agonist), or a morphine-equivalent dosage (e.g., equi-analgesic equivalent) of a non-morphine opioid analgesics. For example, in some embodiments, the invention provides a dosage range of approximately 0.008-0.24 mg 6β-naltrexol per kg of body weight for oral administration of 6β-naltrexol with a standard dose of morphine or a morphine-equivalent dose of a non-morphine opioid agonist. If the opioid analgesic is increased in a single dose, the neutral antagonist may need to be increased accordingly, but in such a manner that greater accumulation of the opioid antagonist is taken into account. For example, doubling of the opioid analgesic dose per formulation may require a 1.5-fold increase of the neutral antagonist. In some embodiments, where opioid dependent subjects already being administered an opioid analgesic are more sensitive to any opioid antagonist (including neutral opioid antagonists even if to a lesser degree than to inverse antagonists), the initial dosage range may be from 0.008-0.08 mg of 6β-naltrexol per kg of body weight for oral administration of the neutral antagonist regardless of the mode of administration of the opioid agonist (e.g., the opioid agonist may be administered orally, intravenously, subcutaneously, etc.). These dosage ranges were calculated as "human equivalent dosages" from the effective dosages determined in rodent models and from results in opioid-dependent and -naïve human subjects. It is anticipated that some dosage adjustment be made for other species, and specifically humans. The dosage for the analgesic in separate formulations suitable for co-administration with the neutral antagonist, was an $A_{90}$ dosage in animals, which means it confers 90% analgesic activity, and a standard dose of morphine (naïve subjects) or methadone (chronic opioid dependent subjects).

In another related embodiment of the invention described above, the neutral opioid antagonist is 6β-naltrexamine in a dosage of approximately 0.004-1.2 mg per kg of body weight of the subject, where the subject has received a dosage of 10 mg morphine (orally) per 70 kg, or a morphine equivalent amount of a non-morphine opioid agonist.

In another related embodiment of the invention described above, the neutral opioid antagonist is 6β-naltrexamine in a dosage of approximately 0.002-0.8 mg per kg of body weight of the subject, where the subject has received a dosage of 10 mg morphine (orally) per 70 kg, or a morphine equivalent amount of a non-morphine opioid agonist.

In another related embodiment of the invention described above, the opioid agonist (i.e., opioid analgesic) is co-administered orally with neutral opioid antagonist. In still further related embodiments, the neutral opioid antagonist is 6β-naltrexamide in an oral administration with the agonist given by i.v., wherein the neutral antagonist dosage is approximately 0.024-0.8 mg per kg of body weight of the subject. Again, the analgesic is given the standard agonist doses as above.

Similar ranges are determined, as indicated, for other neutral antagonists of the present invention.

Another embodiment comprises a method for inhibiting peripheral effects of an opioid agonist (e.g., the effects of the agonist on the gastro-intestinal (GI) tract including constipation) while still permitting substantial central effects of the opioid agonist (e.g., analgesic effects of the agonist on the central nervous system (CNS)) in a subject, the method comprising co-administering the opioid agonist with an effective amount of a unit dosage of a neutral opioid antagonist formulated as described to a subject in need thereof.

In some embodiments, the invention provides a formulation comprising, consisting essentially of, or consisting of an opioid agonist in a first amount and a neutral opioid antagonist in a second amount, wherein the weight to weight (w/w) ratio of first amount to the second amount is at least 1:1; and a pharmaceutically acceptable carrier. In some embodiments, the w/w ratio of the first amount to the second amount is at least 2:1, or at least 3:1 or at least 5:1 or at least 7.5 to 1 or at least 10:1, or at least 15:1, or at least 20:1.

In some embodiments, the blood half-life of the antagonist is at least 2-fold greater than the blood half-life of the agonist in a subject to which the formulation is administered.

In some embodiments, the first amount is a morphine equivalent amount. In some embodiments, the first amount is sufficient to confer analgesia in a subject to which the formulation is administered.

In some embodiments, the second amount is an amount of the neutral antagonist that is sufficient to substantially inhibit peripheral effects of the first amount of the opioid agonist but is insufficient to block substantial central effects of the first amount of opioid agonist in a subject to which the formulation is administered.

In some embodiments, overly frequent administration of the formulation to a subject causes a greater increase in blood concentration of the antagonist than of the agonist in the subject, so as to deter diversion, discourage abuse and/or reduce addiction liability to the agonist in the subject resulting from such administration.

In some embodiments, the formulation is formulated for oral administration to a subject, for transdermal administration to a subject, or for parenteral administration (e.g., subcutaneous injection, intravenous injection, etc.) to a subject. In some embodiments, the subject is a mammalian subject. In some embodiments, the subject is a human subject. In some embodiments, the subject is a domesticated animal (e.g., cat, dog, horse, cow, goat, sheep, bird, or reptile).

In some embodiments, the agonist is morphine. In some embodiments, the agonist is alfentanil, allylprodine, alphaprodine, anileridine, benzylmorphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, fentanyl, heroin, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, narceine, nicomorphine, norlevorphanol, normethadone, noroxycodone, nalorphine, nalbuphene, normorphine, norpipanone, opium, oxycodone, oxymorphone, papaveretum, pentazocine, phenadoxone, phenomorphan, phenazocine, phenoperidine, piminodine, piritramide, propheptazine, promedol, properidine, propoxyphene, sufentanil, tilidine, tramadol, or a combination of two or more of the foregoing.

In some embodiments, the antagonist is a naltrexone analog. In some embodiments, the naltrexone analog is represented by formula Iα or Iβ set forth herein.

In some embodiments, the antagonist is a naloxone analog. In some embodiments, the naloxone analog is represented by formula Iα or Iβ set forth herein.

In some embodiments, the antagonist is selected from the group consisting of 6β-naltrexol, 6β-naltrexamide, 6β-naloxol, 6α-naltrexol, 6α-naloxol, 6α-naltrexamine, 6β-naltrexamine, 6-deoxynaltrexone, 6α-naltrexamide, a pharmaceutically acceptable physical isomorph of one of the foregoing, a pharmaceutically acceptable salt of one of the foregoing, or a combination of two or more of the foregoing.

Still another embodiment provides a method of deterring addiction in a subject being administered an opioid agonist, the method comprising co-administering the opioid agonist (e.g., in an amount sufficient to confer analgesia in the subject or in a morphine-equivalent amount) with an effective amount of a unit dosage of a neutral opioid antagonist formulated according to as described to a subject in need thereof.

In related embodiments, the opioid agonist and unit dosage are administered orally, perorally, intragastrically, sublingually, by suppository, or intravenously.

Other embodiments provide a pharmaceutical formulation that deters diversion of an opioid agonist, the formulation comprising an amount of opioid agonist sufficient to induce a euphoric state or sufficient to relieve pain upon ingestion or administration, the opioid agonist having a blood half-life, and an effective amount of a neutral opioid antagonist with a ratio fixed relative to that of the opioid agonist, the neutral antagonist having a blood half-life substantially longer than the blood half-life of the opioid agonist, wherein upon successive administration, the blood concentration ratio of neutral opioid antagonist to opioid agonist increases with each successive administration, as measured in mg per kg of body weight of the subject, and such that repeated administration of the formulation in a dosage regimen exceeding therapeutically recommended limits results in reduced euphoria and reduced pain relief in the subject and so deters addiction abuse and diversion (i.e., use of the opioid agonist for non-medical use), because the opioid analgesics and the antagonists herein have similar structures so that they cannot be readily separated for systemic administration.

Yet another embodiment provides a method for inhibiting peripheral effects of an opioid agonist while still permitting substantial central effects of the opioid agonist in a subject in need thereof, the method comprising co-administering to the subject in need thereof the opioid agonist with an effective amount of a unit dosage of a neutral opioid antagonist, the effective amount sufficient to inhibit peripheral opioid agonist effects and insufficient to block substantial central effects in the subject.

A more particular embodiment provides a method of deterring addiction in a subject being administered an opioid agonist, the method comprising co-administering to the subject the opioid agonist with an effective amount of a unit dosage of a neutral opioid antagonist, the effective amount sufficient to reduce euphoria and reduce pain relief upon successive administrations beyond therapeutically recommended limits, thereby deterring addiction.

In related method embodiments, the unit dosage of the opioid antagonist is selected from the group consisting of 6β-naltrexol, 6β-naltrexamide, 6β-naloxol, 6α-naltrexol, 6α-naloxol, 6α-naltrexamine, 6β-naltrexamine, 6-deoxynaltrexone, and 6α-naltrexamide, and derivatives described herein, pharmaceutically acceptable physical isomorphs thereof, and pharmaceutically acceptable salts thereof. Lists of suitable pharmaceutically acceptable salts are found in Remington's Pharmaceutical Sciences, 17th ed., Mack Publishing Company, Easton, Pa. (1985), which is hereby incorporated by reference in its entirety.

In other related method embodiments, the opioid agonist and unit dosage may be administered in a manner selected from the group consisting of orally, perorally, intragastrically, sublingually, by suppository, intravenously and a combination thereof, and wherein co-administration is overlapping such that administration may be of a single co-formulation comprising agonist and antagonist, or may be simultaneous or sequential administration of separate agonist and antagonist formulations.

In various related embodiments of this invention, the opioid agonist of the analgesic composition is hydrocodone. In other particular embodiments, the unit dosage, pharmaceutical composition, and any or all of the methods may further comprise a neutral opioid antagonist that is suitable for formulation in a slow-release formulation, or is formulated in a slow-release formulation.

In a further related embodiment of the invention described above, the neutral opioid antagonist has a blood half-life substantially longer than the blood half-life of the opioid agonist, so that repeated abusive administration of the dosage causes a greater increase in blood concentration of the antagonist than of the agonist, so as to deter diversion, discourage abuse and/or reduce addiction liability to the agonist resulting from such administration.

In a further related embodiment of the invention described above, the neutral antagonist has physicochemical properties similar to that of the opioid agonist, so as to deter diversion of the agonist by extraction or other means.

In various embodiments, whether the embodiments are methods for inhibiting peripheral effects, deterring diversion or addiction, or reducing addiction liability, among other methods, are whether the embodiments are for a unit dosage or a pharmaceutical composition, the neutral antagonist may be formulated alone or together with the opioid agonist in a slow-release co-formulation. In such co-formulations, the neutral antagonist may be provided with an opioid agonist wherein only the neutral antagonist is provided in a slow-release form. Other embodiments provide a neutral antagonist with an opioid agonist in a co-formulation, wherein only the opioid agonist is provided in the co-formulation in a slow-release form. Still other embodiments provide a neutral antagonist with the opioid agonist in a co-formulation, wherein both the neutral antagonist and the opioid agonist are formulated as slow-release agents.

To deter diversion the neutral antagonist of the present invention is relatively lipophilic, similar to the agonists, so as to gain in oral bioavailability; moreover, greatest protection against diversion is achieved by making the two components in a co-formulation not easily separable. Further, the neutral antagonist is potent and is at least partially excluded from the brain, not primarily by means of high polarity, which also tends to reduce receptor potency (such as occurs with methylnaltrexone (MNTX)), but by other means, including but not limited to, the action of an extrusion pump (e.g. —the multidrug resistance pump MDR1, which also keeps loperamide (immodium) out of the brain). The combination of these features makes the compounds of the invention unique. Lastly, such potent and relatively lipophilic antagonists have the tendency to show significantly delayed central activity (for kinetic reasons) compared to peripheral effects. This is advantageous for short term use, and it facilitates dosage schedules that prevent inappropriate dosage escalation.

BRIEF DESCRIPTION OF THE DRAWINGS

The patent or application file contains at least one drawing executed in color. Copies of this patent with color drawing(s) will be provided by the Patent and Trademark Office upon request and payment of necessary fee.

The foregoing features of the invention will be more readily understood by reference to the following detailed description, taken with reference to the accompanying drawings, in which FIGS. 1A-17C are results from studies in mice, and FIGS. 18-21B are results from human studies:

FIG. 1A is a graph that shows data reflecting the duration of the inhibitory effects of intravenously-administered 6β-naltrexol on an antinociceptive, intravenous dose of hydrocodone, and demonstrates the time of peak effect of antinociception inhibition in mice.

FIG. 3 is a graph that shows data reflecting the potency of the inhibitive effects of various concentrations of orally-administered 6β-naltrexol on an orally-co-administered, antinociceptive dose of hydrocodone.

FIG. 5 is a dose response curve reflecting the potency of 6β-naltrexol to reverse hydrocodone-induced GI transit slowing when the two compounds are orally co-administered.

FIG. 9 is a graph that shows data reflecting the potency of the inhibitory effects of various concentrations of orally-administered 6β-naltrexamide on an orally-co-administered, antinociceptive dose of hydrocodone.

FIG. 14 is a graph that shows data reflecting the potency of the antinociception-inhibitive effects of various concentrations of orally-administered naltrexone on an orally-co-administered, antinociceptive dose of hydrocodone.

FIG. 16 is a dose response curve reflecting the potency of naltrexone to reverse hydrocodone-induced GI transit slowing when the two compounds are orally co-administered.

FIG. 17C shows the summarized potency data for inhibition of the effects of hydrocodone by naltrexone in the GI transit studies (peripheral effects) and antinociception studies (central effects) where both compounds are orally co-administered.

FIG. 18 is a line graph showing 6β-naltrexol plasma pharmacokinetics in humans. Semi-log plasma concentration-time plots in individuals after i.v. dosing (30 min. infusion) with 3 mg (N=5, green lines) or 10 mg (N=5, blue lines) of 6β-naltrexol in humans.

FIGS. 19A, 19B, and 19C are line graphs showing the simulated plasma concentration-time profiles for combined oxycodone (20 mg) and 6β-naltrexol (AIKO-150; 7.5 mg) formulation after oral dosing with an immediate release formulation, in humans. Dosing intervals (12 and 2 hrs) are indicated for each plot (FIG. 19A: every 12 hour; FIG. 19B: every 2 hour, and FIG. 19C: initially every 12 hours, and then switching to every 2 hours to simulate acquired abuse of the combination oxycodone/6β-naltrexol formulation). The plasma levels of oxycodone are shown in solid blue lines, and the plasma levels of 6β-naltrexol are shown in dashed green line. Oxycodone, used here as the opioid analgesic, has pharmacokinetics parameters and a potency similar to that of morphine (see Tables 1A and 1B).

FIG. 20 is a bar graph showing the Oral-Cecal Transit Times measured by the time of peak exhaled $H_2$ in breath over 4 hours at 15 min intervals following intravenous infusion of the indicated amount of 6β-naltrexol in the presence or absence of morphine. Bars are standard error.

FIGS. 21A and 21B are bar graphs showing the effect of 6β-naltrexol on Opioid-Induced Pupil Constriction and Analgesia. FIG. 21A shows the lack of 6β-naltrexol effects on morphine-induced pupil constriction at 1 and 2 hours after the dose. FIG. 21B shows the Mean Latency Times in cold pressor tests expressed as a percent of predose values. Bars represent standard error of the mean.

DETAILED DESCRIPTION OF SPECIFIC EMBODIMENTS

Figure 1A:
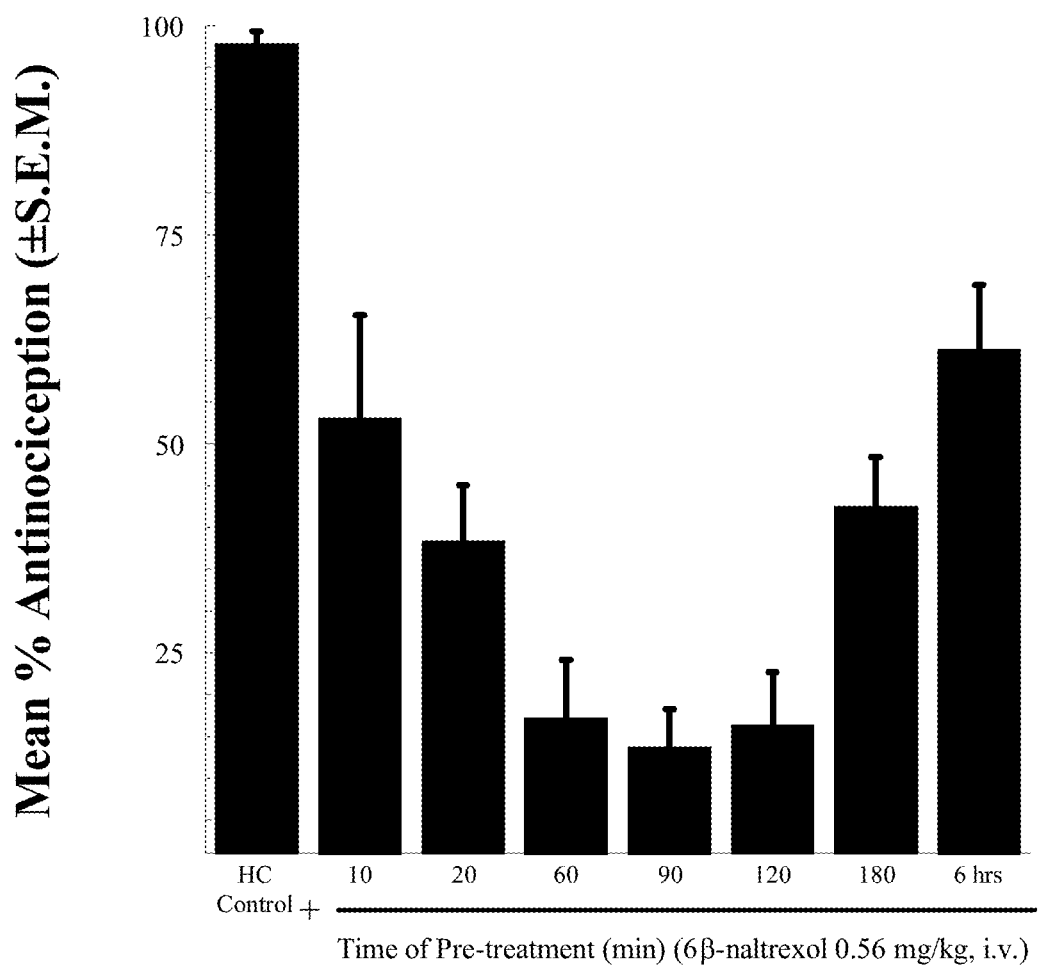

Definitions. As used in this description and the accompanying claims, the following terms shall have the meanings indicated, unless the context otherwise requires:

6β-naltrexol is a naltrexone analog with the following structure:

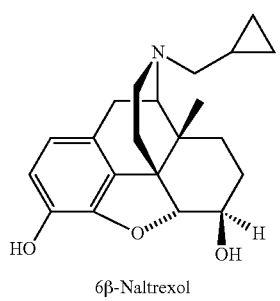

6β-Naltrexol

6β-naltrexamide is a naltrexone analog with the following structure:

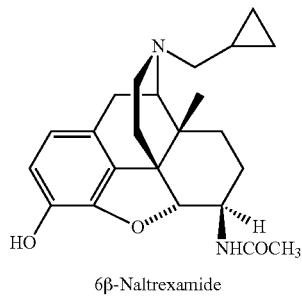

6β-Naltrexamide

Compounds. 6β-Naltrexol and 6β-Naltrexamide may be represented by the generic formula Iβ, where the stereocenter at position 6 is indicated by an asterisk.

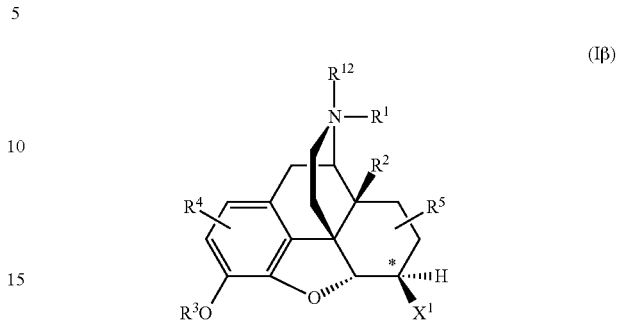

The alpha isomers of 6-Naltrexol and 6-Naltrexamide may be represented by the generic formula Iα:

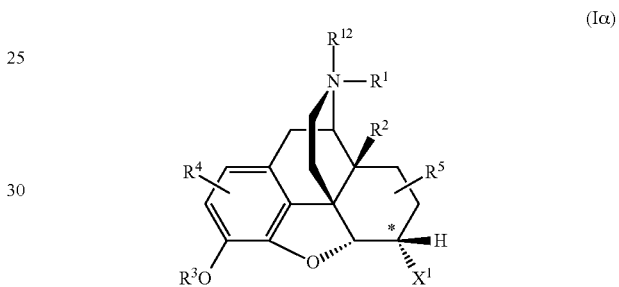

For generic formulae I α and Iβ, when $X^1$ and $X^2$ are the same, the stereocenter at this position, marked by an asterisk, goes away.

"$ID_{50}$ value" refers to a dose which inhibits activity by 50%.

"A blood half-life substantially longer than the blood half-life of the opioid agonist" as used herein means a blood half-life that is in the order of 2-fold greater, or more, as measured at $t_{1/2}$=60 min than that for the opioid agonist.

"$A_{90}$ dose" refers to the dose, for example of an opioid agonist, which produces 90% analgesic activity.

Pharmaceutically acceptable salts of the naltrexone and naloxone analogs, which are neutral antagonists at the μ opioid receptor, include salts derived from an appropriate base, such as an alkali metal (for example, sodium, potassium), an alkaline earth metal (for example, calcium, magnesium), ammonium and $NX._4^+$ (wherein X is $C_1$-$C_4$ alkyl). Pharmaceutically acceptable salts of an amino group include salts of: organic carboxylic acids such as acetic, lactic, tartaric, malic, lactobionic, fumaric, and succinic acids; organic sulfonic acids such as methanesulfonic, ethanesulfonic, isethionic, benzenesulfonic and p-toluenesulfonic acids; and inorganic acids such as hydrochloric, hydrobromic, sulfuric, phosphoric and sulfamic acids.

In enantiomeric forms, compounds of the invention include individual enantiomers of the compounds in single species form substantially free of the corresponding enantiomer, as well as in admixture (in mixtures of enantiomeric pairs and/or in mixtures of multiple enantiomer species).

Opiates are a class of centrally acting compounds and are frequently used agents for pain control. Opiates are narcotic agonistic analgesics and are drugs derived from opium, such as morphine, codeine, and many synthetic congeners of morphine, with morphine being the most widely used derivative. Opioids are natural and synthetic drugs with morphine-like actions and include the opiates. Opioids are narcotic agonistic analgesics which produce drug dependence of the morphine type and are subject to control under federal narcotics law because of their addicting properties. Thus, an opioid is sometimes referred to as an opioid agonist or an opioid analgesic.

The chemical classes of opioids with morphine-like activity are the purified alkaloids of opium consisting of phenanthrenes and benzylisoquinolines, semi-synthetic derivatives of morphine, phenylpiperidine derivatives, morphinan derivatives, benzomorphan derivatives, diphenyl-heptane derivatives, and propionanilide derivatives. The principal phenanthrenes are morphine, codeine, and thebaine. The principal benzoisoquinolines are papaverine, a smooth muscle relaxant, and noscapine. Semi-synthetic derivatives of morphine include diacetylmorphine (heroin), hydromorphone, oxymorphone, hydrocodone, apomorphine, etorpine, and oxycodone. Phenylpiperidine derivatives include meperidine and its congeners diphenoxylate and loperamide, alphaprodine, anileridine hydrochloride or phosphate, and piminodine esylate. Morphinan derivatives include levorphanol. The diphenyl-heptane derivatives include methadone and its congeners, and propoxyphene. Propionanilide derivatives include fentanyl citrate and its congeners sufentanil citrate and alfenatil hydrochloride.

As used herein, a "therapeutically effective amount" refers to the amount of the naltrexone or naloxone analog or sustained release composition having the naltrexone or naloxone analog incorporated therein, needed to elicit the desired biological response following administration. The desired biological response herein can be sufficient blockade of the µ opioid receptor resulting in reducing adverse peripheral effects associated with current pain management such as diarrhea and constipation (effects on the GI tract) and without significantly inhibiting the central effects such as pain relief (analgesic effects on the CNS).

The neutral antagonist compositions of this invention can be administered by any route into a subject (for example, a human, or an animal. For example, a neutral antagonist can be administered orally, transdermally, or parenterally such as by injection, (e.g., subcutaneously, intramuscularly, intraperitoneally, intravenously, intracranially, and intradermally), or by implantation or by administration to mucosal membranes (e.g., intranasally, intravaginally, intrapulmonary, buccally or by means of a suppository), or by in situ delivery (e.g., by enema or aerosol spray) to provide the desired dosage of neutral antagonist to modulate undesirable peripheral effects of narcotic opioid analgesic (such constipation, nausea, vomiting) in the treatment of pain or anesthesia, in an individual in need thereof.

"Neutral antagonists" (or "neutral opioid antagonist") as that term is used herein, refers to agents that block the effects of an agonist at the target receptor, but do not significantly affect the level of spontaneous activity present at the target receptor. "Neutral antagonist at the µ opioid receptor" as that term is used herein refers to an agent which can bind selectively to the resting, drug-sensitive µ opioid receptor state, to the constitutively active µ opioid receptor state, or to both, blocking the effects of an agonist at the receptor, but not significantly effecting the level of spontaneous activity present at the receptor.

In some embodiments, a neutral antagonist has a neutral character to reduce the potential for opioid agonist withdrawal. U.S. Pat. No. 6,713,488 (incorporated herein by reference in its entirety) lists some neutral antagonists and their properties. Non-limiting examples of neutral antagonists include 6β-naltrexol, 6β-naltrexamide and 6β-naltrexamine. In some embodiment, naloxone is not a neutral antagonist. In some embodiments, naltrexone is not a neutral antagonist. Of course, certain analogs of naltrexone and naloxone (such as the analogs described herein or in U.S. Pat. No. 6,713,488) are neutral antagonists.

Additional non-limiting neutral antagonists include naltrexol naloxol, naltrexamine and naloxamine, and their derivatives, such as ethers (e.g., pegylated, acetylated, etc). Some neutral antagonists can be derived from non-neutral antagonists such as naloxone or naltrexone.

In some embodiments, a neutral antagonist administered to a subject by any route (e.g., orally, transdermally, or parenterally) is able to reach the circulation (i.e., is systemically bioavailable), and hence reach all peripheral organs and cells in the blood, including the gastro-intestinal (GI) tract from the blood circulation (thereby exerting intestinal effects from the luminal GI tract and the circulation). Thus, in contrast to some other opioid antagonist with selective effects on the GI tract (i.e., antagonists that are also not neutral antagonists), both 6β-naltrexol and 6β-naltrexamide have shown good oral bioavailability approaching 20%. The oral bioavailability of either 6β-naltrexol or 6β-naltrexamide in humans is estimated to be approximately 25%, similar to that of morphine, and consistent with its similar physicochemical characteristics. In some embodiments, the neutral antagonist has a relatively restricted access to the central nervous system (CNS). For example, under a therapeutic dosage regimen, the analgesic potency of an opioid agonist is not diminished by the neutral antagonist. In earlier experiments in mice, the selectivity of 6β-naltrexol in blocking peripheral over central opioid effects was approximately tenfold upon oral administration. In other words, when an opioid agonist and neutral antagonist 6β-naltrexol are orally co-administered, the peripheral effects of the opioid agonist (e.g., GI issues) are blocked ten-fold more potently than the CNS effects (e.g., analgesia) are blocked. Likewise, in mice, the selectivity of 6β-naltrexamide in blocking peripheral over central opioid effects was approximately twenty-fold upon oral administration. In contrast, naltrexone, which is also not a neutral antagonist) was equipotent for blocking both the peripheral and central effects of a co-administered opioid agonist, and thus showed no selectivity. As described in Examples 8 and 9 below, in human eIND trials, the ID50 of 6β-naltrexol in blocking GI slowing (i.e., peripheral effects) caused by 10 mg morphine i.v. was approximately 3 mg, with 20 mg completely blocking morphine's GI effects while having no detectable effect on analgesia and pupil constriction (both CNS effects) induced by the morphine. Therefore, the peripheral over central potency of 6β-naltrexol is at least tenfold or more in humans In some embodiments, the neutral antagonist has a blood elimination half-life that is substantially longer than the blood elimination half-life of the opioid agonist, so as to accumulate upon frequent administration to a greater extent than the opioid agonist (e.g., an opioid agonist that the neutral antagonist is co-administered with). In some embodiments, a neutral opioid antagonist has a blood half-life that is substantially longer than the blood half-life of the opioid agonist that it is co-administered with, as measured at a half-life ($t_{1/2}$) equaling 60 minutes (i.e., 60 minutes after the co-administration). In some embodiments, the blood half-life of the neutral opioid agonist is 2-fold longer than the blood half-life of the opioid agonist that it is co-administered with. In some embodiments, the blood half-life of the neutral opioid agonist is 3-fold longer than the blood half-life of the opioid agonist that it is co-administered with. In some embodiments, the blood half-life of the neutral opioid agonist is 4-fold longer than the blood half-life of the opioid agonist that it is co-administered with. In some embodiments, the blood half-life of the neutral opioid agonist is 5-fold longer than the blood half-life of the opioid agonist that it is co-administered with. In some embodiments, the blood half-life of the neutral opioid agonist is 10-fold longer than the blood half-life of the opioid agonist that it is co-administered with.

The eIND studies described below confirmed a blood half-life of approximately 12 hours for 6β-naltrexol (see FIG. 18), similar to literature estimates, measured after administration of naltrexone (6β-naltrexol is its major metabolite). This blood half-life range is 3-4 times longer than that the blood half-lives of the most commonly used oral opioid analgesic formulations. A simulation of the accumulation of an opioid analgesic and 6β-naltrexol in humans is provided in FIGS. 19A-19C, showing the selective accumulation of 6β-naltrexol as compared to the accumulation of the opioid analgesic.

In some embodiments, the invention includes a co-formulation product comprising an opioid agonist and a neutral antagonist (e.g., in a unit dosage) where the neutral antagonist is difficult (e.g., extremely difficult) to separate from the opioid agonist by simple extraction. Both 6β-naltrexol and 6β-naltrexamide are chemically very similar to the commonly used opioid analgesics (the compounds are all oxymorphinans) so that selective extraction of the neutral antagonist away from the opioid analgesic with organic solvents or other methods are not readily implemented for most opioid analgesics. This impedes diversion for parenteral administration (e.g., parenteral injection of an extract that contains a larger amount of the opioid agonist than of the neutral antagonist.

In some embodiments, the naloxone and naltrexone analogs represented by the structures presented herein are neutral antagonists. The naloxone and naltrexone analogs represented by the structures presented herein can be synthesized using standard synthetic procedures such as those described in March J., Advanced Organic Chemistry, 3rd Ed. (1985), employing, for example, naltrexone or naloxone as the starting material.

Many of the analogs of naltrexone and naloxone which possess neutral antagonist activity at the μ opioid receptor, for example, the analogs wherein the 6-keto functionality has been reduced to an —OH functionality, are known compounds, and their syntheses have been described, for example, by Chatterjie et al., *J. Med. Chem.*, 18, pp. 490-492 (1975) and Jiang et al., J. Med. Chem., 20, pp. 1100-1102 (1977), incorporated by reference herein. When modification of the naltrexone or naloxone at the 6-keto position results in an additional chiral carbon in the analog, the β orientation at the newly formed chiral carbon is preferred over the α orientation, although the latter may be also appropriate in certain applications. This preference is based upon the probably slower conversion of the β analogs back to naloxone or naltrexone, but exact data are limited for this conclusion. Further, if desired, metabolic conversion of the naltrexone or naloxone analog back to naltrexone or naloxone can be blocked by any suitable inhibitory agent. For example, in the case of 6β or 6α-naloxol or naltrexol, conversion of the —OH at the 6 position back to the keto functionality of the naloxone or naltrexone can be inhibited with alcohol dehydrogenase inhibitors, such as 4-methylpyrazole (Plapp, B. V., "Control of Alcohol Metabolism," pp. 311-322 in Towards a Molecular Basis of Alcohol Use and Abuse, eds. Janssen et al., Birkhaeuser Verlag, 1994). Further, the replacement of the 6-keto functionality with, for example, an amine or amide, results in 6α- and 6β-naltrexamine and 6α- and 6β-naltrexamide likely undergoing much slower, if any, conversion to naltrexone.

Other examples of potential neutral antagonists include the C-6-$H_2$ reduced analogue of naltrexol (access to the CNS++), whose molecular formula is $C_{20}H_{25}NO_3$ and whose IUPAC name is 17-(cyclopropylmethyl)4,5-epoxy-3,14-dihydroxy-morphinan but for the purposes of this application is referred to as 6-deoxynaltrexone. Still other possibilities for neutral antagonists, based on the naloxone or naltrexone core formulas, can be envisioned, or may be identified, and are considered to fall within the scope of the invention and encompassed by the claims. For example, the C-6 position could be modified in other ways, whether by replacement of the keto group with halogens, alkyl- and alkoxyl groups, alkylamine groups, vinyl groups, secondary and tertiary amine groups, among others, or by modification at other sites, or in other ways, that retain the neutral antagonist activity at the μ receptor.

This definition of neutral antagonist also encompasses compounds that are not based on the naltrexone or naloxone core formulas, but may represent a new type of compound that still possesses the properties associated with a neutral antagonist of the μ receptor.

Thus, while the concept of neutral antagonist has been particularly shown and described with references to preferred embodiments thereof, it will be understood by those skilled in the art that various changes in form and details to the neutral antagonist core formulas, or to the development of completely unrelated core formulas for neutral antagonists, may be made therein without departing from the scope of the invention encompassed by the appended claims.

The term "sustained release composition" as defined herein, can comprise a biocompatible polymer having incorporated therein at least one naloxone or naltrexone analog which is a neutral antagonist at the μ opioid receptor. Suitable biocompatible polymers, can be either biodegradable or non-biodegradable polymers or blends or copolymers thereof, as described herein.

The sustained release compositions of the present inventions may comprise a neutral antagonist formulated alone or together with an opioid agonist in a slow-release co-formulation. In such co-formulations, the neutral antagonist may be provided with an opioid agonist wherein only the neutral antagonist is provided in a slow-release form. In other co-formulations with a neutral antagonist and an opioid agonist, only the opioid agonist is provided in the co-formulation in a slow-release form. And in still other co-formulations with a neutral antagonist and an opioid agonist, both the neutral antagonist and the opioid agonist are formulated as slow-release agents.

The sustained release compositions of this invention can be formed into many shapes such as a film, a pellet, a rod, a filament, a cylinder, a disc, a wafer or a microparticle. A microparticle is preferred. A "microparticle" as defined herein, comprises a polymer component having a diameter of less than about one millimeter and having a naltrexone or naloxone analog which is a neutral antagonist at the μ opioid receptor dispersed therein. A microparticle can have a spherical, non-spherical or irregular shape. Typically, the microparticle will be of a size suitable for injection. A preferred size range for microparticles is from about one to about 180 microns in diameter.

As defined herein, a sustained release of a naltrexone or naloxone analog of the present invention is a release of the agent from a sustained release composition. As explained above, a sustained release of a neutral antagonist with an opioid agonist may be release of the antagonist, or release of the agonist, or release of both the neutral antagonist and the opioid agonist from a sustained release composition. The release occurs over a period which is longer than that period during which a therapeutically significant amount of the naloxone or naltrexone analog, or the opioid agonist, would be available following direct administration of a solution of the analog. The period of sustained release can be, for example, about one day, about two days, about seven days, about ten days to one month, or more, as needed to attain the desired results. A sustained release of a naltrexone or naloxone analog of the invention from a sustained release composition, or of an opioid agonist in a co-formulation with a neutral antagonist from a sustained release composition, may be a continuous or a discontinuous release, with relatively constant or varying rates of release. The continuity of release and level of release can be affected by the type of polymer composition used (e.g., monomer ratios, molecular weight, and varying combinations of polymers), agent loading, and/or selection of excipients to produce the desired effect.

The polymers of the sustained release compositions described herein are biocompatible. Suitable biocompatible polymers, can be either biodegradable or non-biodegradable polymers or blends or copolymers thereof, as described herein.

Suitable biocompatible polymers, can be either biodegradable or non-biodegradable polymers or blends or copolymers thereof, as described herein. A polymer is biocompatible if the polymer and any degradation products of the polymer are non-toxic to the recipient and also possess no significant deleterious or untoward effects on the recipient's body, such as an immunological reaction at the injection site.

"Biodegradable", as defined herein, means the composition will degrade or erode in vivo to form smaller chemical species. Degradation can result, for example, by enzymatic, chemical and physical processes. Suitable biocompatible, biodegradable polymers include, for example, poly(lactides), poly(glycolides), poly(lactide-co-glycolides), poly(lactic acid)s, poly(glycolic acid)s, polycarbonates, polyesteramides, polyanhydrides, poly(amino acids), polyorthoesters, poly(dioxanone)s, poly(alkylene alkylate)s, copolymers or polyethylene glycol and polyorthoester, biodegradable polyurethane, blends thereof, and copolymers thereof.

Suitable biocompatible, non-biodegradable polymers include non-biodegradable polymers selected from the group consisting of polyacrylates, polymers of ethylene-vinyl acetates and other acyl substituted cellulose acetates, non-degradable polyurethanes, polystyrenes, polyvinylchloride, polyvinyl fluoride, poly(vinyl imidazole), chlorosulphonate polyolefin, polyethylene oxide, blends thereof, and copolymers thereof.

Acceptable molecular weights for polymers used in this invention can be determined by a person of ordinary skill in the art taking into consideration factors such as the desired polymer degradation rate, physical properties such as mechanical strength, and rate of dissolution of polymer in solvent. Typically, an acceptable range of molecular weight is of about 2,000 Daltons to about 2,000,000 Daltons.

In a particular embodiment, the polymer is biodegradable polymer or copolymer. In a more preferred embodiment, the polymer is a poly(lactide-co-glycolide)(hereinafter "PLG"). The PLG can have a lactide:glycolide ratio, for example, of about 10:90, 25:75, 50:50, 75:25 or 90:10 and a molecular weight of about 5,000 Daltons to about 70,000 Daltons.

It is understood that when the naltrexone or naloxone analog, which is a neutral antagonist at the μ opioid receptor, or when the opioid agonist, separately or in a co-formulation with a neutral antagonist, is incorporated into a biocompatible polymer for sustained release of the analog and/or agonist, the sustained release composition can include additional components that can stabilize the analog and/or modify the release profile of the naltrexone or naloxone analog from the sustained release composition. That is, the naltrexone or naloxone analog, or opioid agonist, of the sustained release composition can be stabilized against loss of potency and/or loss of activity, all of which can occur during formation of the sustained release composition having the naltrexone or naloxone analog and/or opioid agonist dispersed therein, and/or prior to and during in vivo release of the analog and/or agonist. In addition, the period of release of the naltrexone or naloxone analog, and/or the opioid agonist, can be prolonged.

Pharmaceutical compositions (including those described herein that comprise an opioid agonist, a neutral antagonist, or both an opioid agonist and a neutral antagonist) can be formulated in a conventional manner using one or more physiologically acceptable carriers including excipients and auxiliaries which facilitate processing of the active compounds into preparations which can be used pharmaceutically. Proper formulation is dependent upon the route of administration chosen. A summary of pharmaceutically acceptable carriers (including pharmaceutically acceptable excipients and vehicles) can be found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), all of which are incorporated herein by reference in their entireties. Non-limiting pharmaceutically acceptable carriers include calcium phosphate, magnesium stearate, talc, monosaccharides, disaccharides, starch, gelatin, cellulose, methyl cellulose, sodium carboxymethyl cellulose, dextrose, hydroxypropyl-.beta.-cyclodextrin, polyvinylpyrrolidinone, low melting waxes, ion exchange resins, sodium chloride, water, and the like, as well as combinations of any two or more thereof.

In some embodiments, a suitable excipient or a specific combination of excipients can be employed in the sustained and/or controlled release composition. Sustained or controlled release delivery systems may be used, such as a diffusion controlled matrix system or an erodible system, as described for example in: Lee, "Diffusion-Controlled Matrix Systems", pp. 155-198 and Ron and Langer, "Erodible Systems", pp. 199-224, in "Treatise on Controlled Drug Delivery", A. Kydonieus Ed., Marcel Dekker, Inc., New York 1992. The matrix may be, for example, a biodegradable material that can degrade spontaneously in situ and in vivo for, example, by hydrolysis or enzymatic cleavage, e.g., by proteases. The delivery system may be, for example, a naturally occurring or synthetic polymer or copolymer, for example in the form of a hydrogel. Exemplary polymers with cleavable linkages include polyesters, polyorthoesters, polyanhydrides, polysaccharides, polyphosphoesters, polyamides, polyurethanes, polyimidocarbonates and polyphosphazenes. "Excipient", as that term is used herein, is any agent which binds or interacts in a covalent or non-covalent manner or is included with the naloxone or naltrexone analog in the sustained release composition.

Suitable excipients include, for example, carbohydrates, amino acids, fatty acids, surfactants, and bulking agents, and are known to those skilled in the art. An acidic or a basic excipient is also suitable. The amount of excipient used is based on ratio to the naltrexone or naloxone analog, on a weight basis. For amino acids, fatty acids and carbohydrates, such as sucrose, trehalose, lactose, mannitol, dextran and heparin, the ratio of carbohydrate to analog, is typically between about 1:10 and about 20:1. For surfactants the ratio of surfactant to analog is typically between about 1:1000 and about 2:1. Bulking agents typically comprise inert materials. Suitable bulking agents are known to those skilled in the art.

The excipient can also be a metal cation component which acts to modulate the release of the naltrexone or naloxone analog. A metal cation component used in modulating release typically comprises at least one type of multivalent metal cation. Examples of metal cation components suitable to modulate release include or contain, for example, $Mg(OH)_2$, $MgCO_3$ (such as $4MgCO_3.Mg(OH)_2.5H_2O$), $MgSO_4$, $Zn(OAc)_2$, $Mg(OAc)_2$, $ZnCO_3$ (such as $3Zn(OH)_2.2ZnCO_3$), $ZnSO_4$, $ZnCl_2$, $MgCl_2$, $CaCO_3$, $Zn_3(C_6H_5O_7)_2$ and $Mg_3(C_6H_5O_7)_2$. A suitable ratio of metal cation component to polymer is between about 1:99 to about 1:2 by weight. The optimum ratio depends upon the polymer and the metal cation component utilized. A polymer matrix containing a dispersed metal cation component to modulate the release of a an agent from the polymer matrix is further described in U.S. Pat. No. 5,656,297 to Bernstein et al. the teachings of which are incorporated herein by reference in their entirety.

A number of methods are known by which sustained release compositions (polymer/active agent matrices) can be formed. In many of these processes, the material to be encapsulated is dispersed in a solvent containing a wall forming material. At a single stage of the process, solvent is removed from the microparticles and thereafter the microparticle product is obtained.

Methods for forming a composition for the sustained release of biologically active agent are described in U.S. Pat. No. 5,019,400, issued to Gombotz et al., and issued U.S. Pat. No. 5,922,253 issued to Herbert et al. the teachings of which are incorporated herein by reference in their entirety.

In this method, a mixture comprising a biologically active agent, a biocompatible polymer and a polymer solvent is processed to create droplets, wherein at least a significant portion of the droplets contains polymer, polymer solvent and the active. These droplets are then frozen by a suitable means. Examples of means for processing the mixture to form droplets include directing the dispersion through an ultrasonic nozzle, pressure nozzle, Rayleigh jet, or by other known means for creating droplets from a solution.

Means suitable for freezing droplets include directing the droplets into or near a liquified gas, such as liquid argon or liquid nitrogen to form frozen microdroplets which are then separated from the liquid gas. The frozen microdroplets are then exposed to a liquid or solid non-solvent, such as ethanol, hexane, ethanol mixed with hexane, heptane, ethanol mixed with heptane, pentane or oil.

The solvent in the frozen microdroplets is extracted as a solid and/or liquid into the non-solvent to form a polymer/active agent matrix comprising a biocompatible polymer and a biologically active agent. Mixing ethanol with other non-solvents, such as hexane, heptane or pentane, can increase the rate of solvent extraction, above that achieved by ethanol alone, from certain polymers, such as poly(lactide-co-glycolide) polymers.

A wide range of sizes of sustained release compositions can be made by varying the droplet size, for example, by changing the ultrasonic nozzle diameter. If the sustained release composition is in the form of microparticles, and very large microparticles are desired, the microparticles can be extruded, for example, through a syringe directly into the cold liquid. Increasing the viscosity of the polymer solution can also increase microparticle size. The size of the microparticles which can be produced by this process ranges, for example, from greater than about 1000 to about 1 micrometers in diameter.

Yet another method of forming a sustained release composition, from a suspension comprising a biocompatible polymer and a biologically active agent, includes film casting, such as in a mold, to form a film or a shape. For instance, after putting the suspension into a mold, the polymer solvent is then removed by means known in the art, or the temperature of the polymer suspension is reduced, until a film or shape, with a consistent dry weight, is obtained.

A further example of a conventional microencapsulation process and microparticles produced thereby is disclosed in U.S. Pat. No. 3,737,337, incorporated by reference herein in its entirety, wherein a solution of a wall or shell forming polymeric material in a solvent is prepared. The solvent is only partially miscible in water. A solid or core material is dissolved or dispersed in the polymer-containing mixture and, thereafter, the core material-containing mixture is dispersed in an aqueous liquid that is immiscible in the organic solvent in order to remove solvent from the microparticles.

Another example of a process in which solvent is removed from microparticles containing a substance is disclosed in U.S. Pat. No. 3,523,906, incorporated herein by reference in its entirety. In this process a material to be encapsulated is emulsified in a solution of a polymeric material in a solvent that is immiscible in water and then the emulsion is emulsified in an aqueous solution containing a hydrophilic colloid. Solvent removal from the microparticles is then accomplished by evaporation and the product is obtained.

In still another process as shown in U.S. Pat. No. 3,691,090, incorporated herein by reference in its entirety, organic solvent is evaporated from a dispersion of microparticles in an aqueous medium, preferably under reduced pressure.

Similarly, the disclosure of U.S. Pat. No. 3,891,570, incorporated herein by reference in its entirety, shows a method in which solvent from a dispersion of microparticles in a polyhydric alcohol medium is evaporated from the microparticles by the application of heat or by subjecting the microparticles to reduced pressure.

Another example of a solvent removal process is shown in U.S. Pat. No. 3,960,757, incorporated herein by reference in its entirety.

Tice et al., in U.S. Pat. No. 4,389,330, describe the preparation of microparticles containing an active agent by a method comprising: (a) dissolving or dispersing an active agent in a solvent and dissolving a wall forming material in that solvent; (b) dispersing the solvent containing the active agent and wall forming material in a continuous-phase processing medium; (c) evaporating a portion of the solvent from the dispersion of step (b), thereby forming microparticles containing the active agent in the suspension; and (d) extracting the remainder of the solvent from the microparticles.

Further suitable methods of preparation are described in U.S. Pat. No. 6,194,006 to Lyons et al., U.S. Pat. Nos. 6,110,503, 5,916,598 and U.S. Pat. No. 5,792,477 to Rickey et al. and U.S. Pat. No. 5,650,173 to Ramstack et al. the entire content of all of which is hereby incorporated by reference.

Although the examples below describe a limited number of opioid agonists, it will be understood that any opioid agonist can be used in the methods and formulations described herein.

For example, the opioid agonist morphine can be substituted with other opioid analgesics. Thus, a morphine-equivalent/6β-naltrexol ratio can be maintained in any co-formulation or co-administration method by considering the opioid agonist's potency relative to morphine. Table 1A provides relative potencies of the indicated opioid agonist given orally (unless indicated otherwise). As 10 mg morphine (oral) is a typical dosage of morphine for a 70 kg subject, a "morphine-equivalent dosage" of an opioid agonist for a 70 kg subject is simply a dosage of the opioid agonist that is equivalent to 10 mg of morphine given orally. In Table 1A, the columns "Strength (morphine)" and "Equivalent dosage (10 mg morphine)" provide the relative potency and morphine equivalent dosage of each indicated opioid agonist. For example, a 10 mg morphine dose is equivalent to a 5 mg hydrocodone dose (oral). Since 10 mg morphine is a typical dosage of morphine, 5 mg hydrocodone is the morphine equivalent dosage of hydrocodone. Likewise, 100 mg codeine (oral) is a morphine-equivalent dosage of the opioid agonist codeine for a 70 kg subject.

In addition to the amounts of each particular opioid agonist that equals a morphine-equivalent dosage, Table 1A also provides the oral bioavailability of the particular opioid agonist (this relates to analgesic effects on the CNS, not peripheral effects on the GI tract), and the half-life of the active compound/metabolite. The latter (i.e., the half-life) is important to consider when the oral co-formulation of the opioid agonist with a neutral opioid antagonist (e.g., 6β-naltrexol) is intended to serve as a deterrent for abuse of the opioid agonist. As described herein, when the neutral antagonist has a longer half-life than the opioid agonist it is co-administered with, the neutral antagonist will build-up over time and will eventually accumulate to such an extent that not only will the peripheral effects of the opioid agonist be inhibited (as they are with the initial dose of the opioid agonist/neutral antagonist co-formulation), but even the analgesic (i.e., CNS) effects of the opioid agonist will eventually be inhibited.

TABLE 1A

Opioid comparison

| Opioid Agonist (Opioid Analgesic) given orally unless otherwise indicated | Strength (as compared to morphine) | Equivalent dose (as compared to 10 mg morphine) | Bioavailability for CNS (central) effects | Half-life of active metabolites (hours) |
|---|---|---|---|---|
| Propoxyphene | 1/13 to 1/20 | 130-200 mg | | |
| Codeine | 1/10 | 100 mg | ≈90% | 2.5-3 (C6G (Codeine-6-glucuronide) 1.94) |
| Tramadol | 1/10 | 100 mg | 68-72% | 5.5-7 |
| Anileridine | 1/4 | 40 mg | | |
| Pethidine | 0.36 | 28 mg | 50-60% | 3-5 |
| Hydrocodone | 2 | 5 mg | ≥80% | 3.8-6 |
| Morphine (oral) | (1) | (10 mg) | ≈25% | 2-3 |
| Methadone (acute) | 3-4 | 2.5-3.33 mg | 40-90% | 15-60 |
| Morphine (IV/IM) | 4 | 2.5 mg | 100% | 2-3 |
| Diamorphine (Heroin; IV/IM) | 1.9-4.3 | 2.3-5.2 mg | 100% | <0.6 |
| Hydromorphone | 5 | 2 mg | 30-35% | 2-3 |
| Oxymorphone | 7 | 1.4 mg | 10% | 7.25-9.43 |
| Methadone (chronic) | 7.5 | 1.35 mg | 40-90% | 15-60 |
| Levorphanol | 8 | 1.3 mg | 70% | 11-16 |
| Buprenorphine | 40 | 0.25 mg | 35-40% (sublingual) | 20-70, mean 37 |
| Fentanyl | 50-100 | 0.1-0.2 mg | 33% (oral); 92% (transdermal) | 0.04 (IV); 7 (transdermal) |
| Sufentanil | 500-1,000 | 10-20 μg | | 4.4 |
| Etorphine | 1,000-3,000 | 3.3-10 μg | | |
| Carfentanil | 10,000-100,000 | 0.1-1.0 μg | | 7.7 |

Table 1B below provides additionally the duration of analgesic action of the opioid agonist. This is important to gauge the frequency of oral opioid analgesic dosing, and the expected accumulation of 6β-naltrexol having a blood half-life (t½) of approximately 12 hours.

TABLE 1B

Opioid Potency Comparison

| Opioid Agonist | Administration Route | Time to Effect | Duration | Routine Dosage Equivalent |
|---|---|---|---|---|
| Morphine Sulphate | IV | 5-10 min | 3-6 hours | 10 mg IV |
| Morphine Sulphate | IM | 15-30 min | 3-6 hours | 10 mg IM |

TABLE 1B-continued

Opioid Potency Comparison

| Opioid Agonist | Administration Route | Time to Effect | Duration | Routine Dosage Equivalent |
|---|---|---|---|---|
| Morphine Sulphate | PO | 30-60 min | 3-6 hours | 30-60 mg PO |
| Oxycodone | PO | 10-15 min | 4-6 hours | 10-20 mg PO |
| Hydrocodone | PO | 30-60 min | 4-6 hours | 15-30 mg PO |
| Fentanyl | IV | Immediate | 1-2 hours | 50 micrograms IV |
| Hydromorphone | PO | 15-30 min | 4-6 hours | 7.5 mg |
| Hydromorphone | IV | 15 min | 4-6 hours | 1.5 mg |
| Hydromorphone | IM | 15 min | 4-6 hours | 1.5 mg |
| Codeine | PO | 30-60 min | 4-6 hours | 200 mg |
| Nalbuphine | IM | 15 min | 3-6 hours | 10 mg |

Thus, in some embodiments, the invention provides a co-administration of an opioid agonist (i.e., an opioid analgesic) and a neutral antagonist. In some embodiments, the co-administration is oral administration. In some embodiments, the opioid antagonist and the neutral antagonist are co-formulated together (e.g., in a unit dosage). For example, the co-formulation may be a tablet or a capsule that can be taken orally.

Table 2A provides a list of recommended dosages of an opioid agonist with either 6β-naltrexol or 6β-naltrexamide (to a subject of approximately 70 kg weight).

TABLE 2A

| Opioid analgesic | dosage | 6β-naltrexol | 6β-naltrexamide |
|---|---|---|---|
| morphine | 30-40 mg | 5-10 mg | 10-25 mg |
| morphine | 60-80 mg | 10-15 mg | 15-40 mg |
| oxymorphone | 5-7 mg | 5-10 mg | 10-25 mg |
| hydromorphone | 6-8 mg | 5-10 mg | 10-25 mg |
| oxycodone | 15-30 mg | 5-10 mg | 10-25 mg |
| codeine | 200-400 mg | 5-10 mg | 10-25 mg |
| hydrocodone | 15-20 mg | 5-10 mg | 10-25 mg |
| methadone* | 5 mg | 10 mg* | 10-25 g |

*In the case of methadone, which has a long half-life of 15-60 hours, 6β-naltrexol will not accumulate preferentially. Therefore, abuse deterrence cannot be achieved because 6β-naltrexol has a shorter half-life. (And methadone is prescribed as an opioid maintenance therapy.) As methadone will accumulate more in the body than 6β-naltrexol, the latter can be given in slightly higher dosages.

Likewise, per a morphine-equivalent dosage, the dosage of the opioid analgesic and the neutral antagonist given systemically (e.g., intravenously or subcutaneously) is provided in Table 2B. Note that a dosage administered orally (per oral or p.o.) is also systemic, with the dosage of the opioid analgesic and the neutral antagonist likely to act both from the circulation and the gastrointestinal tract directly; therefore, the oral bioavailability of 6β-naltrexol to reach the circulation is estimated at approximately 25%, while the availability to the gastrointestinal target site may be as high as 50%.

TABLE 2B

| Opioid analgesic (i.e., opioid agonist) | Morphine-equivalent dosage (orally) to a 70 kg subject | 6β-naltrexol dosage (orally) to a 70 kg subject | 6β-naltrexamide dosage (orally) to a 70 kg subject |
|---|---|---|---|
| morphine | 10 mg | 1.5-5 mg | 3-8 mg |
| oxymorphone | 5-7 mg | 1.5-5 mg | 3-8 mg |
| hydromorphone | 6-8 mg | 1.5-5 mg | 3-8 mg |
| oxycodone | 15-30 mg | 1.5-5 mg | 3-8 mg |
| codeine | 200-400 mg | 1.5-5 mg | 3-8 mg |
| hydrocodone | 200-300 mg | 1.5-5 mg | 3-8 mg |
| methadone* | 5 mg | 3-7 mg | 10-26 |

*In the case of methadone, which has a long half-life of 15-60 hours, 6β-naltrexol will not accumulate preferentially. Therefore, abuse deterrence cannot be achieved because 6β-naltrexol has a shorter half-life. (And methadone is prescribed as an opioid maintenance therapy.) As methadone will accumulate more in the body than 6β-naltrexol, the latter can be given in slightly higher dosages.

Note that the dose estimates in Table 2A and Table 2B are designed for treatment of opioid naïve subjects (i.e., subject not previously exposed to the opioid analgesic) upon initiation of analgesic therapy, but not for first dosing of the opioid antagonist to opioid dependent subjects (i.e., subjects who are already addicted to the opioid analgesic). If a neutral opioid antagonist is added to an ongoing opioid analgesic therapy (e.g., after several doses of an opioid analgesic following surgery), to avoid or overcome constipation, and upon prolonged opioid analgesic use, deter abuse liability, the neutral antagonist may be co-administered with the opioid analgesic at approximately two- to threefold lower doses that those stated above in Tables 2A and 2B for 1-2 days (or 1-3) days until the subject is habituated to the neutral opioid antagonist and the full dosage of the neutral opioid antagonist can be administered without adverse effects. For example, if a 70 kg male subject is being currently treated with 6 mg-8 mg of hydromorphone, he may be co-administered 0.75 mg-2 mg 6β-naltrexol for the first 1-2 days, gradually increasing the amount of 6β-naltrexamol until he eventually receives the 1.5 mg-4 mg 6β-naltrexol dosage together with the 6 mg-8 mg hydromorphone dosage as set forth in Table 2A.

Thus, the invention, in some embodiments, provides composition of matter details of a per oral (i.e., orally administered) co-formulation of the opioid agonist morphine and the neutral opioid antagonist 6β-naltrexol on the basis of results in human subjects, obtained under an exploratory Investigational New Drug (eIND) study under the U.S. Food and Drug Administration. On the basis of known relative potencies (see morphine equivalents, Tables 1A and 1B), other opioid analgesics can be included because the morphine dosage can be readily substituted with any other opioid agonist listed in Tables 1A and 1B. Note, however, that in combinations with methadone, oxymorphone, levorphanol, and buprenorphine, the blood half-lives of these opioid agonists are too long for 6β-naltrexol to accumulate preferentially, so that reduction of abuse liability for these opioid agonists appears to be not feasible. Of course, even co-formulations with these opioid agonists (i.e., methadone, oxymorphone, levorphanol, and buprenorphine) and 6β-naltrexol will still enable reduction of peripheral adverse effects.

In some embodiments, the amount of a neutral antagonist is in the formulations (e.g., unit dosage formulations or compositions) and methods described herein is. By "6β-naltrexol equivalent amount" is an amount of a neutral antagonist (that is not an 6β-naltrexol) that is equivalent to an effective amount of 6β-naltrexol. In some embodiments, for an orally administered dose of 10 mg morphine to a 70 kg subject, an effective amount of 6β-naltrexol is 1.5 mg to 5 mg 6β-naltrexol orally administered to a 70 kg subject. In some embodiments, for an orally administered dose of 10 mg morphine to a 70 kg subject, an effective amount of 6β-naltrexol is 1.5 mg to 10 mg 6β-naltrexol orally administered to a 70 kg subject.

Table 3 provides relative potencies of the indicated neutral antagonist given orally (unless indicated otherwise) to a subject who is opioid agonist naïve or a subject who is not dependent upon the opioid agonist. In some embodiments, as 1.5 mg to 5 mg 6β-naltrexol (oral) is a typical dosage of 6β-naltrexol for a 70 kg subject, a 6β-naltrexol equivalent dosage of a neutral antagonist for a 70 kg subject is simply a dosage of the neutral antagonist that is equivalent to 1.5 mg to 5 mg 6β-naltrexol given orally. In some embodiments, as 1.5 mg to 10 mg 6β-naltrexol (oral) is a typical dosage of 6β-naltrexol for a 70 kg subject, a 6β-naltrexol equivalent dosage of a neutral antagonist for a 70 kg subject is simply a dosage of the neutral antagonist that is equivalent to 1.5 mg to 10 mg 6β-naltrexol given orally. In Table 3, the columns "Strength (6β-naltrexol)" and "Equivalent dosage (1.5 mg to 5 mg 6β-naltrexol)" provide the relative potency and morphine equivalent dosage of each indicated neutral antagonist.

TABLE 3

Neutral antagonist comparison

| Neutral Antagonist given orally unless otherwise indicated | Strength (as compared to 6β-naltrexol) | Equivalent dose (as compared to 1.5 mg to 5 mg 6β-naltrexol) | Bioavailability for CNS (central) effects | Half-life of active metabolites (hours) |
|---|---|---|---|---|
| 6β-naltrexol | 1 | 1.5 mg to 5 mg | ~25% | 12 hours |
| 6β-naltrexamine | | 7.5-20 mg | . . . | . . . |
| 6β-naltrexamide | | 3-8 mg | ~25% | Estimated >12 hours |

Additionally, preliminary experiments indicate that 6β-naltrexamide has a longer blood half-life than 6β-naltrexol in mice, and therefore it may substitute for 6β-naltrexol with these opioid agonists with long blood half-lives (e.g., methadone, oxymorphone, levorphanol, and buprenorphine) to reduce abuse liability where needed.

As shown in Tables 1A and 1B, the most potent opioid agonists, sufentanyl, etorphine, carfentanyl, are typically not given orally, but are contemplated within the scope of the invention in oral formulations (including co-formulations with a neutral antagonist). In lieu of 6β-naltrexol, 6β-naltrexamide may be used. As compared to 6β-naltrexol, 6β-naltrexamide has similar properties in animal experiments, with somewhat higher peripheral over central antagonist selectivity (e.g., inhibits GI transit at a lower dosage than the dosage required to inhibit CNS effects), while being somewhat less potent in blocking peripheral effects (2-3 fold lower potency on a mg/kg basis than 6β-naltrexol).

In some embodiments, there are three oral dosage scenarios for 6b-naltrexol. First, to initiate opioid analgesic treatments in non-dependent subjects (e.g., opioid agonist naïve subjects), in some embodiments, a 70 kg subject receiving 10 mg morphine orally (or a morphine equivalent amount of another opioid agonist) may receive 3-5 mg of 6β-naltrexol orally to selectively inhibit the peripheral effects of the morphine (or other opioid agonist) as compared to the lesser inhibition of the central effects of the morphine (or other opioid agonist). Second, in some embodiments (e.g., to prevent abuse liability), a 70 kg subject receiving 10 mg morphine orally (or a morphine equivalent amount of another opioid agonist) may receive 5-10 mg of 6β-naltrexol orally. Third, to subjects who are already being treated with an opioid agonist, 6β-naltrexol may be added. In this embodiment, to add 6b-naltrexol to an opioid agonist dependent subject, initially the 70 kg subject (e.g., being orally administered 10 mg morphine or a morphine equivalent amount of another opioid agonist) may be orally administered 1-2 mg (or 0.75-2 mg) every 3-4 hours for the first 1-2 days, and start oral administration of the full dosage (e.g., 3-5 mg) on the third day.

In some embodiments, if 6β-naltrexol is administered intravenously, the amounts of 6β-naltrexol stated above (for oral administration) may be 2-3 fold lower.

Because naltrexamide (e.g., 6β-naltrexamide) may be 2-3 fold less potent than 6β-naltrexol but may have a longer half-life in the subject, in some embodiments, the amounts of 6β-naltrexol stated above (for oral administration) should be doubled for oral administration of naltrexamide. For example, to initiate opioid analgesic treatments in non-dependent subjects (e.g., opioid agonist naïve subjects), in some embodiments, a 70 kg subject receiving 10 mg morphine orally (or a morphine equivalent amount of another opioid agonist) may receive 6-10 mg of 6β-naltrexamide orally to selectively inhibit the peripheral effects of the morphine (or other opioid agonist) as compared to the lesser inhibition of the central effects of the morphine (or other opioid agonist).

In so embodiments, because naltrexamine (e.g., 6β-naltrexamine) is probably 3-6 times less potent than naltrexol, the amounts of 6β-naltrexol stated above (for oral administration) should be tripled for oral administration of naltrexamime. For example, to initiate opioid analgesic treatments in non-dependent subjects (e.g., opioid agonist naïve subjects), in some embodiments, a 70 kg subject receiving 10 mg morphine orally (or a morphine equivalent amount of another opioid agonist) may receive 9-15 mg of 6β-naltrexamime orally to selectively inhibit the peripheral effects of the morphine (or other opioid agonist) as compared to the lesser inhibition of the central effects of the morphine (or other opioid agonist).

Dosage Considerations for Co-Formulations of Opioid Analgesics and 6β-Naltrexol

Maintenance Dosing and Initiation for Opioid-Naïve Subjects. Opioid analgesics are taken either over a short time period of several days or over long time periods. In both cases, opioid tolerability is expected to be improved by the presence of a peripherally selective antagonist, for example possibly by reducing initial nausea. Also, opioid agonists taken post-surgery may delay recovery of normal bowel functions, which can be avoided with adding 6β-naltrexol. Oral opioid analgesics are typically given as a standard dose, and therefore, we define here a standard dosage range for 6β-naltrexol (and somewhat higher for 6β-naltrexamide and 6β-naltrexamine as outlined in U.S. Pat. No. 6,713,488). This is also understood as a dosage ratio, as the antagonist is competitive at the opioid receptor (higher opioid doses require higher antagonist doses). It is understood that under chronic administration of the co-formulation, clinical experience may dictate somewhat different ratios, as one cannot fully predict the equilibration of antagonist and opioid analgesic in the body and the CNS, while the recommended dose or ratio is fully supported by the eIND results provided below, showing 3 mg 6β-naltrexol iv to block morphine's effect in the GI tract by 50%. In estimating the clinical oral dose of 6β-naltrexol, we consider oral bioavailability into the circulation to be approximately 25%, while direct access to intestinal opioid receptors is likely to contribute also (possibly yielding 30-50% target availability. Hence, a 5 mg oral dose (together with 40 mg morphine or equivalent) may be equivalent to a 2.5 mg dose of 6β-naltrexol given iv. As the duration of action of orally administered morphine ranges between 4-6 hours (similar to other oral opioid analgesics (see Table 1B), we anticipate daily intake of 3-10 doses, bringing the cumulative 6β-naltrexol dose to 15-50 mg per day, sufficient to fully block peripheral opioid effects, but insufficient to cause CNS inhibition (at 25% bioavailability to the circulation, 4-12 mg will reach the systemic circulation). If a 10 mg dose of 6β-naltrexol (together with 40 mg morphine or equivalent) is selected, suppression of analgesia is still not expected. However, upon more frequent administration under abuse conditions (i.e., abuse of the morphine or other equivalent opioid agonist), 6β-naltrexol will accumulate to such high levels that the 6β-naltrexol will enter the CNS and start inhibiting the CNS effects of the opioid agonist. In a subject weighing approximately 70 kg, 10 mg 6β-naltrexol is equivalent to approximately 0.14 mg/kg.

Depending on the degree of slow equilibration with the CNS, the exact 6β-naltrexol dose remains to be tested clinically but will be close to this range. Some tolerance is anticipated to occur, such that the dose of morphine needs to be increased or given more often. Depending on the degree of tolerance (which can vary between subjects), and because the opioid analgesic does not accumulate appreciably while 6β-naltrexol does, 6β-naltrexol should be added to the co-formulation at the lower range of the recommended dose (~5 mg per 40 mg morphine). It is noted that tolerance at opioid receptors appears to be minimal in the GI tract so that increasing doses of morphine can cause increasing GI problems that need to be treated.

Similar dosage ratios apply to sustained release formulation, in particular if the rate limiting step is the rate of absorption rather than the rate of elimination. Both opioid analgesic and antagonist will accumulate to steady state at a rate inversely related to their respective half-lives, with steady state levels also inversely related to rate of elimination, resulting in relatively higher antagonist steady state levels (see FIG. 20). The dose of 6β-naltrexol delivered per day should not exceed 20 mg.

Initiation of Antagonist Protection Therapy in Opioid Dependent Subjects. During the course of treatment with opioid analgesics, dependence develops rapidly. Dependent subjects are exquisitely sensitive to conventional opioid antagonists, such as naltrexone and naloxone. In the eIND study with methadone-dependent subjects described below, 0.050 mg naloxone produced detectable withdrawal symptoms (CNS related), while 0.5 mg naloxone will elicit both severe CNS and peripheral withdrawal (peripheral: e.g., diarrhea and cramping), a hallmark of naloxone's action as an inverse agonist. In contrast, 0.5 mg 6β-naltrexol given i.v. caused a near normal bowel movement with minimal peripheral withdrawal and no detectable CNS withdrawal (see Table 5A and 5B, below), showing high sensitivity in restoring normal functions with few adverse effects at this dose. While 3 of 4 subjects did tolerate 1 mg 6β-naltrexol i.v. rather well, one subject had sufficiently strong reactions at 0.5 mg not to progress to the 1 mg 6β-naltrexol dose. Thus, in some embodiments, the neutral antagonist 6β-naltrexol should be titrated initially in doses of 0.75-2 mg given orally, every 3-4 hours, until a GI reaction occurs (bowel movement or first sign of cramping). Then, in some embodiments, 1-2 mg oral 6β-naltrexol doses should be maintained every 6 hours for 1-2 days (or possibly 1-3 days), before the co-formulation is given with full doses of 6β-naltrexol (e.g., 1.5-5 mg to selectively inhibit peripheral effects of the opioid agonist as compared to the inhibition of the central effects of the opioid agonist, or 5-10 mg to deter abuse liability to the opioid agonist).

Effect of 6β-Naltrexol on Hydrocodone-Induced Antinociception

Previous work in animals confirms that 6β-naltrexol antagonizes the central effects of opioids at sufficiently high doses. For example, research by Wang D, Raehal K M, Bilsky E J, Sadee W. (2001 June) "Inverse agonists and neutral antagonists at mu opioid receptor (MOR): possible role of basal receptor signaling in narcotic dependence," *J Neurochem.*; 77(6): 1590-600 showed that 6β-naltrexol reverses morphine-induced antinociception when administered intraperitoneally. Other experiments have further shown that 6β-naltrexol prevents the stereotypic circling induced by morphine in non-dependent and chronically dependent mice (Wang D., Raehal K. M., Lin E. T., Lowery J. J., Kieffer B. L., Bilsky E. J., Sadee W. (2004 February Epub 2003 Nov. 4) "Basal signaling activity of mu opioid receptor in mouse brain: role in narcotic dependence," *J Pharmacol Exp Ther.*; 308(2): 512-20; Raehal K. M., Lowery J. J., Bhamidipati C. M., Paolino R. M., Blair J. R., Wang D., Sadee W., Bilsky E. J. (2005 June; Epub 2005 Feb. 16) "In vivo characterization of 6β-naltrexol, an opioid ligand with less inverse agonist activity compared with naltrexone and naloxone in opioid-dependent mice," *J Pharmacol Exp Ther* 313(3):1150-62).

Experimental Data Demonstrates that 6β-Naltrexol Reverses Hydrocodone-Induced Antinociception.

EXAMPLE 1

Tail-Flick Assay. Antinociception was assessed using a 55° C. warm-water tail-flick assay (Bilsky E. J., Qian X., Hruby V. J., Porreca F. (2000 April) "Antinociceptive activity of [β-methyl-2',6'-dimethyltyrosine(1)]-substituted cyclic [D-Pen(2), D-Pen(5)]Enkephalin and [D-Ala(2),Asp(4)]Deltorphin analogs," *J Pharmacol Exp Ther*; 293(1):151-8; Raehal K. M., Lowery J. J., Bhamidipati C. M., Paolino R. M., Blair J. R., Wang D., Sadee W., Bilsky E. J. (2005 June; Epub 2005 Feb. 16) "In vivo characterization of 6β-naltrexol, an opioid ligand with less inverse agonist activity compared with naltrexone and naloxone in opioid-dependent mice," *J Pharmacol Exp Ther* 313(3):1150-62). Male ICR mice (UNE) or CD-1 mice (Charles River) 25-40 grams were used in all procedures. Mice were weighed and the tails marked with indelible ink, with an n size of 8-10 mice/group. The latency to the first sign of a rapid tail-flick was used as the behavioral endpoint (Jannsen et al., 1963). Briefly, each mouse was tested for baseline latency by immersing the distal third of its tail into the water bath and recording the time until a vigorous tail-flick response to the noxious stimulus. Latencies typically averaged between 1.5 and 2.5 s in drug naïve subjects with any mice having a baseline latency greater than 5 s eliminated from further testing. Upon completion of baseline testing mice were injected and retested for tail-flick latencies at various times after injection (typically 10, 20, 30, 45, 60, 90, 120 and 180 minutes or until the test latency approaches the baseline latency, e.g., less than 20% MPE for the group). A maximal score was assigned to mice not responding within 10 s to avoid tissue damage. The percentage of antinociception was calculated as (test latency−baseline latency)/(10−baseline latency)*100.

Antinociception Studies for Determining Time of Peak Effect of 6β-Naltrexol.

Figure 1B:
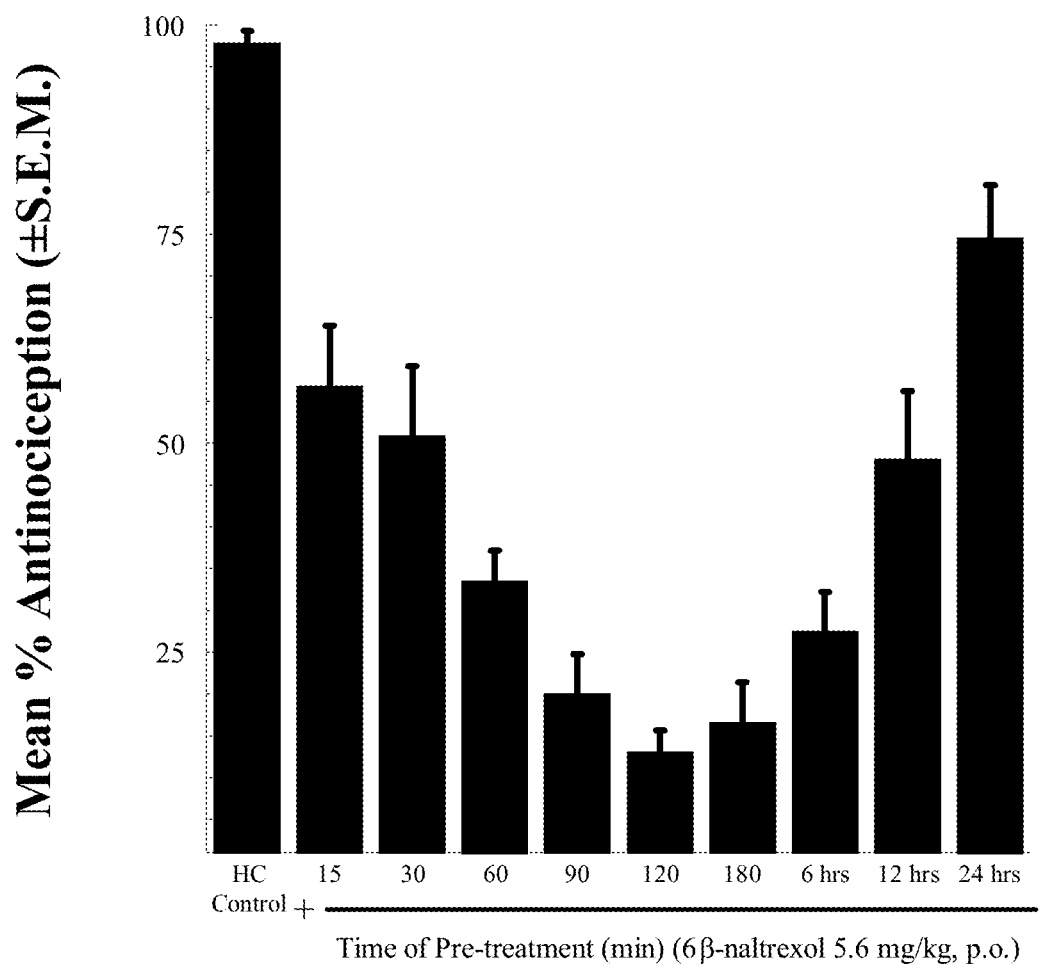
FIG. 1B is a graph that shows data reflecting the duration of the inhibitory effects of orally-administered 6β-naltrexol on an antinociceptive, intravenous dose of hydrocodone, and demonstrates the time of peak effect of antinociception inhibition in mice.

The duration of 6β-naltrexol effects was measured by pretreating mice with 6β-naltrexol at various times prior to an injection of an antinociceptive $A_{90}$ dose of hydrocodone (3.2 mg/kg, i.v., dose determined previously; data not shown). Mice were tested 10 min later at the time of peak effect for hydrocodone in the tail-flick assay. 6β-naltrexol doses of 0.56 mg/kg for i.v. administration (FIG. 1A) and 5.6 mg/kg for p.o. administration (FIG. 1B) were used.

These time ranging experiments illustrated that 6β-naltrexol was capable of reversing the centrally mediated antinociceptive effects of hydrocodone (FIGS. 1A and 1B), with a time of peak effect at 90 min for i.v. administration and 120 min when administered p.o. (per oral).

Antinociception Studies for Determining Antagonist Potencies.

Figure 2A:
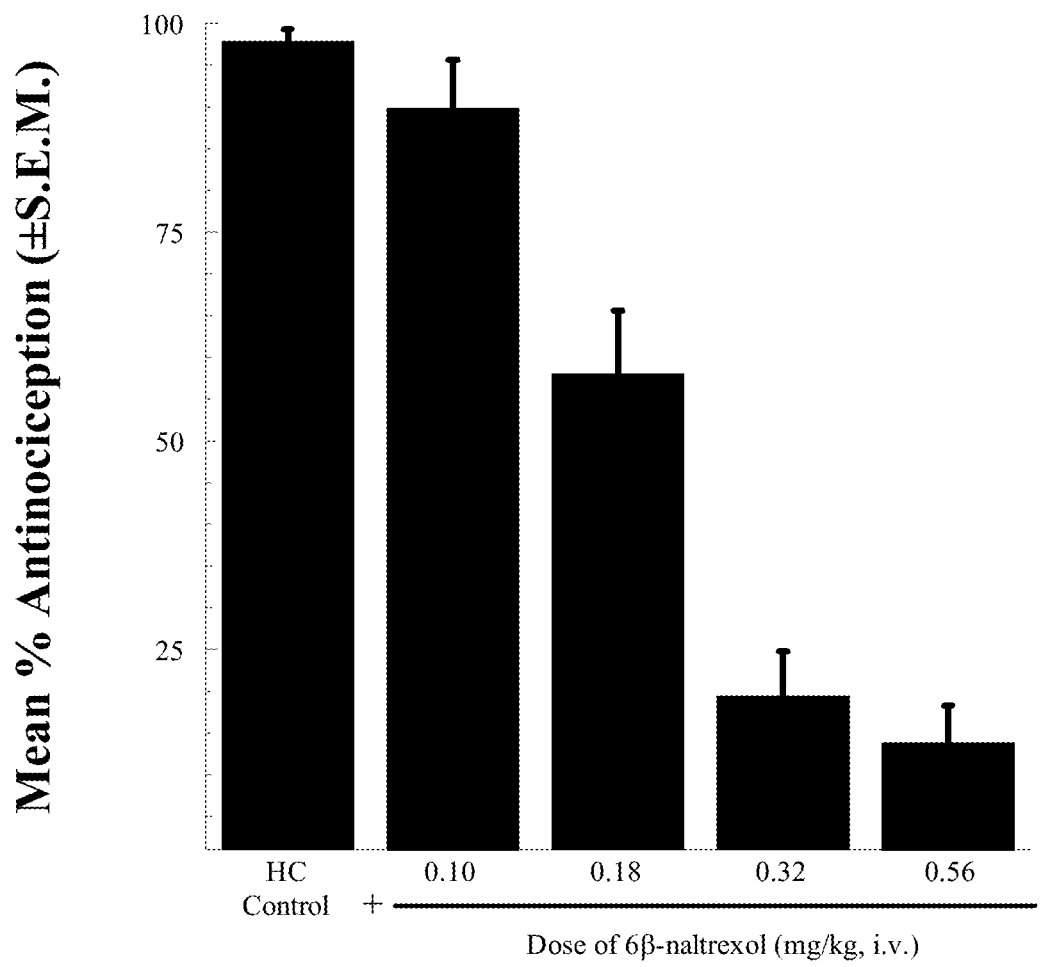
FIG. 2A is a dose response curve reflecting the potency of the inhibitive effects of intravenously-administered 6β-naltrexol on an antinociceptive, intravenous dose of hydrocodone in mice.
Figure 2B:
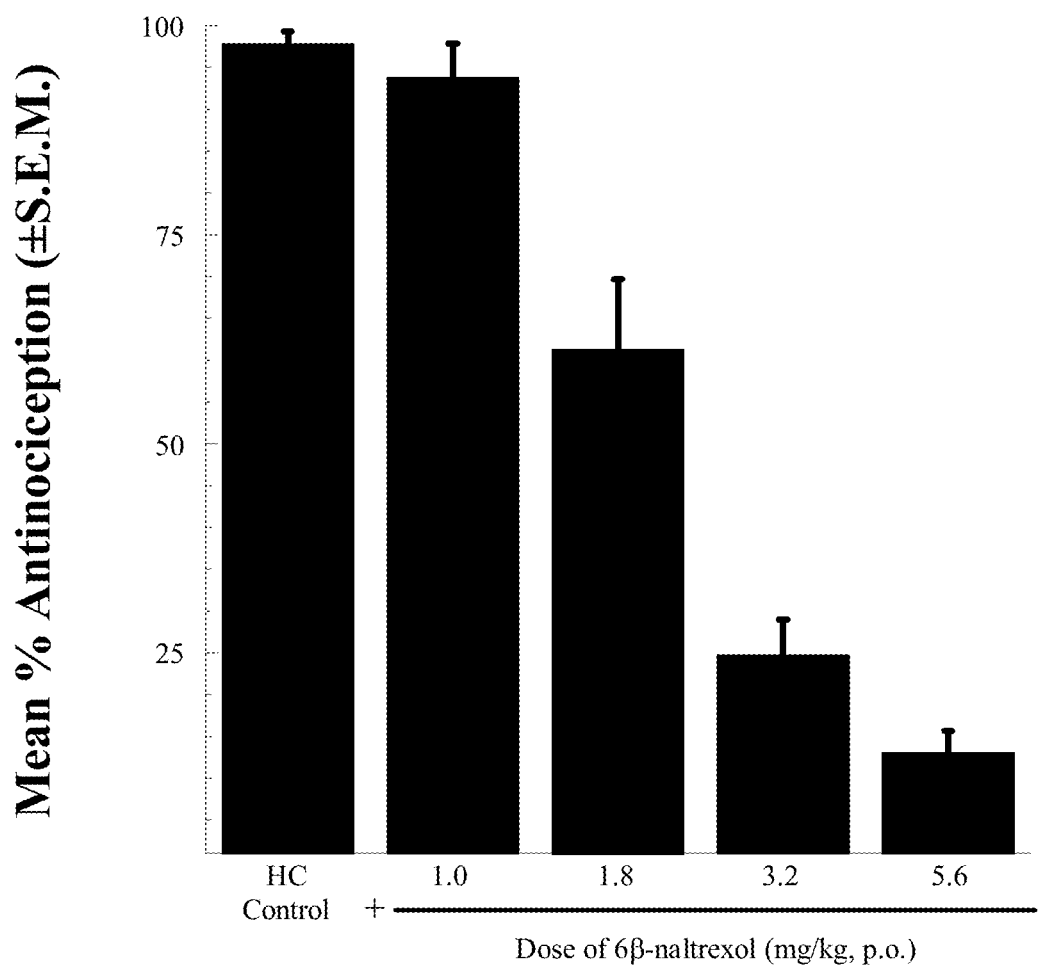
FIG. 2B is a dose response curve reflecting the potency of the inhibitive effects of orally-administered 6β-naltrexol on an antinociceptive, intravenous dose of hydrocodone.

Both oral and i.v. potencies were determined by administering vehicle or various doses of 6β-naltrexol at appropriate times prior to an $A_{90}$ dose of hydrocodone (3.2 mg/kg, i.v.). The respective i.v. and p.o. pretreatment times were 90 min (FIG. 2A) and 120 min (FIG. 2B). Mice were tested 10 min post hydrocodone injection (time of hydrocodone peak effect) in the 55° C. tail-flick assay. At least three doses were tested to produce a dose-response curve. The percent antinociception was then calculated for each dose and compared to hydrocodone controls.

These dose response curves were used to determine $ID_{50}$ value for 6β-naltrexol. The percentage of inhibition or reversal of the hydrocodone-induced antinociception was calculated as (test−hydrocodone control)/(saline control−hydrocodone control)*100. From this data an $ID_{50}$ value (and 95% confidence interval) was calculated for each route using linear regression (FlashCalc software; Dr. Michael Ossipov, University of Arizona, Tucson, Ariz.). $ID_{50}$ values for 6β-naltrexol inhibition of hydrocodone-induced antinociception were determined to be 0.222 mg/kg (95% CI=0.194-0.253) for i.v. administration, and 2.35 mg/kg (95% CI=2.11-2.63) for oral administration, consistent with this compound's 14% bioavailability in the rodent (previously determined data not shown).

Antinociception Studies for Oral Co-Administration. The tail-flick assay was used to construct full dose- and time-response summaries for 6β-naltrexol in combination with hydrocodone. Vehicle or various doses of 6β-naltrexol were orally co-administered with an $A_{90}$ dose of hydrocodone (32 mg/kg, p.o.) determined previously (data not shown) at t=0 min. Tail-flick latencies were determined at t=10, 20, 30, 45, 60, 90, 120 and 180 minutes post injection (or until 20% MPE was reached) and % antinociception was calculated for each mouse (FIG. 3).

Figure 3:
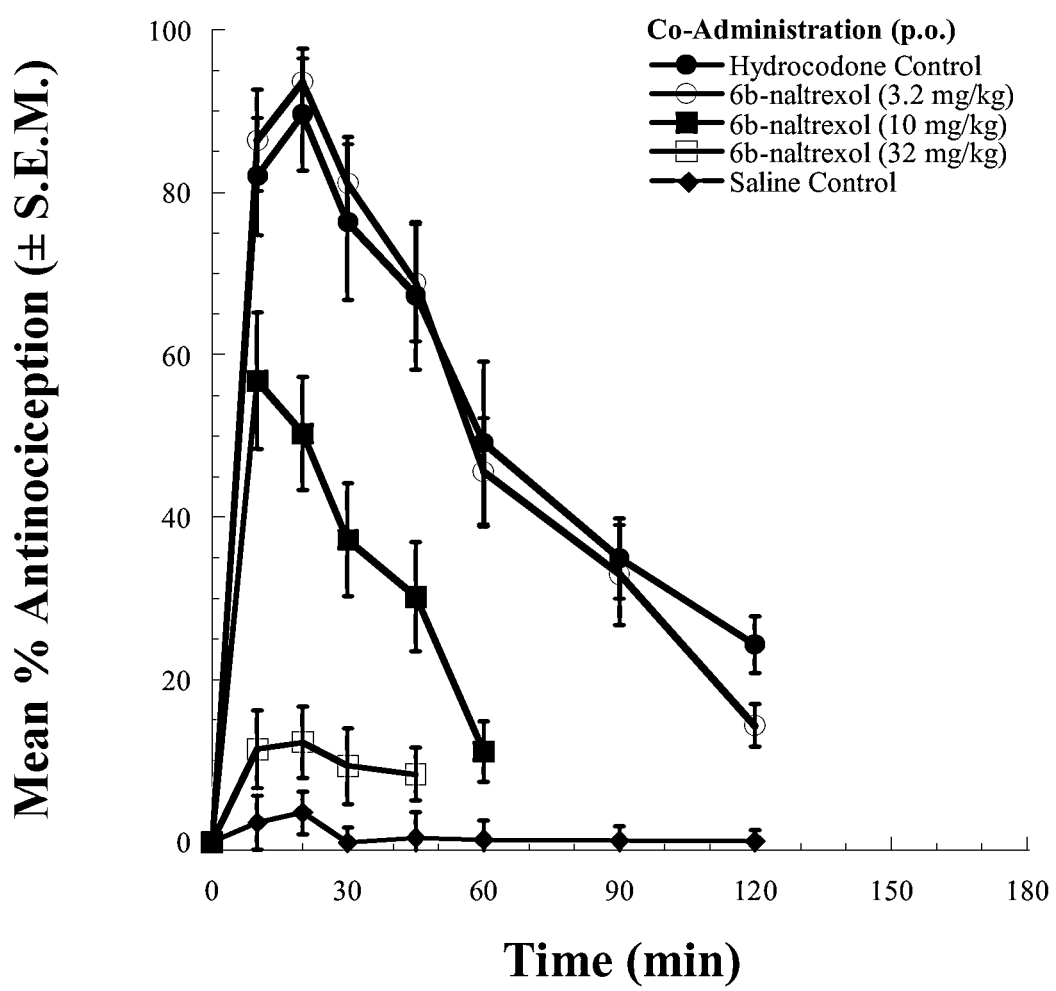

The antinociception experiments shown in FIG. 3 yield an $ID_{50}$ value of 12.3 mg/kg (95% CI=10.4-14.7) for 6β-naltrexol co-administered with hydrocodone.

The experiments shown in FIGS. 1-3 demonstrate that 6β-naltrexol blocks hydrocodone-induced antinociception regardless of the route of administration.

Effect of 6β-Naltrexol on Hydrocodone-Induced Gastrointestinal Tract Slowing

EXAMPLE 2

GI Transit Assay. Opioid-induced GI inhibition was measured using a standard protocol (Current Protocols in Pharmacology, number 5.3). Male CD-1 mice (Charles River) 25-40 grams are used in all procedures. Mice are weighed and the tails marked with indelible ink, with an n size of 8-10 mice/group. Mice were deprived of food for approximately 18 hr prior to the start of the experiment. 6β-naltrexol or saline was injected at 1 ml/100 g bodyweight (route and pretreatment time vary) prior to an oral delivery of a charcoal suspension (constant volume of 250 μL). At t=0 minutes, the oral charcoal is delivered using an 18 gauge curved gavage needle (Popper & Sons) on a 1 cc syringe. The suspension is made the day of use at 10% charcoal (100-400 mesh) with 2.5% arabic acid in distilled water and mixed thoroughly and repeatedly to minimize needle obstruction. Animals were sacrificed 30 min after administration of the charcoal meal by light ether anesthesia followed by cervical dislocation. The small intestine (duodenum to cecum) was dissected out and carefully uncoiled. The distance covered by the charcoal was measured and compared to the total length of the small intestine for each animal. The mean percent transit was then calculated as (distance covered by the charcoal)/(total length of the small intestine)*100.

Figure 4A:
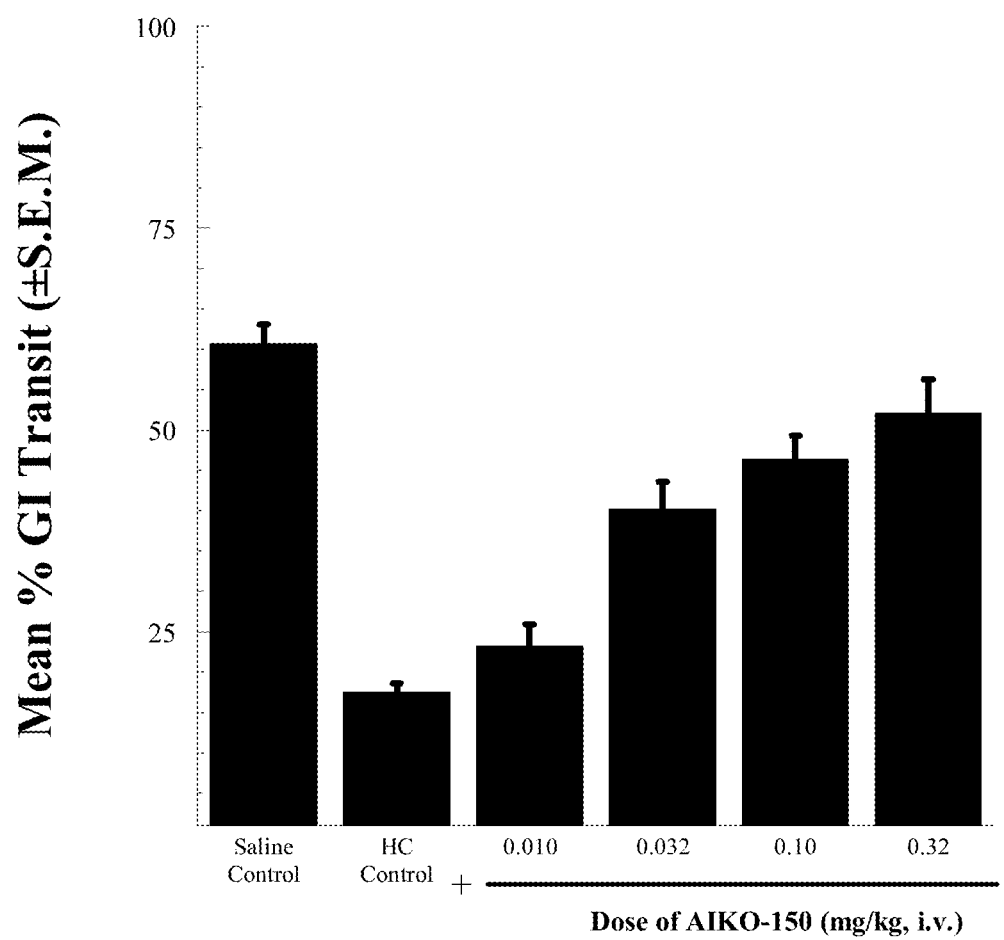
FIG. 4A is a dose response curve reflecting the potency of intravenously-administered 6β-naltrexol to reverse hydrocodone-induced GI transit slowing, where the two compounds are not co-administered.
Figure 4B:
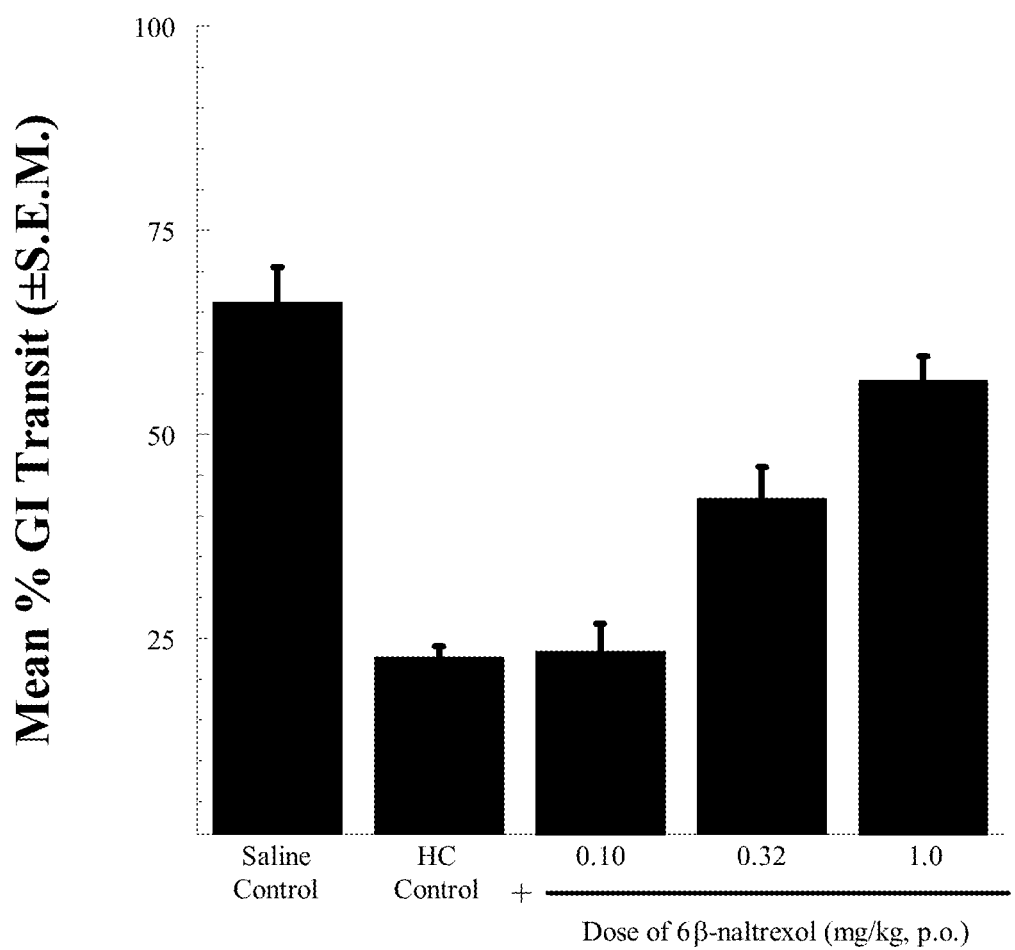
FIG. 4B is a dose response curve reflecting the potency of orally-administered 6β-naltrexol to reverse hydrocodone-induced GI transit slowing, where the two compounds are not co-administered.

GI Transit Studies for Determining 6β-Naltrexol Potency. The ability of 6β-naltrexol to block hydrocodone induced GI inhibition was assessed. Both i.v. (FIG. 4A) and oral potencies (FIG. 4B) were determined by administering vehicle or various doses of 6β-naltrexol prior to an antinociceptive $A_{90}$ dose of hydrocodone (3.2 mg/kg, i.v.). The pretreatment times corresponded with the time of peak effect for the antinociception studies. The charcoal meal was given 10 min following the injection of hydrocodone. Vehicle (saline) controls were also assessed i.v. The percentage of GI transit was calculated for each mouse and a dose-response curve was constructed for the antagonist. At least three doses were used for each route and the results were compared to saline and hydrocodone controls.

$ID_{50}$ values were calculated for 6β-naltrexol to determine potency to inhibit hydrocodone effects. 6β-naltrexol and hydrocodone were administered at appropriate times so that time of peak effect (as determined in the tail-flick assay) occurred during charcoal administration. 6β-naltrexol dose-dependently reversed the inhibition of GI transit by hydrocodone ($A_{90}$ dose, i.v.), yielding $ID_{50}$ values of 0.0443 mg/kg (95% CI=0.0275-0.0713) and 0.410 (95% CI=0.310-0.543) mg/kg for i.v. and p.o. (FIGS. 4A and 4B) administration, respectively.

Figure 5:
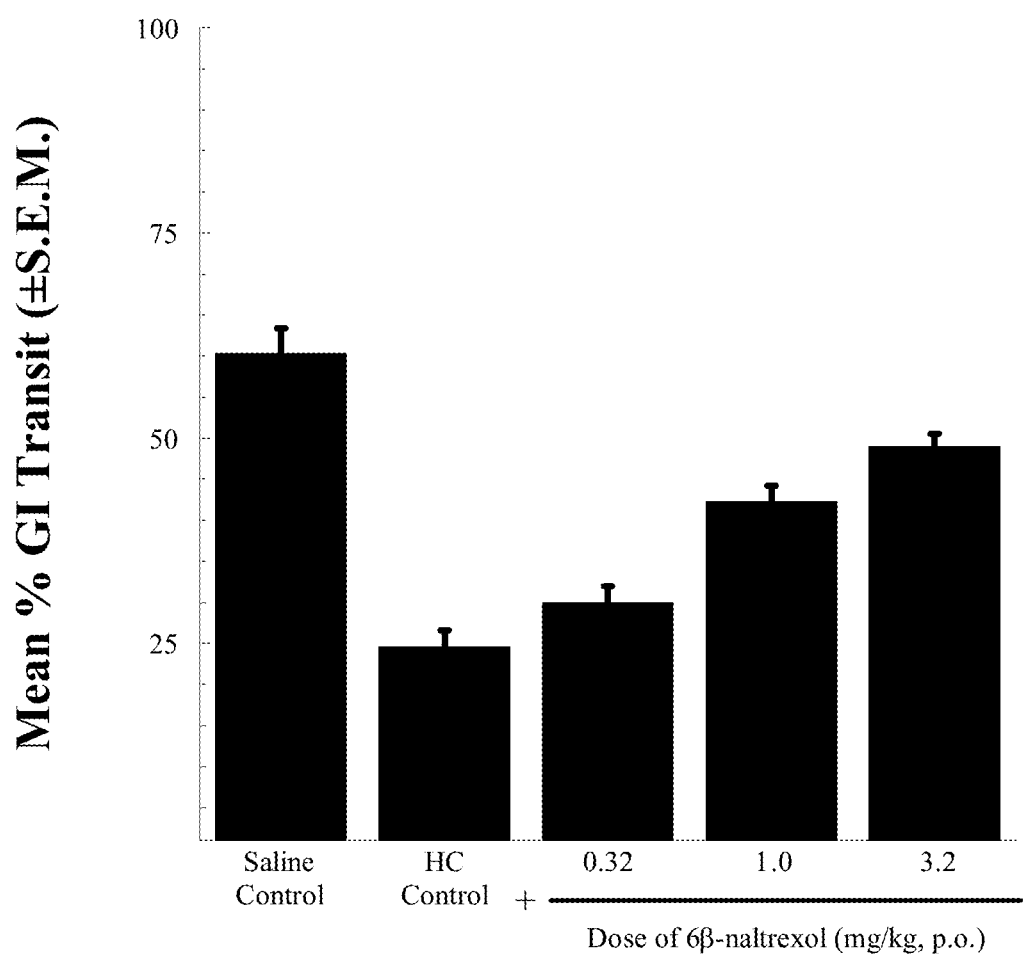

GI Transit Studies for Oral Co-Administration. Vehicle (saline) or various doses of 6β-naltrexol were orally co-administered with an antinociceptive $A_{90}$ dose of hydrocodone (32 mg/kg, p.o.) 60 min prior to charcoal administration (FIG. 5). This time was chosen so that the time of peak effect for the antagonist would occur during intestinal transit of the charcoal meal. Vehicle (saline) controls were also assessed p.o. to compare the observed effects to opioid naïve mice. The percentage of GI transit was calculated for each mouse and a dose-response curve was constructed. At least three doses were used and the results were compared to saline and hydrocodone controls. 6β-naltrexol again dose-dependently reversed GI inhibition (FIG. 5) with an $ID_{50}$ of 1.290 mg/kg (95% CI=0.990-1.68).

Statistical Analysis. The dose-response curves shown in FIG. 2-5 were used to estimate and compare central (antinociception) to peripheral (GI transit) potencies of 6β-naltrexol. The percentage of inhibition or reversal of the hydrocodone effect in either assay was determined for each mouse in the antagonist groups. The percent reversal was calculated as (test−hydrocodone control)/(saline control−hydrocodone control)*100. From this data an $ID_{50}$ value (and 95% confidence interval) was calculated for each route/antagonist/assay using linear regression (FlashCalc software; Dr. Michael Ossipov, University of Arizona, Tucson, Ariz.).

Potency of 6β-Naltrexol for Slowing GI-Transit and for Reversing Antinociception.

Figure 6A:
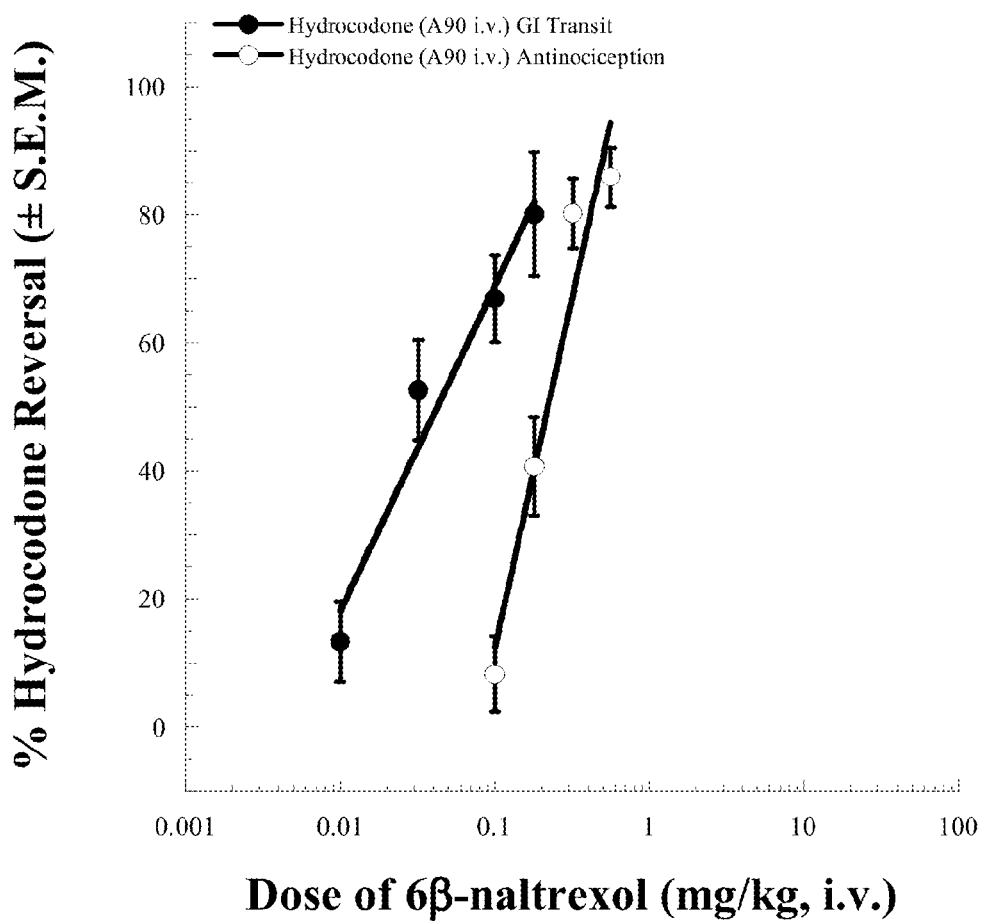
FIG. 6A shows the summarized potency data for inhibition of hydrocodone activity by 6β-naltrexol in GI transit studies (peripheral effects) and antinociception studies (central effects), where both 6β-naltrexol and hydrocodone were administered intravenously.
Figure 6B:
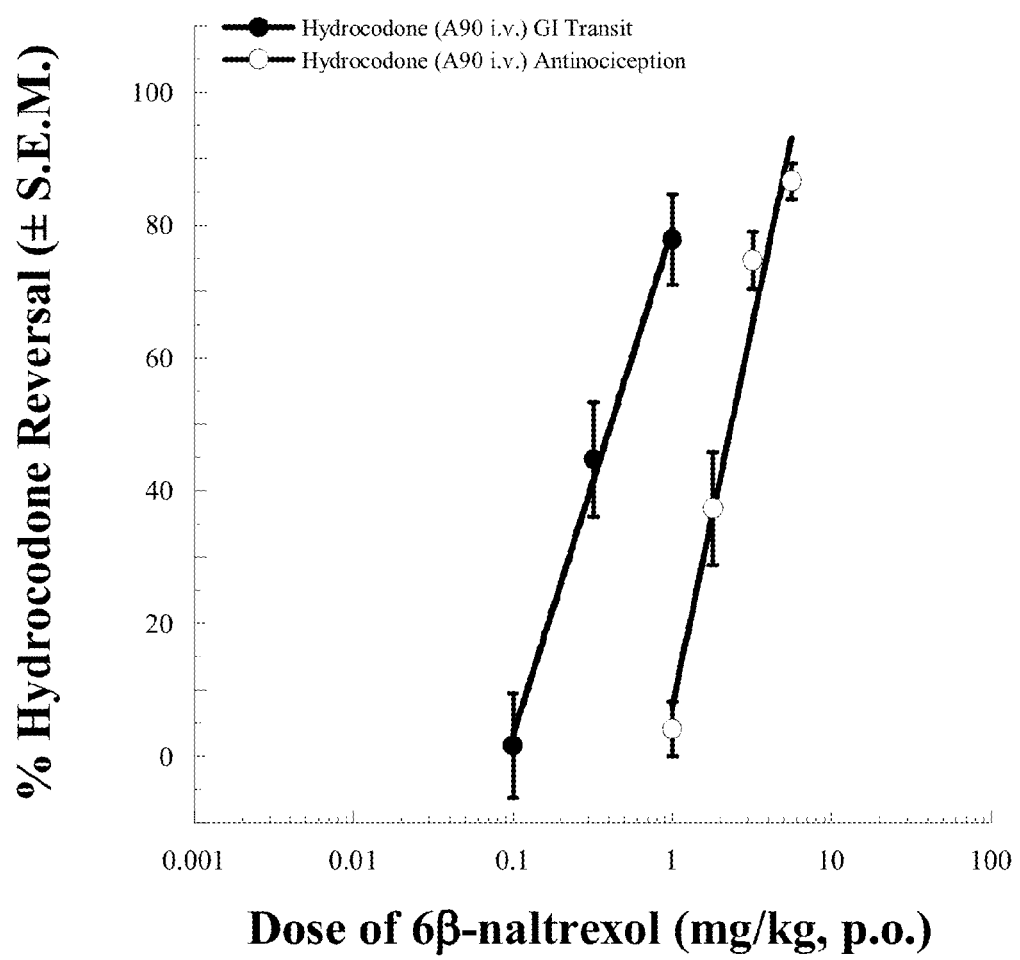
FIG. 6B shows the summarized potency data for inhibition of hydrocodone activity by 6β-naltrexol in GI transit studies (peripheral effects) and antinociception studies (central effects), where 6β-naltrexol was administered orally and hydrocodone was administered intravenously.
Figure 6C:
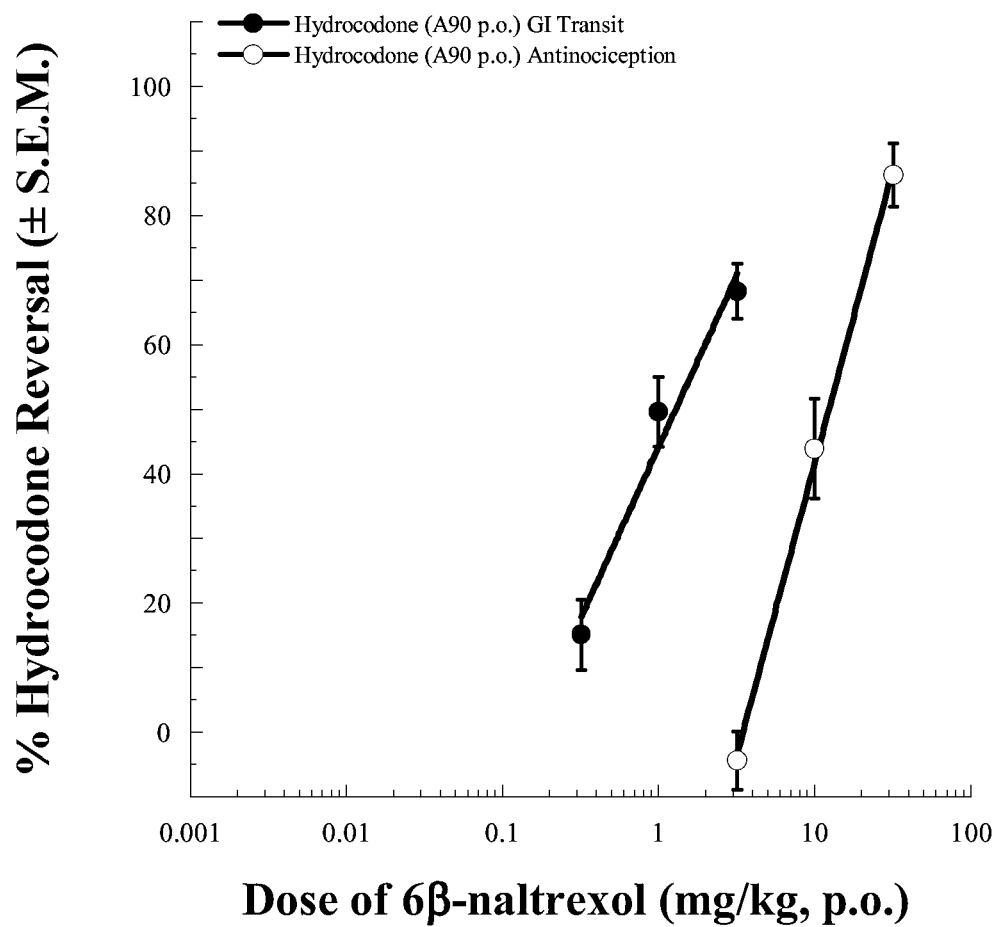
FIG. 6C shows the summarized potency data for inhibition of hydrocodone activity by 6β-naltrexol in the GI transit studies (peripheral effects) and antinociception studies (central effects) where both 6β-naltrexol and hydrocodone were orally co-administered.

Comparison of the calculated potencies ($ID_{50}$) for 6β-naltrexol to reverse either the central effects, antinociception, or peripheral effects, GI-transit slowing, induced by hydrocodone, led to the surprising discovery that 6β-naltrexol is 5-10-fold more potent peripherally than centrally. FIGS. 6A-C demonstrate this potency difference showing data derived from the dose response curves described above.

6β-naltrexol was found to have significant shifts in potency between the two assays for all administration parameters (FIGS. 6A-C). Both i.v. (FIG. 6A) and p.o. (FIG. 6B) administration of 6β-naltrexol were approximately 5-times more potent at reversing GI effects of i.v. hydrocodone than antinociceptive effects (Table 1A). Furthermore, oral co-administration with hydrocodone resulted in a 9.53-fold shift in potency (FIG. 6C, Table 1A). These data suggest that 6β-naltrexol is more potent at inhibiting peripheral effects than central effects induced by opioids.

Calculations of $ID_{50}$ potencies from these data further suggest that 6β-naltrexol is 9.5-fold more potent for slowing GI-transit than for reversing antinociception when both drugs are administered orally, as would be utilized for therapeutic use (Table 4).

These results indicate that there is a therapeutic window of effectiveness for 6β-naltrexol where peripheral side effects of opioid use are reduced without inhibition of analgesia. In the case of orally co-administered 6β-naltrexol and hydrocodone, that therapeutic window occurs when 6β-naltrexol is administered to a mouse from 0.1-3.0 mg/kg (FIG. 6C).

Table 4 shows the fold-shift in peripheral vs. central potency as calculated from the data presented in FIG. 6A-C and is shown as (antinociception $ID_{50}$)/(GI transit $ID_{50}$). (A fold-shift less than 1.0 indicates a greater central potency over peripheral potency.)

TABLE 4

| Drug Combination | GI Transit $ID_{50}$ (95% CI) (mg/kg) | Antinociception $ID_{50}$ (95% CI) (mg/kg) | Fold-Shift |
|---|---|---|---|
| 6β-naltrexol (i.v.)/ Hydrocodone (i.v.) | 0.0443 (0.0275-0.0713) | 0.222 (0.194-0.253) | 5.01 |
| 6β-naltrexol (p.o.) Hydrocodone (i.v.) | 0.410 (0.310-0.543) | 2.35 (2.11-2.63) | 5.73 |
| 6β-naltrexol (p.o.)/ Hydrocodone (p.o.) | 1.290 (0.990-1.68) | 12.3 (10.4-14.7) | 9.53 |

This therapeutic window is surprising because it diverges dramatically from the ratios postulated by Simon in United States Patent Application 2004/0024006 A1. Our data also demonstrate that use of the dosages postulated by Simon (see United States Patent Application 2004/0024006 A1 at paragraphs [107] and [155]) would either have no effect (in the case of paragraph [107]) or have the unwanted effect of reversing antinociception (in the case of paragraph [155]).

The mouse data can be extrapolated to provide for effective formulation for humans. The 0.1-3.0 mg/kg mouse suggests a Human Equivalent Dose (HED) of 0.0081-0.243 mg/kg. This calculation is based on a body surface area calculation published in FDA guidelines for Estimating the Safe Starting Dose in Clinical Trials for Therapeutics in Adult Healthy Volunteers, available on Aug. 16, 2007 at www.fda.gov/cber/gdlns/dose.htm. If this dose is applied to a 70 kilo human, the human subject would need between 0.567-17.0 mg to have the desired effect of relieving GI transit slowing without inhibiting analgesia. A person skilled in the art could predict and conduct clinical testing to confirm similar pharmacokinetics in humans and determine the absolute correct dosage.

It should be noted that the concentrations required to reverse the antinociceptive effects of hydrocodone are consistent with the human blood levels of 6β-naltrexol obtained after standard naltrexone treatment for alcohol or opioid addiction maintenance where blocking the central effect is intended. Typically, a minimum dose of 50 mg naltrexone is administered daily to a human patient. The human must be opioid-free so there are no compounding effects on GI slowing or drug interactions altering pharmacokinetics or absorption. The literature teaches that approximately 43% of naltrexone is converted to 6β-naltrexol (for examples, see: Cone, E J, Gorodetzky C W, and Yea S Y (1974) "The Urinary Excretion Profile of Naltrexone and Metabolites in Man," Drug Metab and Disp 2(6): 506-512; ReVia™ Label; Wall M. E., Brine D. R, Perez-Reyes M. (1981) "Metabolism and Disposition of Naltrexone in Man after Oral and Intravenous Administration, Drug Metabolism and Disposition" *Drug Metabolism and Disposition,* 9(4):369-375; Verebey K. (1980) "The Clinical Pharmacology of Naltrexone: Pharmacology and Pharmacodynamics," *Naltrexone: NIDA Research Monograph,* 28, R E Willette and G Barnett, eds. pp 147-158; Wall M. E., Brine D. R., Perez-Reyes M. (1980) "The Metabolism of Naltrexone in Man," *Naltrexone: NIDA Research Monograph,* 28, R E Willette and G Barnett, eds. pp 105-131; Perez-Reyes M. and Wall M. E. (1980) "A Comparative Study of the Oral, Intravenous, and Subcutaneous Administration f 3h-Naltrexone to normal male volunteers," *Naltrexone: NIDA Research Monograph* 28, R E Willette and G Barnett, eds. pp 93-101), meaning humans are exposed to 20 mg of 6β-naltrexol following such a dose. Given that human dosages are determined for a standard 70 kg person, persons are routinely exposed to >0.3 mg 6β-naltrexol/kg body weight daily and often much higher dosages and blood levels are utilized. As such, there is evidence that this treatment level is safe in humans (for examples, see: Dunbar J. L., Turncliff R. Z., Dong Q., Silverman B. L., Ehrich E. W., Lasseter K. C. (2006) "Single- and Multiple-Dose Pharmacokinetics of Long-acting Injectable Naltrexone," *Alcohol: Clin and Exper Res.* 30(3):480-490; Jayaram-Lindstrom N., Wennberg P., Beck O., Franck J. (2005) "An open clinical trial of naltrexone for amphetamine dependence: Compliance and tolerability," *Nord J Pschy* 59(3):167-171; Brewer C. and Wong V. S. (2004) "Case Report. Naltrexone: report of lack of hepatotoxicity in acute viral hepatitis, with a review of the literature," *Addict Bio* 9, 81-87). However, the levels of 6β-naltrexol attained after administration of 6β-naltrexol itself or as a metabolite of naltrexone may not be equivalent if the metabolic conversion occurs in part in the brain; 6β-naltrexol given directly shows surprisingly low access to the brain compared to naltrexone.

Substantially Longer Retention of 6β-Naltrexol and 6β-Naltrexamide in Plasma and Brain Tissue after i.p Injection in Mice Compared to Naltrexone.

EXAMPLE 3

Some of these effects are mediated in part or fully by peripheral opioid receptors, that are identical to those in the brain but may undergo different regulation (for example intestinal opioid receptors are thought not to undergo tolerance).

This study shows crude pharmacokinetics of 6β-naltrexol and 6β-naltrexamide in mouse plasma and brain (the naltrexol data were published in Wang et al. 2004; the naltrexamide data were not published) compared with naltrexone. Mice were injected i.p. with 1 mg/kg naltrexone, 1 mg/kg 6β-naltrexol, 1 mg/kg 6β-naltrexamide, 10 mg/kg 6β-naltrexol or 10 mg/kg 6β-naltrexamide and sacrificed after 10 or 60 min. Blood samples and whole brain were collected. Samples were analyzed for the presence of the antagonists using mass spectrometry.

Naltrexone, 6β-naltrexol and 6β-naltrexamide were extracted from plasma or brain tissue homogenates, measured by liquid chromatography/mass spectrometry/mass spectrometry (LC/MS/MS), using APCI/positive ionization. Nalbuphine served as the internal standard. The method was sensitive to approximately 1 ng/mL (g) (3-4 nM). 6β-Naltrexol was detectable in plasma but not brain tissue after the naltrexone dose (1.9 ng/mL and 1.7 ng/mL after 10 and 60 min, respectively). In contrast, no naltrexone was detectable after administration of 6β-naltrexol. The concentrations of two compounds in each row of the table represent the injected parent drug only. Mean±SD, n=3.

As shown, similar brain levels were achieved with equipotent analgesic doses of naltrexone and 6β-naltrexol or 6β-naltrexamide (1 mg/kg and 10 mg/kg, respectively). Surprisingly, after 60 min, the levels of 6β-naltrexol and 6β-naltrexamide had not changed from those measured at 10 min, whereas the levels of naltrexone declined nearly 90% by 60 min. This indicates a substantially longer retention in plasma and particularly in brain for 6β-naltrexol and 6β-naltrexamide than for naltrexone. These data can be extrapolated to suggest a substantially longer half-life for 6β-naltrexol and 6β-naltrexamide than that of opioid agonists such as naltrexone, in general. In humans the half-life of naltrexone is 4 hours, while that of 6β-naltrexol is 1215 hours. Importantly, both 6β-naltrexol and 6β-naltrexamide are much more effectively retained in the brain, suggesting a much longer effective duration of action compared to naltrexone in mice, while immediate access is considerably less. Opioid agonist half lives in humans are typically shorter, approximately 2-6 hours.

Table 5 shows the concentrations of naltrexone, 6βnaltrexol and 6β-naltrexamide in plasma and brain tissue after i.p. (intra-peritoneal) injection in mice.

TABLE 5

| Injection | Plasma concentration (ng/ml) Time after injection (min) | | Brain concentration (ng/g) Time after injection (min) | |
|---|---|---|---|---|
| | 10 | 60 | 10 | 60 |
| Naltrexone, 1 mg/kg | 54 ± 16 | 4 ± 1 | 69 ± 20 | 9 ± 1 |
| 6β-Naltrexol, 1 mg/kg | 61 ± 7 | 24 ± 28 | 7 ± 6 | 9 ± 1 |
| 6β-Naltrexol, 10 mg/kg | 857 ± 122 | 75 ± 25 | 89 ± 6 | 74 ± 14 |
| 6β-Naltrexamide, 1 mg/kg | 115 ± 2 | 18 ± 1 | 6 ± 1 | 4 ± 1 |
| 6β-Naltrexamide, 10 mg/kg | 933 ± 221 | 166 ± 77 | 27 ± 6 | 24 ± 1 |

6β-Naltrexol+Opioid as a Co-Formulated Product

The results in Table 4 and Table 5 indicate that a co-formulated product containing a specified dose of hydrocodone and 6β-naltrexol can be created that will effectively treat moderate to severe pain with limited peripheral side effects such as, but not limited to, constipation, and may possibly also reduce nausea and vomiting. The pain relief would be similar to treatment with hydrocodone alone while the peripheral side effects would be much reduced.

Moreover, this co-formulation will confer abuse resistance because the central effects of the opioid will be antagonized by the 6β-naltrexol when doses exceeding those prescribed are taken by any route of administration, including if the tablet is manipulated, crushed and injected or snorted. In the case where doses exceeding those prescribed are taken orally, the substantially longer half-life of 6β-naltrexol compared to opioid will cause 6β-naltrexol to accumulate to doses that will sufficiently penetrate the CNS to antagonize centrally-mediated opioid effects such as pain relief and euphoria. This will be beneficial in cases of both accidental and intentional overdose. Due to the substantially longer half-life of 6β-naltrexol compared to opioid agonists, the effects will become more profound as doses are increased, thus preventing this co-formulated product from oral or other abuse as is now common for opioids.

In other words, the substantially longer half-life for the neutral antagonists than of the opioid agonists means the neutral antagonist will accumulate. Dosage will therefore be determined such that when steady-state is achieved, there will be relief of the GI side effects (including possibly nausea and vomiting) without impacting pain relief. The co-formulation will be made, factoring in a calculation for regular dosing of the opioid, such that the patient or subject will receive the appropriate level of neutral antagonist to relieve GI side effects, yet still allow the opioid agonist to relieve pain. Taking higher than prescribed doses of the co-formulation prevents addiction and deters abuse because at higher or multiple doses, the neutral antagonist begins to accumulate and then competes with the effects of the opioid, lessening the pain relief, or, if the formulation is taken for pleasure, the euphoria. In cases where the co-formulation is injected as a form of abuse, the higher bioavailability of the antagonist administered directly to the bloodstream will allow antagonism of the central effects at lower doses. As with oral administration, the effects will become more profound over time as levels of the antagonist continue to accumulate through repeated dosing due to the limited half-life of the opioid. Yet, because 6β-naltrexol is a neutral antagonist, these effects will manifest without, or with substantially less, precipitating withdrawal, providing an effective means for preventing misuse. See Sadee (U.S. Pat. No. 6,713,488) and Simon (US2004/0024006).
Effect of 6β-Naltrexamide on Hydrocodone-Induced Antinociception

EXAMPLE 4

Tail Flick Assay. The tail-flick assay was used to measure antinociception as described above under Example 1.

Figure 7A:
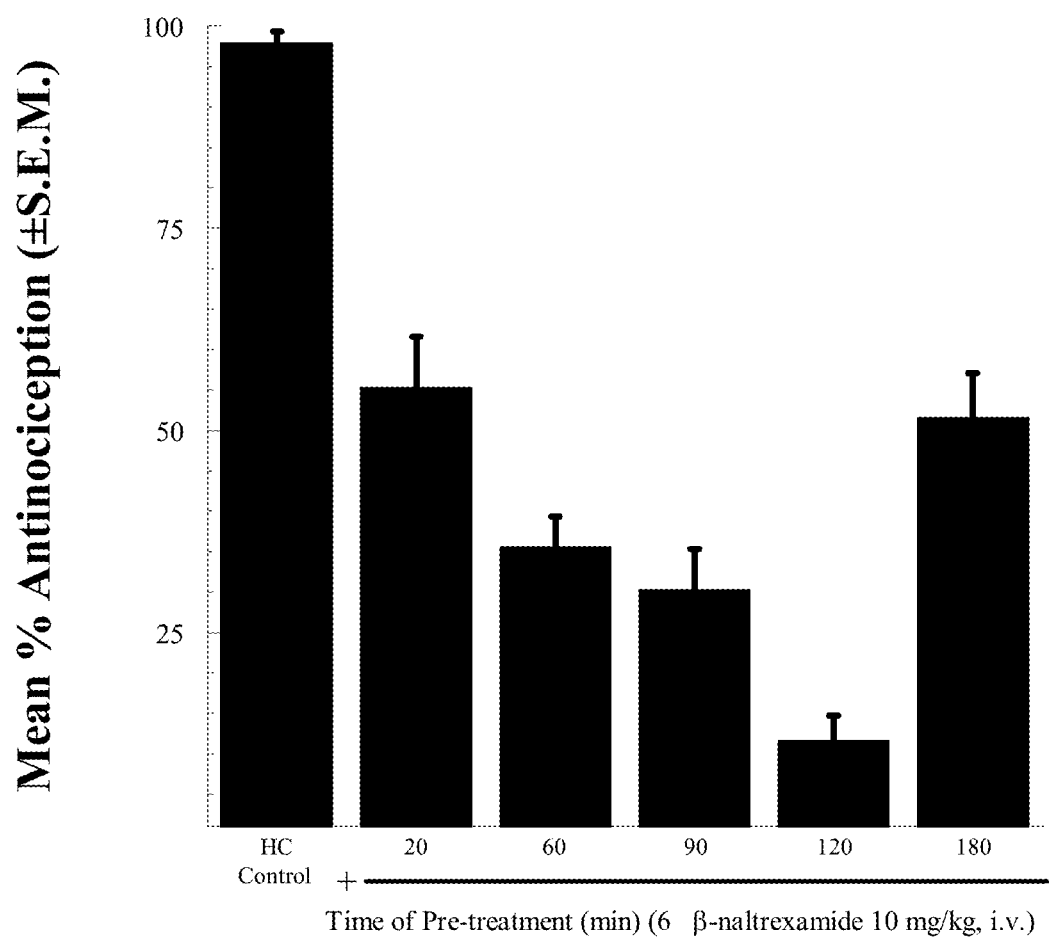
FIG. 7A is a graph that shows data reflecting the duration of the inhibitory effects of intravenously-administered 6β-naltrexamide on an antinociceptive, intravenous dose of hydrocodone, and demonstrates the time of peak effect of antinociception inhibition.
Figure 7B:
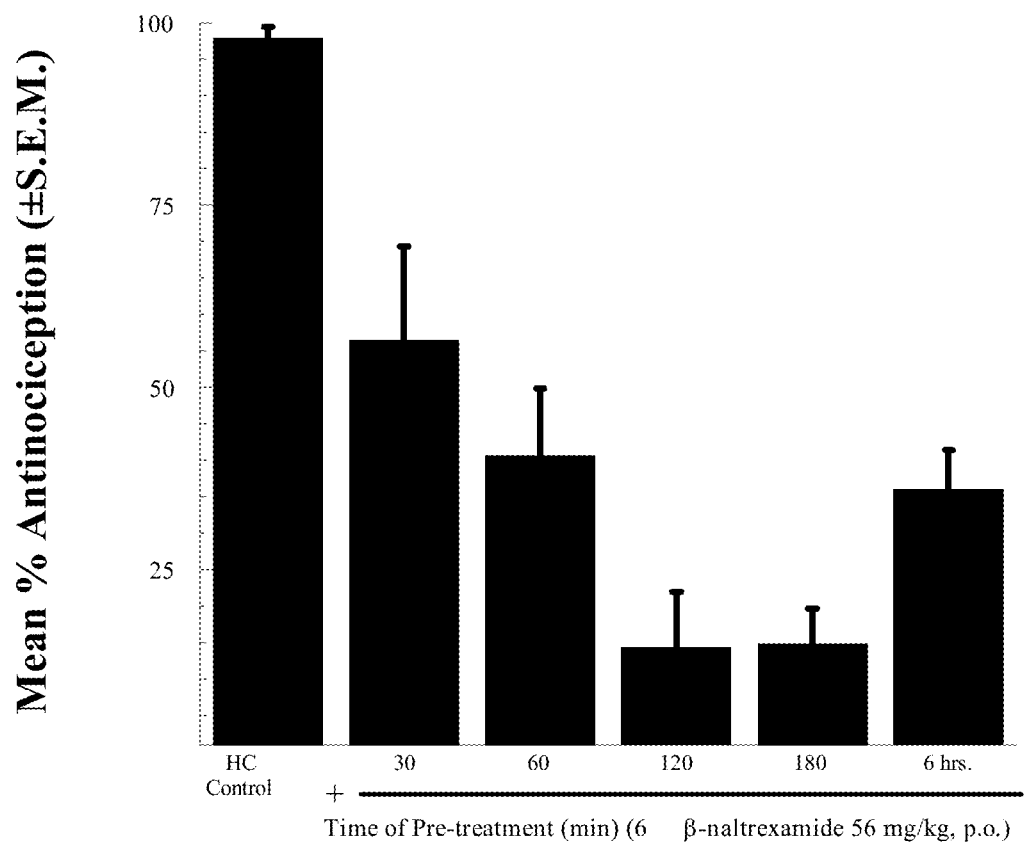
FIG. 7B is a graph that shows data reflecting the duration of the inhibitive effects of orally-administered 6β-naltrexamide on an antinociceptive, intravenous dose of hydrocodone, and demonstrates the time of peak effect of antinociception inhibition.

Antinociception Studies for Determining Time of Peak Effect of 6β-Naltrexamide. The duration of 6β-naltrexamide effects were measured by pretreating mice with 6β-naltrexamide at various times prior to an injection of an antinociceptive $A_{90}$ dose of hydrocodone (3.2 mg/kg, i.v., dose determined previously; data not shown). Mice were then tested 10 min later, at time of peak effect for hydrocodone, in the tail-flick assay. 6β-naltrexamide doses of 10 mg/kg (FIG. 7A) and 56 mg/kg (FIG. 7B) were used for i.v. and p.o. administration, respectively.

These time ranging experiments illustrated that 6β-naltrexamide was capable of reversing the centrally mediated antinociceptive effects of hydrocodone (FIGS. 7A and 7B), with a time of peak effect at 120 min for i.v. administration and 120-180 min when administered p.o.

Figure 8A:
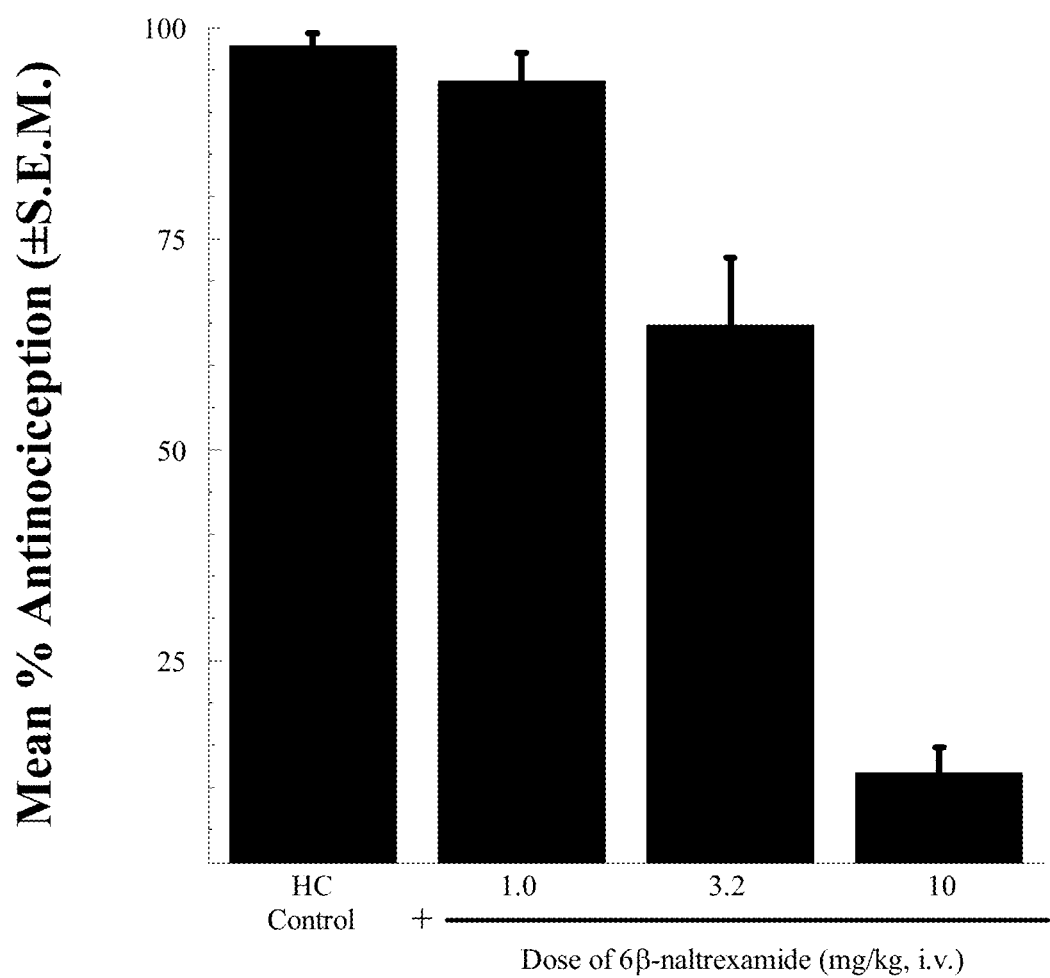
FIG. 8A is a dose response curve reflecting the potency of the inhibitory effects of intravenously-administered 6β-naltrexamide on an antinociceptive, intravenous dose of hydrocodone.
Figure 8B:
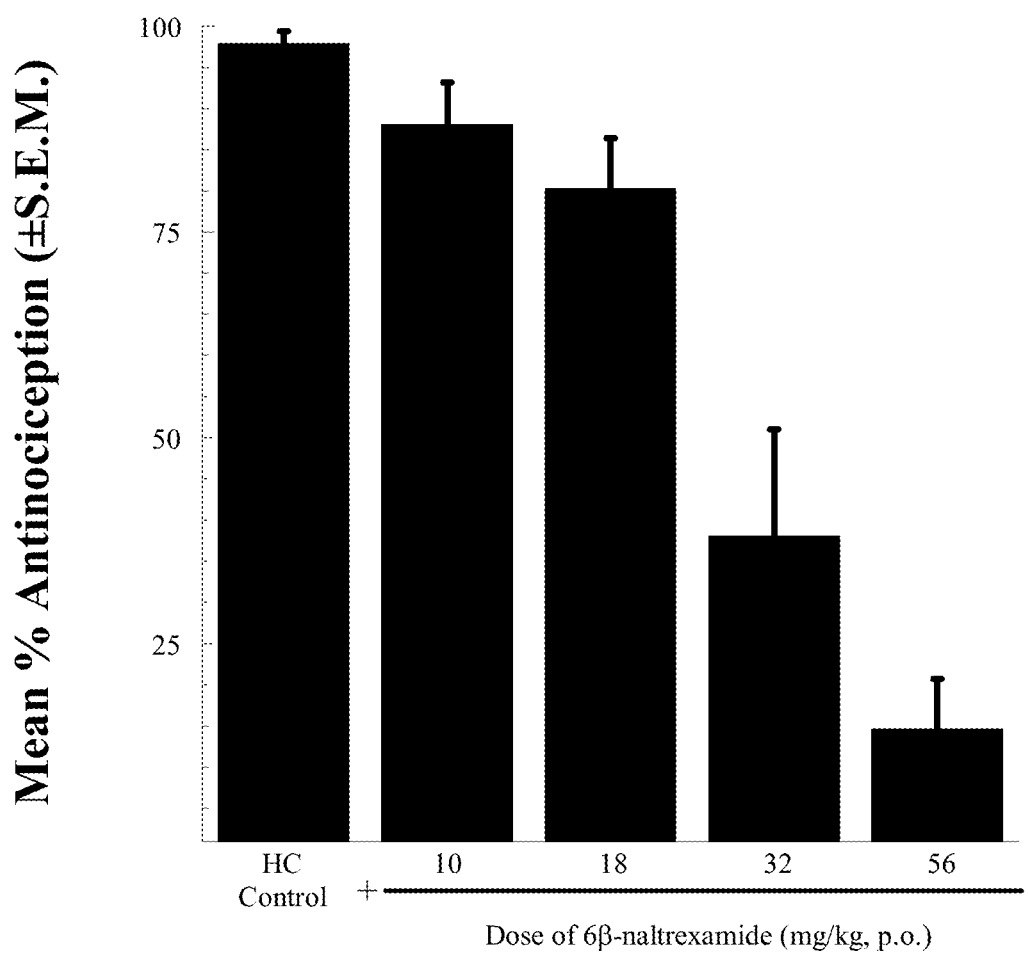
FIG. 8B is a dose response curve reflecting the potency of the inhibitory effects of orally-administered 6β-naltrexamide on an antinociceptive, intravenous dose of hydrocodone.

Antinociception Studies for Determining Antagonist Potencies. Both oral and i.v. potencies were determined by administering vehicle or various doses of 6β-naltrexamide at appropriate times prior to an $A_{90}$ dose of hydrocodone (3.2 mg/kg, i.v.). The respective i.v. (FIG. 8A) and p.o. (FIG. 8B) pretreatment times were 120 min. Mice were tested 10 min post hydrocodone injection (time of hydrocodone peak effect) in the 55° C. tail-flick assay. At least three doses were tested to produce a dose-response curve. The percent antinociception was then calculated for each dose and compared to hydrocodone controls.

These dose response curves were used to determine $ID_{50}$ value for 6β-naltrexamide. The percentage of inhibition, or reversal of the hydrocodone-induced antinociception, was calculated as (test−hydrocodone control)/(saline control−hydrocodone control)*100. From this data an $ID_{50}$ value (and 95% confidence interval) was calculated for each route using linear regression (FlashCalc software; Dr. Michael Ossipov, University of Arizona, Tucson, Ariz.). $ID_{50}$ values for 6β-naltrexamide inhibition of hydrocodone-induced antinociception were determined to be 4.06 mg/kg (95% CI=3.27-5.04) for i.v. administration, and 27.4 (22.6-33.2) for oral administration.

Antinociception Studies for Oral Co-Administration. The tail-flick assay was used to construct full dose- and time-response summaries for 6β-naltrexamide in combination with hydrocodone. Vehicle or various doses of antagonist were orally co-administered with an $A_{90}$ dose of hydrocodone (32 mg/kg, p.o.) determined previously (data not shown). Tail-flick latencies were determined at t=10, 20, 30, 45, 60, 90, 120 and 180 minutes post injection (or until 20% MPE was reached) and % antinociception was calculated for each mouse (FIG. 9).

Figure 9:
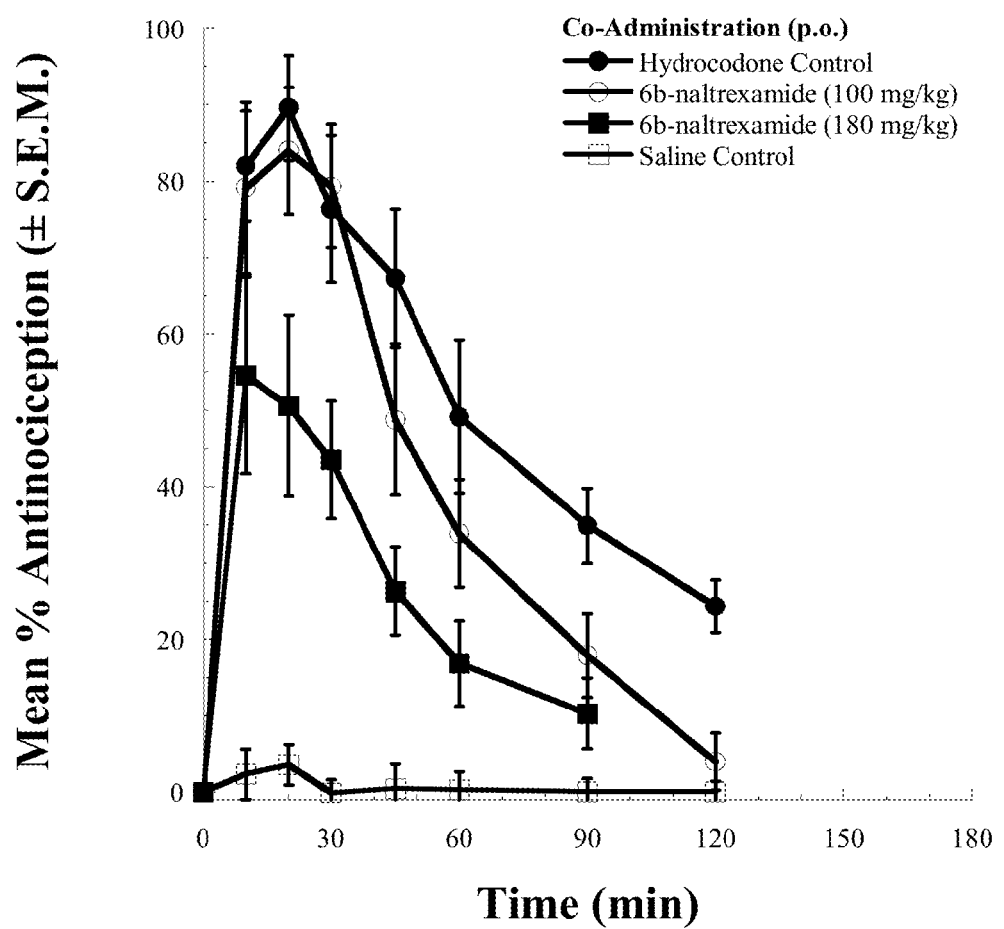

The experiments shown in FIG. 7-9 demonstrate that 6β-naltrexamide blocks hydrocodone-induced antinociception regardless of the route of administration, with a potency approximately 10-fold lower than that of 6β-naltrexol.
Effect of 6β-Naltrexamide on Hydrocodone-Induced Gastrointestinal Tract Slowing

EXAMPLE 5

GI Transit Assay. Opioid-induced GI transit inhibition was measured using standard protocols as described above under Example 2.

Figure 10A:
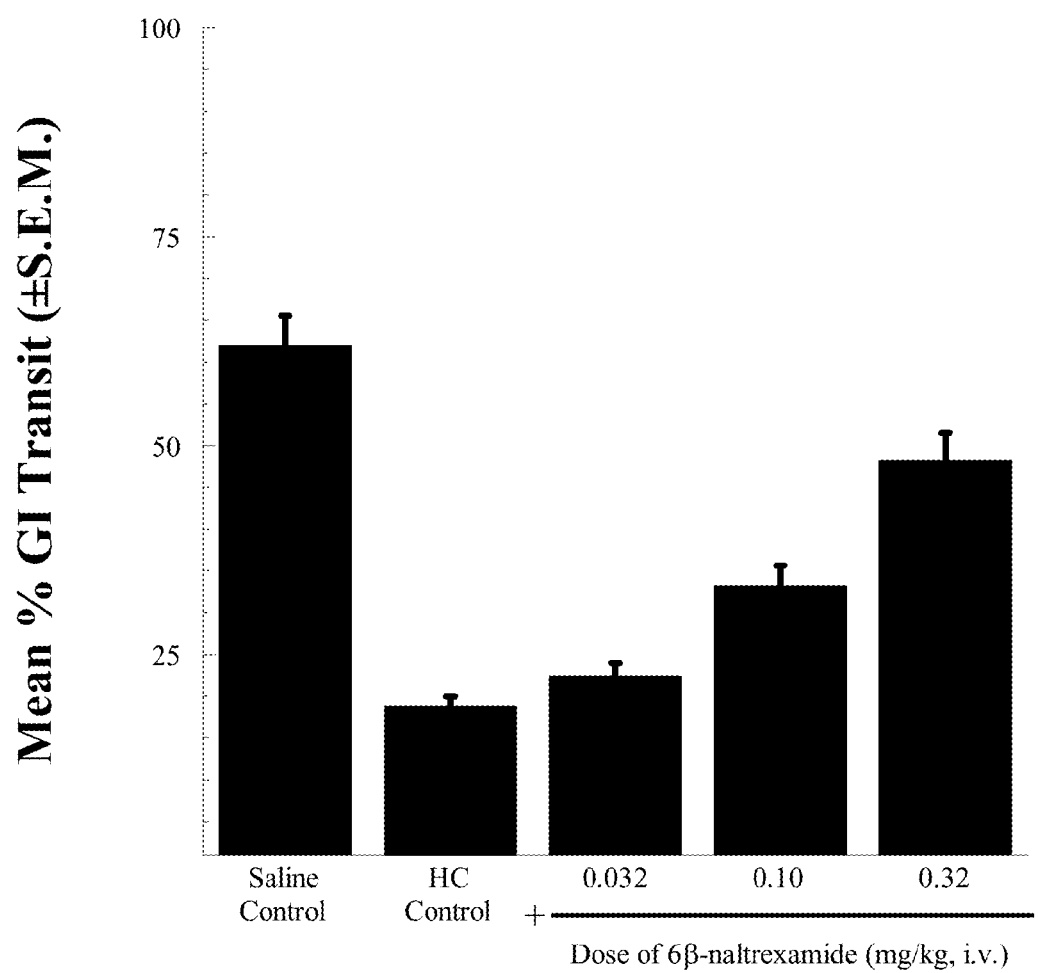
FIG. 10A is a dose response curve reflecting the potency of intravenously-administered 6β-naltrexamide to reverse hydrocodone-induced GI transit slowing, where the two compounds are not co-administered.
Figure 10B:
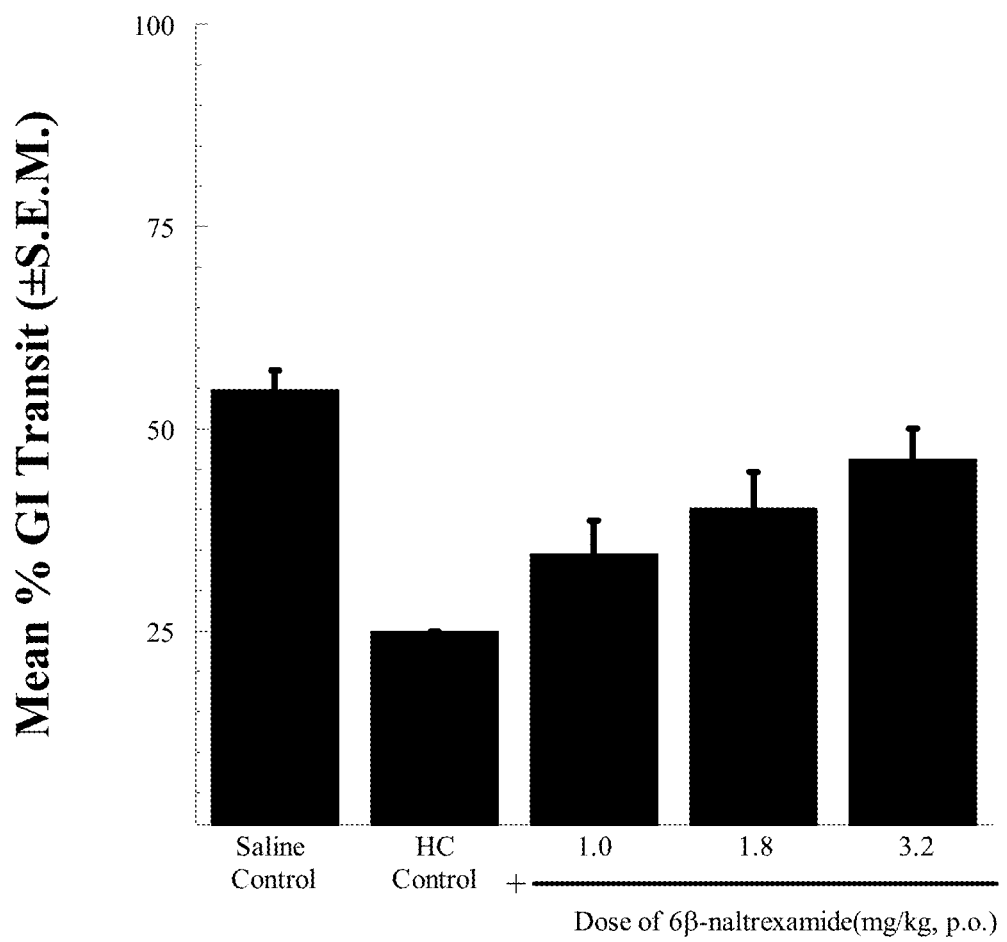
FIG. 10B is a dose response curve reflecting the potency of orally-administered 6β-naltrexamide to reverse hydrocodone-induced GI transit slowing, where the two compounds are not co-administered.

GI Transit Studies for Determining 6β-Naltrexamide Potency. The ability of 6β-naltrexamide to block hydrocodone induced GI inhibition was assessed. Both i.v. (FIG. 10A) and oral potencies (FIG. 10B) were determined by administering vehicle or various doses of 6β-naltrexamide prior to an antinociceptive $A_{90}$ dose of hydrocodone (3.2 mg/kg, i.v.). The pretreatment times corresponded with the time of peak effect for the antinociception studies. The charcoal meal was given 10 min following the injection of hydrocodone. Vehicle (saline) controls were also assessed i.v. The percentage of GI transit was calculated for each mouse and a dose-response curve was constructed for the antagonist. At least three doses were used for each route and the results were compared to saline and hydrocodone controls.

$ID_{50}$ values were calculated for 6β-naltrexamide to determine potency to inhibit hydrocodone effects. 6β-naltrexamide and hydrocodone were administered at appropriate times so that time of peak effect (as determined in the tail-flick assay) occurred during charcoal administration. When given i.v. (FIG. 10A) and p.o. (FIG. 10B) 6β-naltrexamide dose-dependently reversed the inhibition of GI transit by hydrocodone ($A_{90}$ dose, i.v.), yielding $ID_{50}$ values of 0.173 (95% CI=0.131-0.230) and 1.92 (95% CI=1.03-3.56) for i.v. and p.o. administration, respectively.

GI Transit Studies for Oral Co-Administration. Vehicle (saline) or various doses of 6β-naltrexamide are orally co-administered with an antinociceptive $A_{90}$ dose of hydrocodone (32 mg/kg, p.o.) 60 min prior to charcoal administration. This time is chosen so that the time of peak effect for the antagonist will occur during the intestinal transit of the charcoal meal. Vehicle (saline) controls are also assessed p.o. to compare the observed effects to opioid naïve mice. The percentage of GI transit is calculated for each mouse and a dose-response curve is constructed. At least three doses are used for each antagonist and the results are compared to saline and hydrocodone controls.

When given i.v. and p.o., 6β-naltrexamide is expected to dose-dependently reverse the inhibition of GI transit by hydrocodone and other analgesics with an $ID_{50}$ in the range of 0.1 to 0.2 mg/kg and 1 to 2 mg/kg for i.v. and p.o. administration, respectively.

Statistical Analysis. The dose-response curves shown in FIG. 7-10 were used to estimate and compare central (antinociception) to peripheral (GI transit) potencies of 6β-naltrexamide. The percentage of inhibition or reversal of the hydrocodone effect in either assay was determined for each mouse in the 6β-naltrexamide groups. The percent reversal was calculated as (test−hydrocodone control)/(saline control−hydrocodone control)*100. From this data an $ID_{50}$ value (and 95% confidence interval) was calculated for each route/ antagonist/assay using linear regression (FlashCalc software; Dr. Michael Ossipov, University of Arizona, Tucson, Ariz.).
Potency of 6β-Naltrexamide for Slowing GI-Transit and for Reversing Antinociception.

Figure 11A:
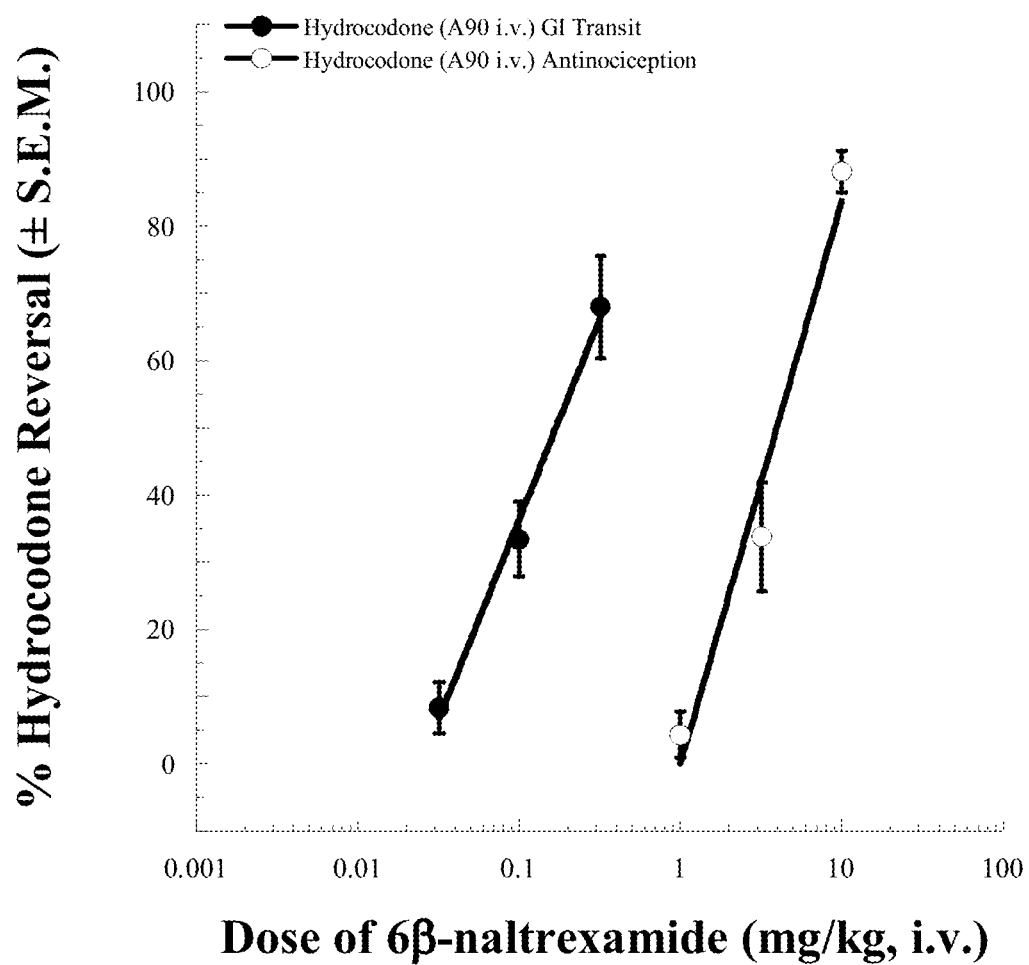
FIG. 11A shows the summarized potency data for inhibition of hydrocodone activity by 6β-naltrexamide in GI transit studies (peripheral effects) and antinociception studies (central effects), where both 6β-naltrexamide and hydrocodone were administered intravenously at different times.

Comparison of the calculated potencies ($ID_{50}$) for 6β-naltrexamide to reverse either the central effects, antinociception, or peripheral effects, GI-transit slowing, induced by hydrocodone, led to the surprising discovery that 6β-naltrexamide is 14-25-fold more potent peripherally than centrally. FIGS. 11A and B demonstrate this potency difference showing data derived from the dose response curves described above.

Figure 11B:
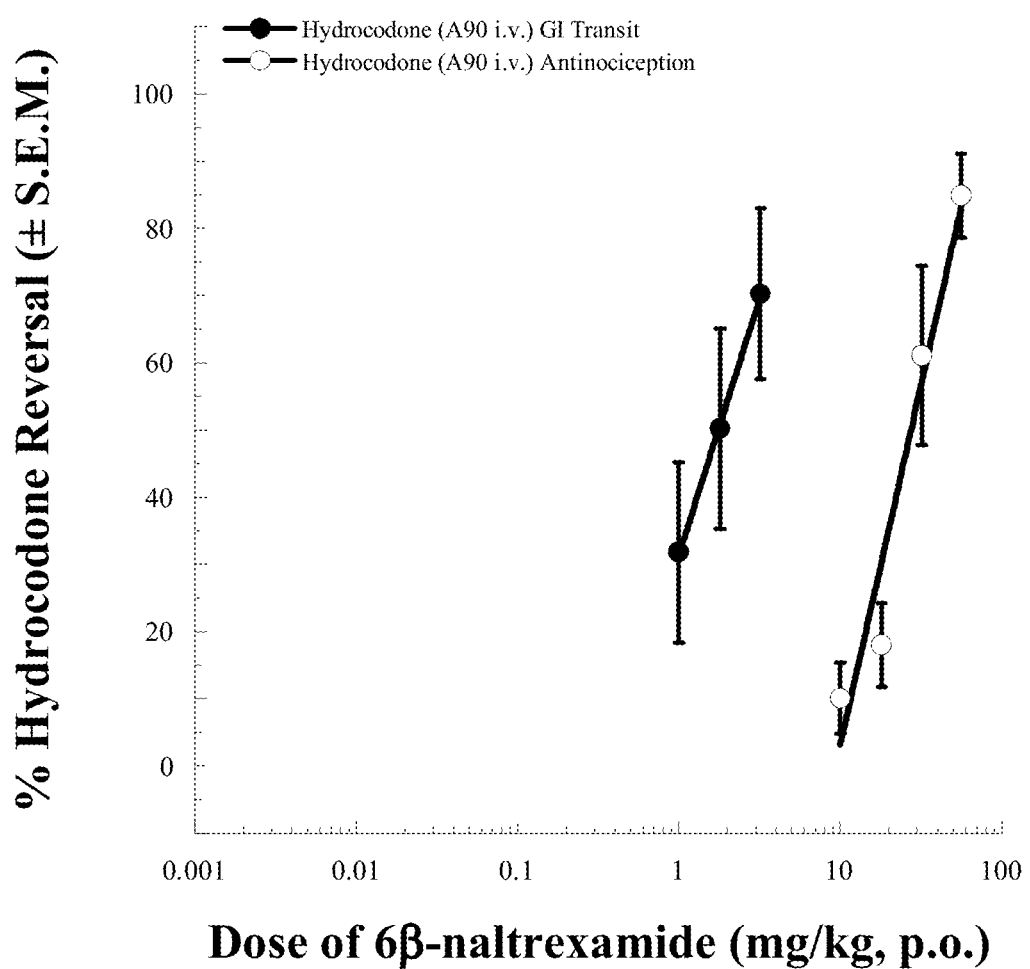
FIG. 11B shows the summarized potency data for inhibition of hydrocodone activity by 6β-naltrexamide in the GI transit studies (peripheral effects) and antinociception studies (central effects), where 6β-naltrexamide was administered orally and hydrocodone was administered intravenously at different times.

6β-naltrexamide was found to have significant shifts in potency between the two assays for all injection parameters. I.v. (FIG. 11A, Table 6) administration of 6β-naltrexamide was approximately 23-times more potent at reversing GI effects of i.v. hydrocodone than antinociceptive effects while orally administered 6β-naltrexamide demonstrated 14-fold more potency for reversing GI effects compared to antinociceptive effects (FIG. 11B, Table 6). These data suggest that 6β-naltrexamide is significantly more potent at inhibiting the peripheral effects than the central effects induced by opioids. Furthermore, oral co-administration with hydrocodone is expected to show a 10-25-fold and potentially up to a 50-fold shift in potency as well.

Thus, it is anticipated that 6β-naltrexamide will be 10-25-fold, and potentially 50-fold, more potent for slowing GI-transit than for reversing antinociception when both drugs are administered orally, so could be utilized for therapeutic use. The 6β-naltrexamide exhibited a much larger potency shift than predicted from its chemical structure, suggesting that 6β-naltrexamide may be actively prevented from entering, or is transported out of, the CNS compared to 6β-naltrexol, and thus may provide a larger therapeutic window than 6β-naltrexol.

Table 6 shows the fold-shift in peripheral vs. central potency, which was calculated and is shown as (antinociception $ID_{50}$)/(GI transit $ID_{50}$). A fold-shift less than 1.0 indicates a greater central potency over peripheral potency.

TABLE 6

| Drug Combination | GI Transit $ID_{50}$ (95% CI) (mg/kg) | Antinociception $ID_{50}$ (95% CI) (mg/kg) | Fold-Shift |
|---|---|---|---|
| 6β-naltrexamide (i.v.)/ Hydrocodone (i.v.) | 0.173 (0.131-0.230) | 4.06 (3.27-5.04) | 23.5 |
| 6β-naltrexamide (p.o.)/ Hydrocodone (i.v.) | 1.92 (1.03-3.56) | 27.4 (22.6-33.2) | 14.3 |
| 6β-naltrexamide (p.o.)/ Hydrocodone (p.o.)* | 1-2 | 3-5 | * |

* Full dose-response curves not available.

Effect of Naltrexone, a Well-Known and Characterized Antagonist, on Hydrocodone-Induced Antinociception.

Experiments with naltrexone illustrate the significant differences between the compounds taught by this application and known, characterized antagonists.

EXAMPLE 6

Tail Flick Assay. The tail-flick assay was used to measure antinociception as described above under Example 1.

Figure 12A:
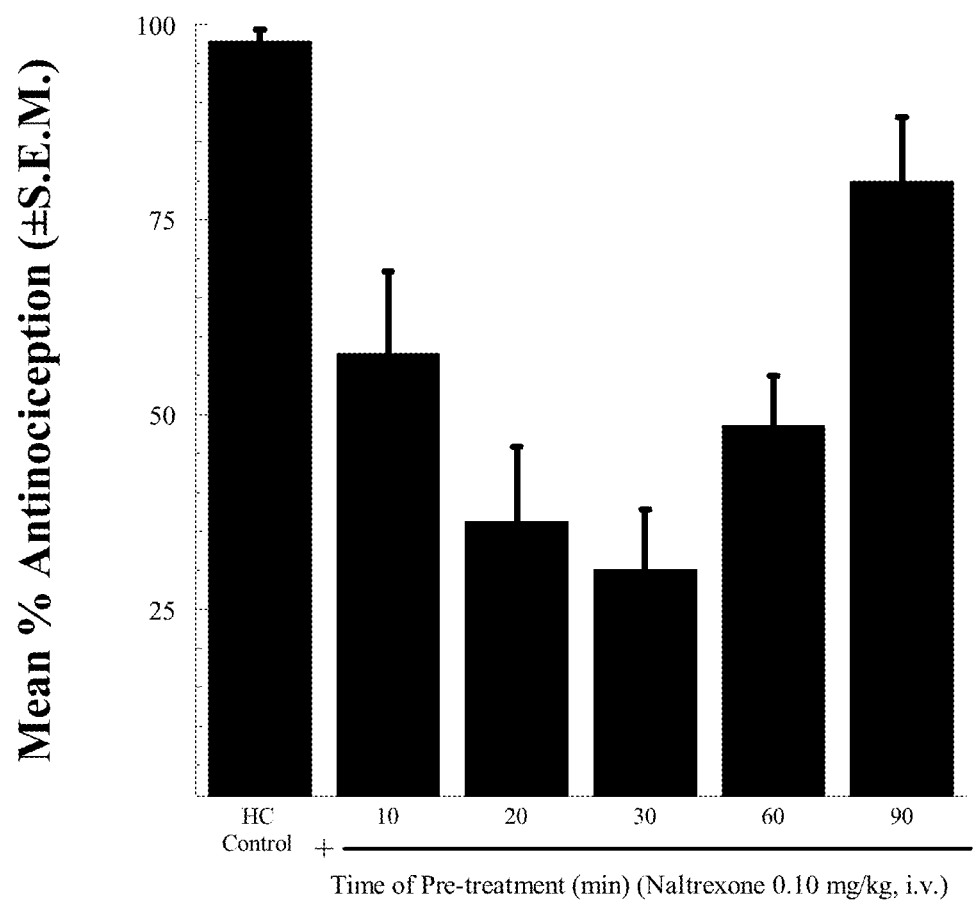
FIG. 12A is a graph that shows data reflecting the duration of the inhibitive effects of intravenously-administered naltrexone on an antinociceptive, intravenous dose of hydrocodone, and demonstrates the time of peak effect of antinociception inhibition.
Figure 12B:
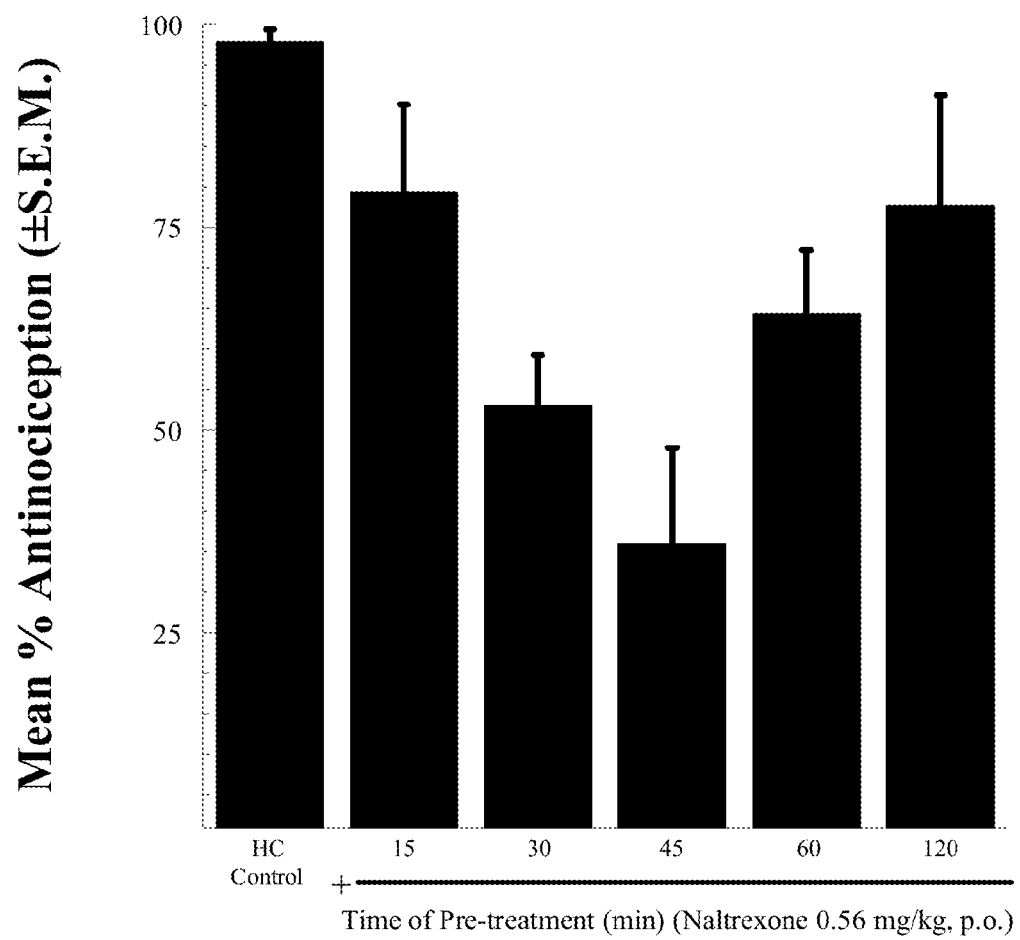
FIG. 12B is a graph that shows data reflecting the duration of the inhibitive effects of orally-administered naltrexone on an antinociceptive, intravenous dose of hydrocodone, and demonstrates the time of peak effect of antinociception inhibition.

Antinociception Studies for Determining Time of Peak Effect of Naltrexone. The duration of naltrexone effects were measured by pretreating mice with naltrexone at various times prior to an injection of an antinociceptive $A_{90}$ dose of hydrocodone (3.2 mg/kg, i.v., dose determined previously; data not shown). Mice were tested 10 min later at time of peak effect for hydrocodone in the tail-flick assay. Naltrexone doses of 0.10 mg/kg for i.v. (FIG. 12A) and 0.56 mg/kg for p.o. (FIG. 12B) were used.

Figure 13A:
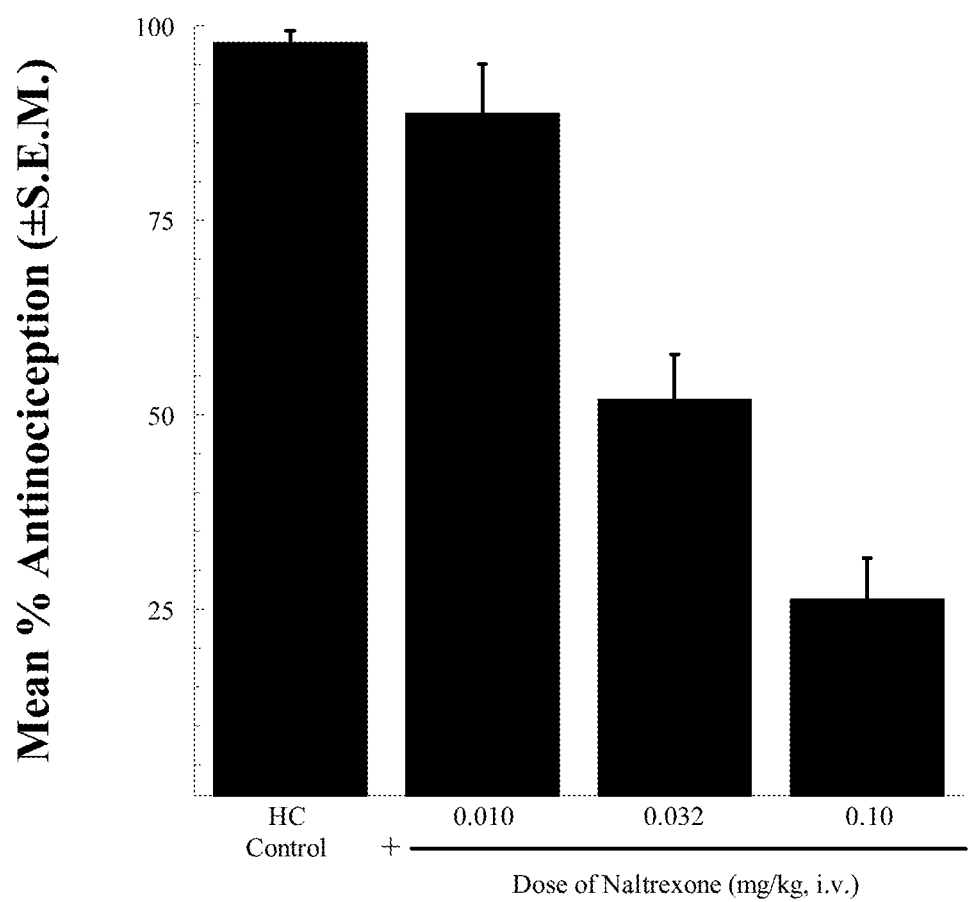
FIG. 13A is a dose response curve reflecting the potency of the inhibitory effects of intravenously-administered naltrexone on an antinociceptive, intravenous dose of hydrocodone.
Figure 13B:
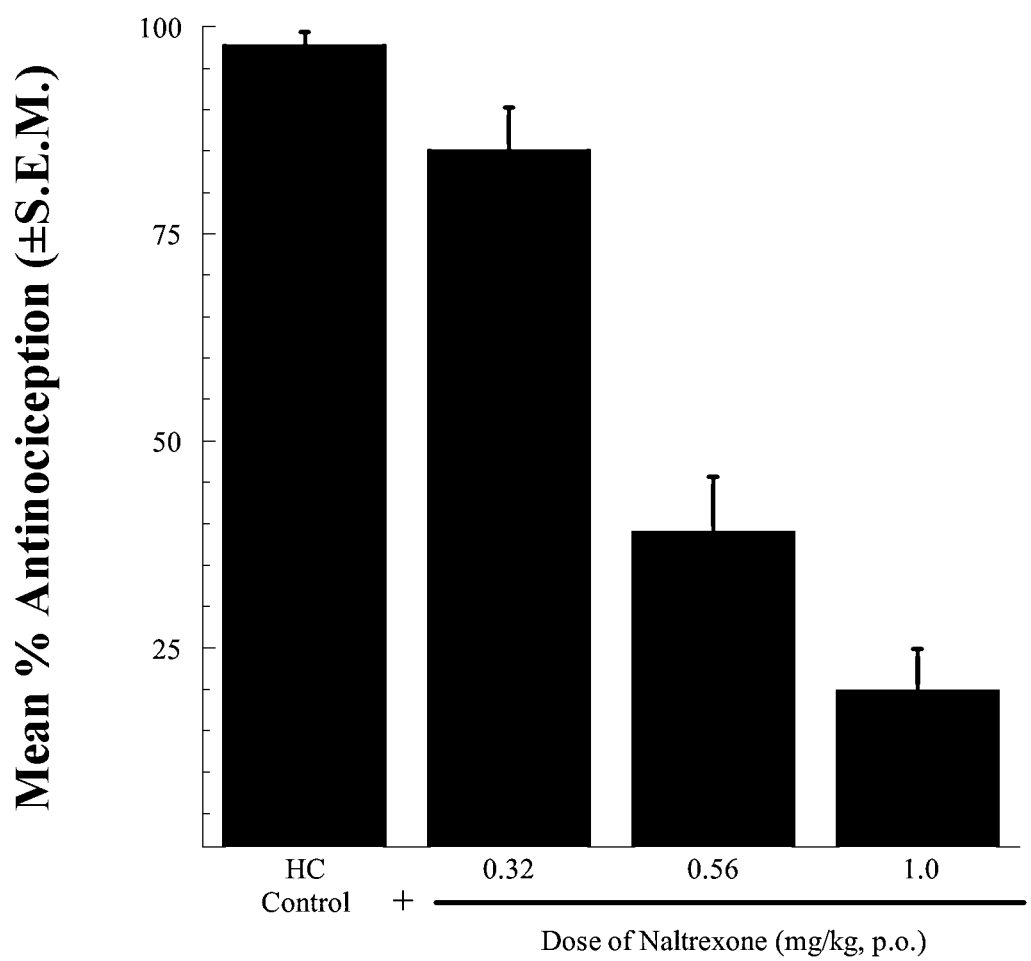
FIG. 13B is a dose response curve reflecting the potency of the inhibitory effects of orally-administered naltrexone on an antinociceptive, intravenous dose of hydrocodone.

These time ranging experiments illustrate that naltrexone was capable of reversing the centrally mediated antinociceptive effects of hydrocodone (FIGS. 13A and 13B), with a time of peak effect at 30 min for i.v. administration and 45 min when administered p.o.

Antinociception Studies for Determining Antagonist Potencies. Both oral and i.v. potencies were determined by administering vehicle or various doses of naltrexone at appropriate times prior to an $A_{90}$ dose of hydrocodone (3.2 mg/kg, i.v.). The respective i.v. (FIG. 13A) and p.o. (FIG. 13B) pretreatment times were 30 and 45 min. Mice were tested 10 min post hydrocodone injection (time of hydrocodone peak effect) in the 55° C. tail-flick assay. At least three doses were tested to produce a dose-response curve. The percent antinociception was then calculated for each dose and compared to hydrocodone controls.

These dose response curves were used to determine $ID_{50}$ value for naltrexone in these experiments for comparison purposes. The percentage of inhibition or reversal of the hydrocodone-induced antinociception was calculated as (test−hydrocodone control)/(saline control−hydrocodone control)*100. From this data an $ID_{50}$ value (and 95% confidence interval) was calculated for each route using linear regression (FlashCalc software; Dr. Michael Ossipov, University of Arizona, Tucson, Ariz.). $ID_{50}$ values for naltrexone inhibition of hydrocodone-induced antinociception were determined to be 0.0411 (0.0319-0.0529) for i.v. administration, and 0.534 (0.471-0.605) for oral administration. These values are consistent with published values for the oral bioavailability of natrexone and with the published observation that 6β-naltrexol is approximately 5-10-fold less potent than naltrexone for reversing morphine-induced antinociception (Wang D., Raehal K. M., Lin E. T., Lowery J. J., Kieffer B. L., Bilsky E. J., Sadee W. (2004 February Epub 2003 Nov. 4) "Basal signaling activity of mu opioid receptor in mouse brain: role in narcotic dependence," *J Pharmacol Exp Ther.*; 308(2):512-20; Raehal K. M., Lowery J. J., Bhamidipati C. M., Paolino R. M., Blair J. R., Wang D., Sadee W., Bilsky E. J. (2005 June; Epub 2005 Feb. 16), depending on route of administration.

Figure 15A:
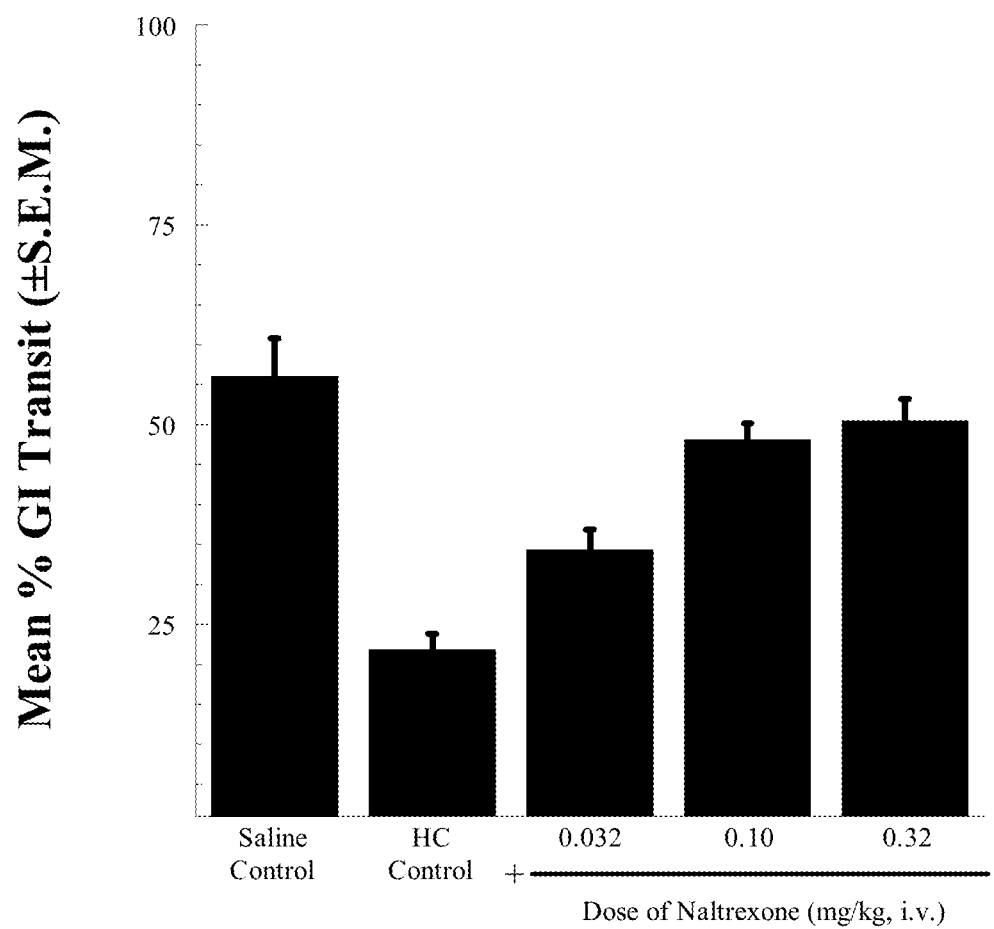
FIG. 15A is a dose response curve reflecting the potency of intravenously-administered naltrexone to reverse hydrocodone-induced GI transit slowing.
Figure 15B:
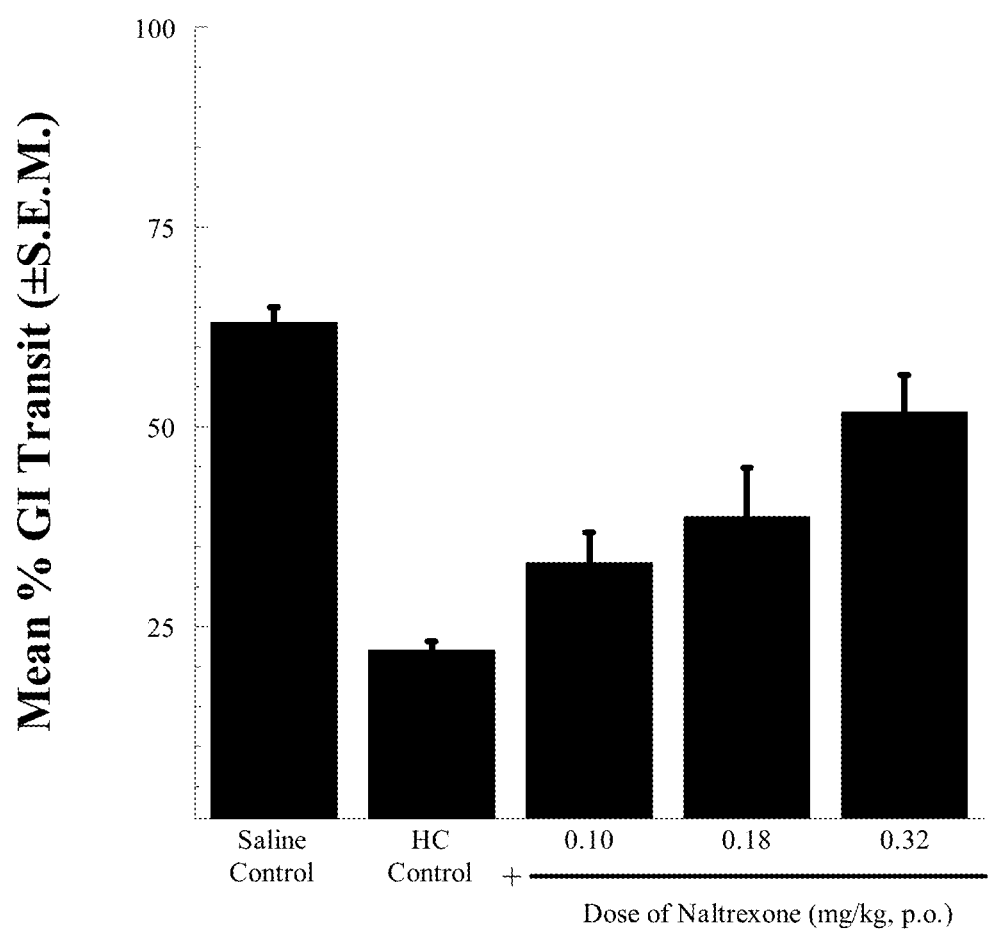
FIG. 15B is a dose response curve reflecting the potency of orally-administered naltrexone to reverse hydrocodone-induced GI transit slowing.

Antinociception Studies for Oral Co-Administration. The tail-flick assay was used to construct full dose- and time-response summaries for naltrexone in combination with hydrocodone. Vehicle or various doses of antagonist were orally co-administered with an $A_{90}$ dose of hydrocodone (32 mg/kg, p.o.) determined previously (data not shown). Tail-flick latencies were determined at t=10, 20, 30, 45, 60, 90, 120 and 180 minutes post injection (or until 20% MPE was reached) and % antinociception was calculated for each mouse (FIG. 15).

Figure 14:
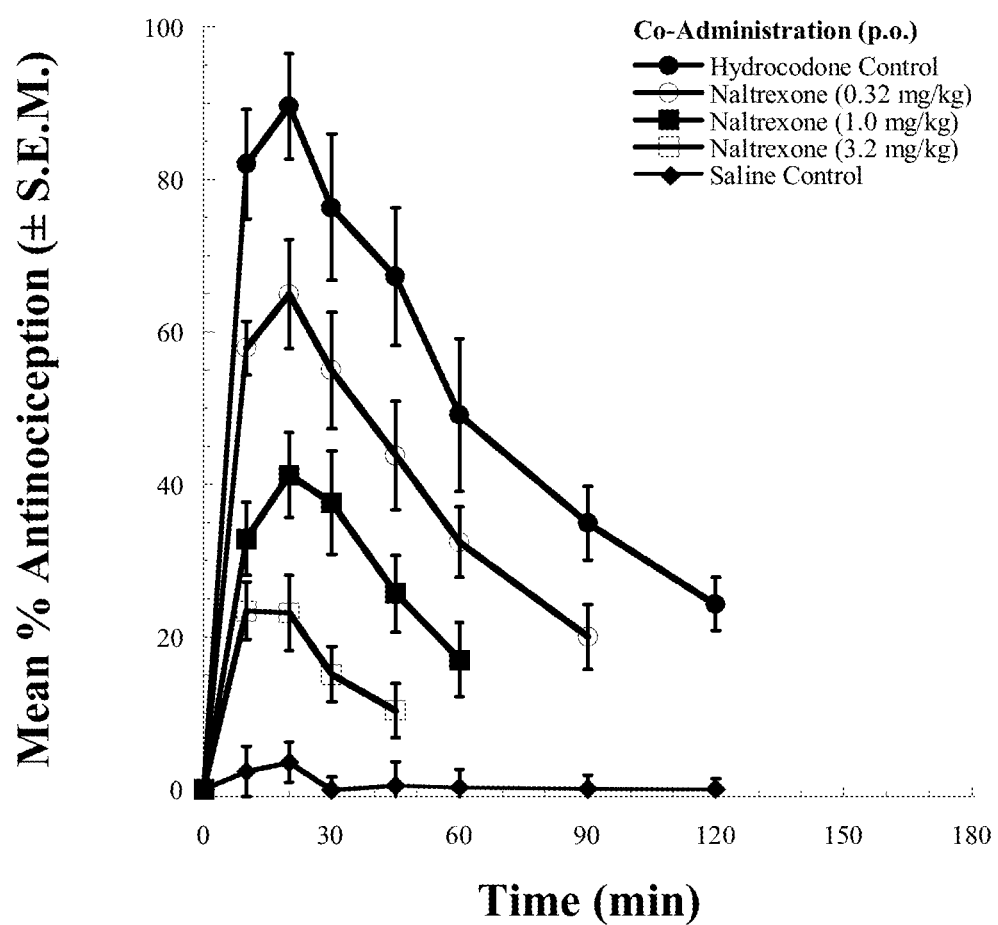

The antinociception experiments shown in FIG. 14 yield an $ID_{50}$ value of 0.914 mg/kg (95% CI=3.27-5.04) for naltrexone co-administered with hydrocodone.

The experiments shown in FIG. 12-14 demonstrate that naltrexone blocks hydrocodone-induced antinociception regardless of the route of administration, consistent with the many published reports on naltrexone and its clinical use for the treatment of alcoholism and opioid addiction.

Effect of Naltrexone on Hydrocodone-Induced Gastrointestinal Tract Slowing

EXAMPLE 7

GI Transit Assay. Opioid-induced GI transit inhibition was measured using standard protocols as described above under Example 2.

GI Transit Studies for Determining Naltrexone Potency. The ability of naltrexone to block hydrocodone-induced GI inhibition was assessed. Both i.v. (FIG. 15A) and oral potencies (FIG. 15B) were determined by administering vehicle or various doses of naltrexone prior to an antinociceptive $A_{90}$ dose of hydrocodone (3.2 mg/kg, i.v.). The pretreatment times corresponded with the time of peak effect for the antinociception studies. The charcoal meal was given 10 min following the injection of hydrocodone. Vehicle (saline) controls were also assessed i.v. The percentage of GI transit was calculated for each mouse and a dose-response curve was constructed. At least three doses were used for each route and the results were compared to saline and hydrocodone controls.

$ID_{50}$ values were calculated for naltrexone to determine potency to inhibit hydrocodone effects. Naltrexone and hydrocodone were administered at appropriate times so that time of peak effect (as determined in the tail-flick assay) occurred during charcoal administration. When given by i.v. (FIG. 15a) and p.o. (FIG. 15b) naltrexone dose-dependently reversed the inhibition of GI transit by hydrocodone ($A_{90}$ dose, i.v.), yielding $ID_{50}$ values of 0.0456 (95% CI=0.0275-0.0757) for i.v. and 0.194 (95% CI=0.136-0.277) for p.o. administration, respectively.

Figure 16:
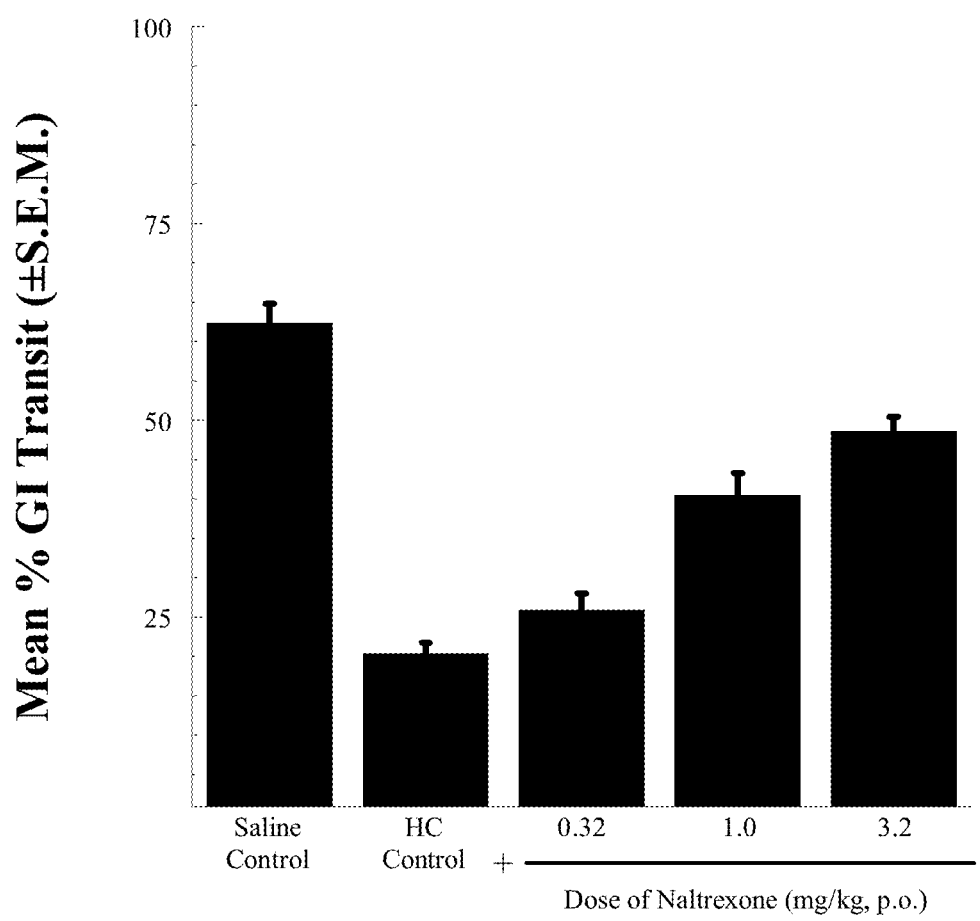

GI Transit Studies for Oral Co-Administration. Vehicle (saline) or various doses of naltrexone was orally co-administered with an antinociceptive $A_{90}$ dose of hydrocodone (32 mg/kg, p.o.) 15 min prior to charcoal administration (FIG. 16). This time was chosen so that the time of peak effect for the antagonist would occur during the GI transit of the charcoal meal. Vehicle (saline) controls were also assessed p.o. to compare the observed effects to opioid naïve mice. The percentage of GI transit was calculated for each mouse and a dose-response curve was constructed. At least three doses were used for each antagonist and the results were compared to saline and hydrocodone controls.

Naltrexone orally co-administered with hydrocodone ($A_{90}$ dose, p.o.) again dose-dependently reversed GI inhibition (FIG. 16) with an $ID_{50}$ of 1.40 mg/kg (95% CI=1.07-1.84).

Statistical Analysis. The dose-response curves shown in FIG. 13-16 were used to estimate and compare central (antinociception) to peripheral (GI transit) potencies for naltrexone. The percentage of inhibition or reversal of the hydrocodone effect in either assay was determined for each mouse in the naltrexone groups. The percent reversal was calculated as (test−hydrocodone control)/(saline control−hydrocodone control)*100. From this data an $ID_{50}$ value (and 95% confidence interval) was calculated for each route/antagonist/assay using linear regression (FlashCalc software; Dr. Michael Ossipov, University of Arizona, Tucson, Ariz.).

Potency of Naltrexone for Slowing GI-Transit and for Reversing Antinociception.

Figure 17A:
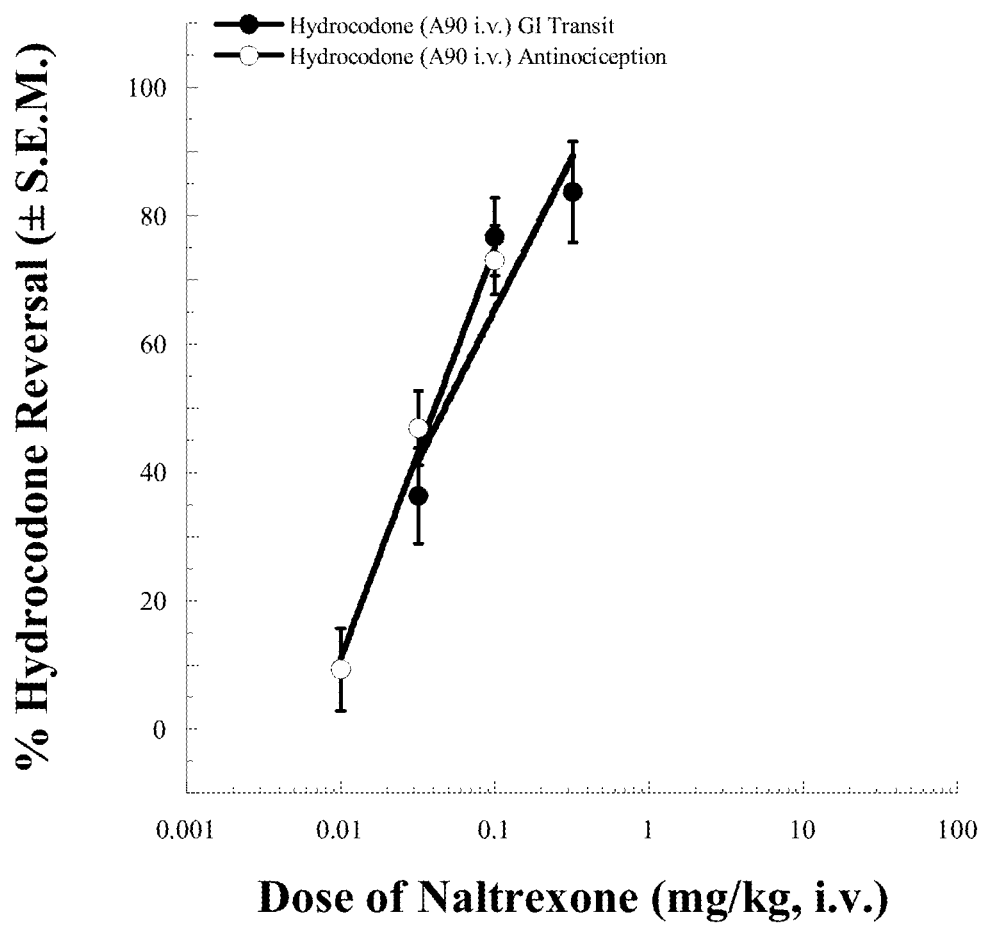
FIG. 17A shows the summarized potency data for inhibition of the effects of intravenously-administered hydrocodone by intravenously-administered naltrexone in the GI transit studies (peripheral effects) and antinociception studies (central effects).
Figure 17B:
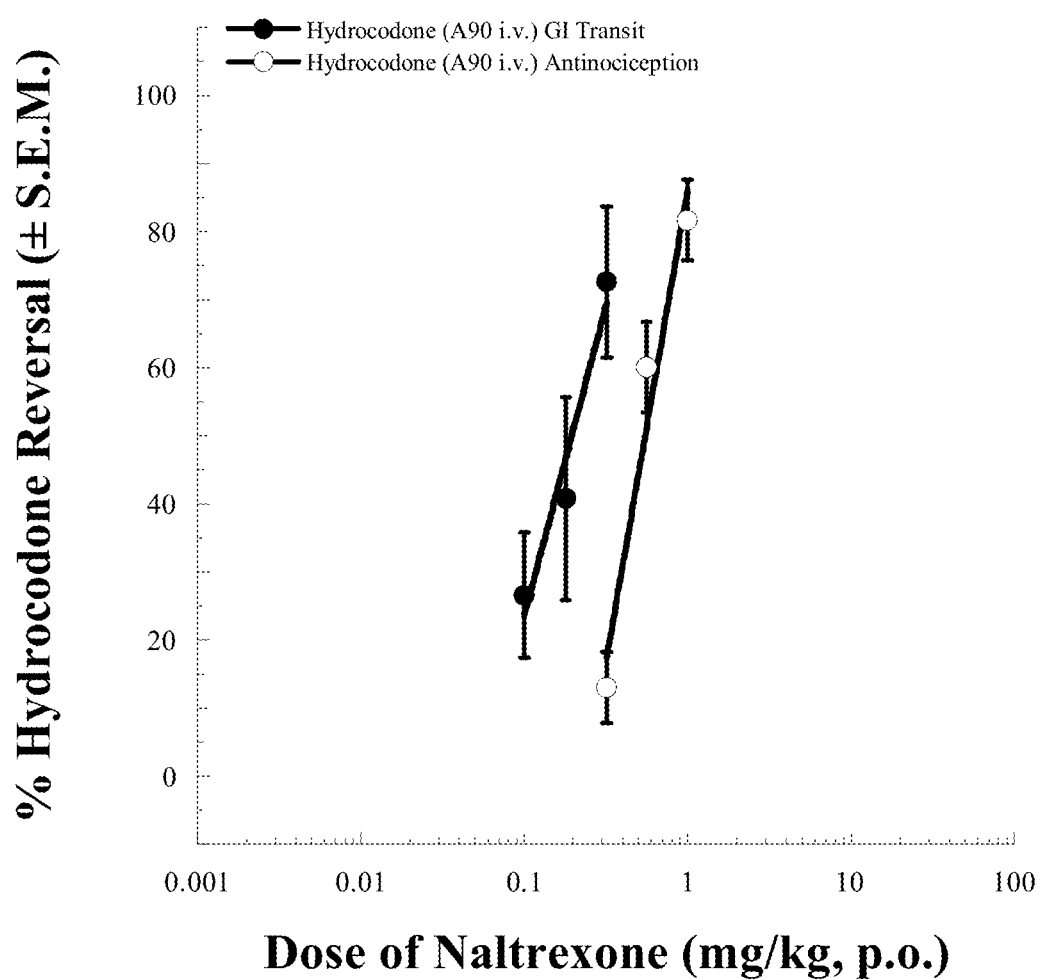
FIG. 17B shows the summarized potency data for inhibition of the effects of intravenously-administered hydrocodone by orally-administered naltrexone in the GI transit studies (peripheral effects) and antinociception studies (central effects).

Comparison of the calculated potencies ($ID_{50}$) for naltrexone to reverse either the central effects, antinociception, or peripheral effects, GI-transit slowing, demonstrated that naltrexone was nearly equipotent peripherally and centrally. FIG. 17A-B illustrate the potency differences showing data derived from the dose response curves described above.

Figure 17C:
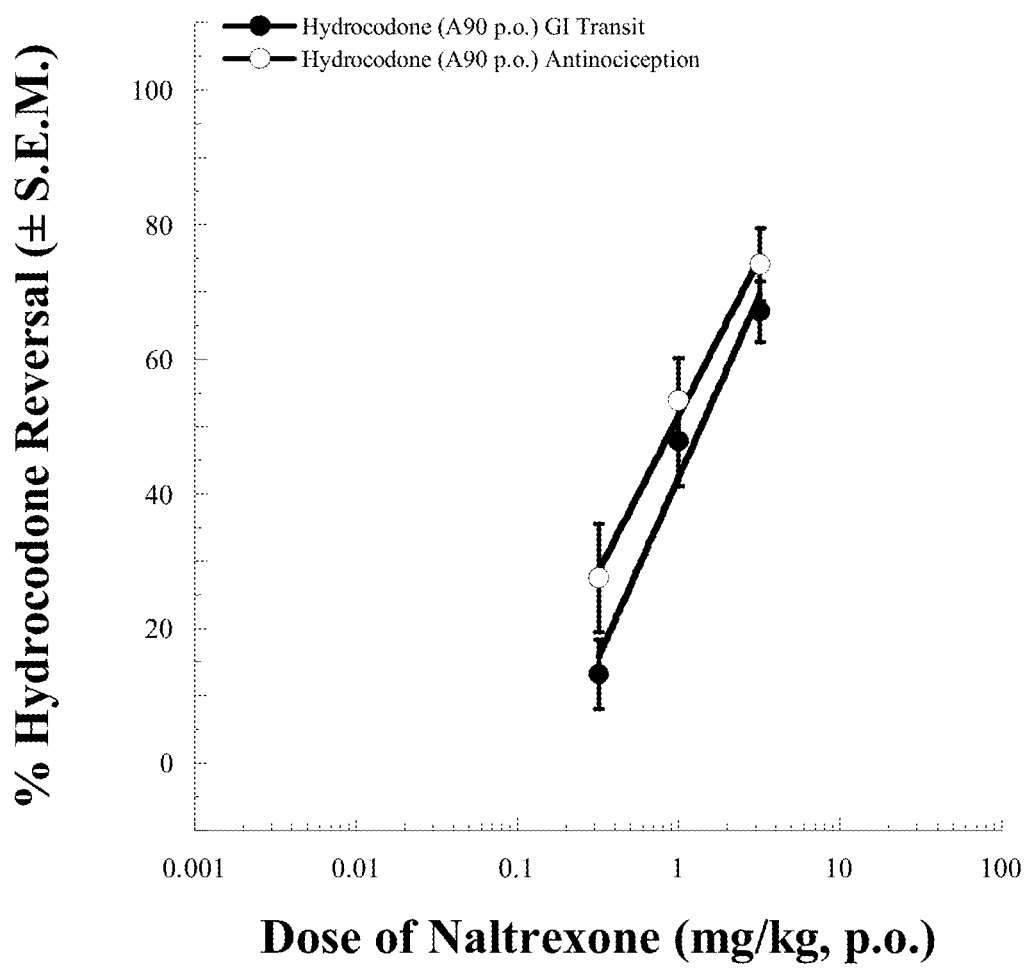

Naltrexone was found to have small or negligible shifts in potency between the two assays for all injection parameters. I.v. (FIG. 17A, Table 7 below) administration of naltrexone was approximately equipotent at reversing GI effects of i.v. hydrocodone than antinociceptive effects while orally administered naltrexone demonstrated only a 3-fold difference in potency for reversing GI effects compared to antinociceptive effects (FIG. 17B, Table 7). Furthermore, oral co-administration with hydrocodone resulted in a 0.6-fold shift in potency, actually exhibiting more central than peripheral potency (FIG. 17C, Table 7). These data suggest that naltrexone is nearly equipotent for inhibiting peripheral effects and central effects induced by opioids, consistent with its medicinal use as a treatment for alcoholism and opioid addiction.

Table 7 shows the fold-shift in peripheral vs. central potency as calculated and shown as (antinociception $ID_{50}$)/(GI transit $ID_{50}$). A fold-shift less than 1.0 indicates a greater central potency over peripheral potency.

TABLE 7

| Drug Combination | GI Transit $ID_{50}$ (95% CI) (mg/kg) | Antinociception $ID_{50}$ (95% CI) (mg/kg) | Fold-Shift |
|---|---|---|---|
| Naltrexone (i.v.)/Hydrocodone (i.v.) | 0.0456 (0.0275-0.0757) | 0.0411 (0.0319-0.0529) | 0.901 |
| Naltrexone (p.o.)/Hydrocodone (i.v.) | 0.194 (0.136-0.277) | 0.534 (0.471-0.605) | 2.75 |
| Naltrexone (p.o.)/Hydrocodone (p.o.) | 1.40 (1.07-1.84) | 0.914 (0.628-1.33) | 0.653 |

These data illustrate the difference in activity between known, clinically used antagonists and the novel activities of the neutral antagonists taught in this application.

Moreover, a strong induction of diarrhea was present with administration of naltrexone, but was absent with naltrexol and naltrexamide.

6β-Naltrexol Peripheral and CNS Potency Against Morphine

EXAMPLE 8

6β-Naltrexol has been reported to act as a neutral antagonist with peripheral selectivity in opioid naïve and opioid dependent systems in vitro and in vivo. These exploratory studies were conducted to test whether the neutral opioid antagonist 6β-naltrexol, the primary metabolite of naltrexone, could selectively inhibit gastrointestinal opioid effects in human subjects.

Protocol. Ten healthy, opioid-naïve male volunteers were enrolled in a randomized, double-blind, placebo-controlled, five-way cross-over study under an Exploratory Investigational New Drug application. Five male subjects each received five sequential administrations of escalating doses of 6β-naltrexol as the hydrochloride salt or placebo by IV infusion over 30 min (1, 3, 10, and 20 mg). Commercially available morphine sulfate for injection (10 mg) was dissolved in 5 mL normal saline and administered IV over 60 sec, within 5 min after the start of 6β-naltrexol infusion. Evaluations were made at screening, check-in, prior to dosing, during dosing, following the end of dosing, and at follow-up seven days after the last dose in each Group. On Day 0, subjects were randomized and received the first dose of 6β-naltrexol or placebo, following the treatment schedule in Tables 8A and 8B below. Each treatment session was separated by at least 72 hours to afford substantial elimination of 6β-naltrexol, with a 12-hour elimination half-life[2]. During two treatment sessions, blood samples were collected from pre-dose through 36 hours after 6β-naltrexol dosing, to determine plasma levels of morphine and 6β-naltrexol. During each treatment session, subjects underwent pupillometry, cold pressor, and $H_2$ breath tests to determine onset and duration of opioid agonist and antagonist effects. Subjects were monitored for adverse events (AEs) throughout the study. Plasma samples corresponding to the 3.0 mg dosing from Group 1 and 10.0 mg dosing from Group 2 were analyzed using a proprietary high pressure liquid chromatography, tandem mass spectrometry method validated according to FDA guidelines. As a measure of oral-cecal transit time, a Quintron hydrogen breath analyzer was used to determine $H_2$ content of exhaled air. A Jeio Tech circulating water bath (Model RW-1025G) was used for the cold pressor testing. At screening, subjects underwent a cold pressor test by immersion of the non-dominant hand in 2.0° C. (±0.1° C.) water. The hand remained in the water for as long as was tolerated by the subject or to a previously determined maximal cutoff of 180 seconds. Pupil measurements were performed using a Colvard pupillometer according to the manufacturer's specification. (For details see J. Yancey-Wrona, T. J. Raymond, H. K. Mercer, W. Sadee, E. J. Bilsky 6β-Naltrexol, a peripherally selective opioid antagonist that inhibits morphine-induced slowing of gastrointestinal transit: An exploratory study. *Pain Medicine* 12: 1727-1737 (2011); herein incorporated by reference in its entirety).

Oral-cecal transit time was measured using the lactulose-hydrogen breath test. For CNS effects, analgesia was evaluated using a cold pressor test, and eye pupil size was measured. Blood samples were collected over 36 hours for pharmacokinetic analyses. As shown in FIG. 18, the mean terminal plasma elimination half-life of 6β-naltrexol was 11.1±2.4 hours Simulated plasma concentration-time profiles for combined oxycodone (20 mg) and 6β-naltrexol (7.5 mg) (referred to as AIKO-150 in FIGS. 19A-19C) formulation after oral dosing with an immediate release formulation were next determined. The dosing intervals are every 12 hours in FIG. 19A, every 2 hours in FIG. 19B, and starting with every 12 hours then switching to every 2 hours in FIG. 19C (to simulate the beginning of abuse of the combination formulation. Oxycodone, used here as the opioid analgesic, has pharmacokinetics parameters and a potency similar to that of morphine (see Tables 1A and 1B above). Furthermore, FIGS. 19A-19C show that over time, particularly with dosages every 2 hours (see FIGS. 19B and 19C), 6β-naltrexol accumulates in the plasma more than the oxycodone accumulates.

Next, the oral-cecal transit time was measured in the subjects that had received 10 mg morphine and either 0 mg, 1 mg, 3 mg, 10 mg, or 20 mg 6β-Naltrexol intravenously. The Oral-cecal transit time was indicated by the time of peak exhaled $H_2$ in breath over 4 hours at 15 min intervals following intravenous infusion of 0 mg, 1 mg, 3 mg, 10 mg, or 20 mg 6β-Naltrexol in the presence or absence of morphine. As shown in FIG. 20, when morphine was given intravenously (i.v.) at 10 mg doses, approximately 3 mg of 6β-naltrexol i.v. was sufficient to suppress the morphine effect on GI motility (i.e., a peripheral effect of morphine) by 50%. FIG. 20 shows the mean lag times when the amount of $H_2$ increased significantly above the baseline value as a measure of oral-cecal transit time. Note that for FIG. 20, an arbitrary value of 350 min was assigned for sessions where $H_2$ levels did not increase significantly at any time point during the 240 min measurement. As shown in FIG. 20, 6β-naltrexol potently blocked morphine-induced slowing of gastrointestinal transit, with an $ED_{50}$ of approximately 3 mg, as measured by the oral-cecal transit time.

In contrast, no effect was observed with 6β-naltrexol doses up to 20 mg on morphine-induced analgesia (FIG. 21B) or pupil constriction (FIG. 21A). Both analgesia and pupil constriction are central effects of morphine. In these studies in FIGS. 21A and 21B, intravenous 6β-naltrexol infusion over 30 minutes was well tolerated up to the highest dose tested.

From these studies, it was found that 6β-Naltrexol displayed the expected half-life in humans of approximately 12 hours (see FIG. 18), satisfying the criterion that the neutral antagonist should, in some embodiments, exceed that of common opioid analgesics such as morphine at least twofold. When morphine was given i.v. at 10 mg doses, approximately 3 mg of 6β-naltrexol i.v. was sufficient to suppress the morphine effect on GI motility by 50% (FIG. 19). Importantly, 20 mg 6β-naltrexol was still well tolerated while completely suppressing the peripheral morphine effects on GI motility (see FIG. 20), whereas 6β-naltrexol up to 20 mg had no effect on morphine induced pupil dilation and analgesia (see FIGS. 21A and 21B). It is also noted that 6β-naltrexol given up to 20 mg i.v. was well tolerated by all subjects. To determine an effective dosage ratio morphine/6β-naltrexol for suppressing peripheral effect but not CNS effects of morphine, one must consider differences in distribution and half-life, so that under repetitive dosing the relative potencies of agonist and antagonist may be changed. On the basis of animal data, 6β-naltrexol is expected to inhibit CNS effects of morphine at doses of 6β-naltrexol somewhat above 20 mg i.v. since 6β-naltrexol preferentially antagonizes opioid effects on gastrointestinal transit compared to antinociception in mice. J. Yancey-Wrona, T. J. Raymond, H. K Mercer, W. Sadee, E. J. Bilsky Life Sci., 413-420 (2009)). However, during repetitive dosing and with slow equilibration of the co-formulation of the neutral antagonist and the opioid agonist described herein, the dosage level in the body that needs to be achieved to begin blunting morphine's CNS effect can begin at approximately 20 mg 6β-Naltrexol cumulative daily dose.

6β-Naltrexol Effects in Methadone Maintenance Patients

EXAMPLE 9

Summary. Complications of prescription opioid use include abuse and constipation. 6β-Naltrexol, a neutral opioid antagonist, may alleviate these complications when co-formulated with μ-opioid analgesics. In a double-blind ascending dose study, four subjects on methadone maintenance received 6β-naltrexol (0.05, 0.15, 0.50 and 1.0 mg). 6β-Naltrexol was generally well tolerated; three of four subjects reported willingness to take higher doses. Increased gastrointestinal activity was evidenced by decreased oral-cecal transit time and prompt laxation at higher doses.

The aims of this first-in-human study were to examine the pharmacokinetics of 6β-naltrexol to measure two key characteristics of 6β-naltrexol in highly opioid dependent persons: unwanted aspects of opioid antagonism such as withdrawal, and preferential suppression of opioid effects on the gastrointestinal tract compared to the central nervous system. Eight subjects were enrolled. Of these subjects, four were ineligible for dosing with 6β-naltrexol: three due to small bowel bacterial overgrowth and one due to difficulty with IV catheter insertion. Clinical characteristics of the four subjects who received 6β-naltrexol are presented in Table 8A below. One subject met stopping criteria after receiving the 0.5 mg 6β-naltrexol dose, and did not receive either the 1.0 mg dose or placebo. Another subject experienced distress at the 1.0 mg dose, reporting a 10 on the 10 point pain scale and did not provide self-report data between 15 min and 6 hours after dosing. The remaining two subjects tolerated the 1.0 mg dose and reported a willingness to take higher doses of 6β-naltrexol.

Withdrawal Symptoms Overall withdrawal was minimal as indicated by the visual analog scale (VAS) scores, and totals on the Subjective Opiate Withdrawal Scale (SOWS), Objective Opiate Withdrawal Scale (OOWS), and vital signs data (see Table 8B). There was a main effect of dose on the "Any Drug Effect" VAS item ($F_{4,13}$=7.078, p=0.003) and total OOWS ($F_{4,13}$=4.340, p=0.027). "Any Drug Effect" was significantly higher for the 0.5 mg and 1.0 mg 6βNTX doses than placebo (p<0.001, and p<0.05 respectively). Total OOWS was significantly higher for the 1.0 mg 6βNTX dose than placebo (p<0.01). OOWS items reported varied widely, with all individuals reporting abdominal cramps at the 0.5 mg and 1.0 mg doses. There was no effect of dose on any other measure. Overall, the observed withdrawal symptoms were considered to reflect peripheral but not CNS-related opioid withdrawal.

Gastrointestinal Effects Laxation was experienced for one subject (25%; 101 minutes post dose) at the 0.05 mg dose, three subjects (75%; 2, 17, and 40 minutes post dose) at the 0.5 mg dose, and two subjects (67%; both at 5 minutes post dose) at the 1.0 mg dose. One subject who did not experience laxation at any dose was determined to have small bowel bacterial overgrowth during the naloxone challenge, and did not participate in further oral-cecal transit time testing. The subject who met stopping criteria at 0.5 mg did not receive placebo so his transit time data were not evaluable. In the two subjects who did undergo oral-cecal transit time testing (lactulose/H2 test), 6β-naltrexol accelerated GI transit time at doses of 0.25 mg and above. A quantitative evaluation of this test was not possible because of insufficient number of subjects (data from only two subjects were evaluable, while a third subject had elevated base-line H2 levels, and a fourth subject was not tested), but a detectable reversal of GI slowing at 0.25 mf 6β-naltrexol is consistent with the finding that regulator bowel movement occurred with two subjects at 0.5 mg 6β-naltrexol.

Pharmacokinetics Pharmacokinetic profiles of serum 6β-naltrexol were obtained from two subjects at the 1.0 mg dose (Subject 1: $C_{max}$=3.8 ng/mL, $t_{1/2}$=2.2 hours, AUC=7.8 ng/mL*hour, CL=128 L/hr; Subject 2: $C_{max}$=3.2 ng/mL, $t_{1/2}$=2.43 hours, AUC=7.6 ng/mL*hour, CL=131 L/hr). Using an assay with a lower limit of quantification of 0.5 ng/mL, 6β-naltrexol was detectable in plasma for only six hours. Determination of terminal half-life of elimination was not feasible because of lack of sufficient assay sensitivity.

Conclusions. This first-in-human study of the effects of the neutral opioid antagonist 6β-naltrexol in opioid dependent subjects showing that at all but the highest dose (1.0 mg), 6β-naltrexol was well tolerated by this highly opioid dependent sample population. Withdrawal symptoms were judged to be largely related to peripheral opioid effects, indicating a high degree of peripheral selectivity of 6β-naltrexol, consistent with animal research suggesting that 6β-naltrexol causes substantially less opioid withdrawal than inverse agonists like naloxone, and displays peripheral selectivity. In contrast, naloxone causes substantial peripheral and CNS-related withdrawal at doses of 0.4 mg.

In contrast to 6β-naltrexol effects in opioid naïve subjects tested described earlier, opioid dependent subjects are substantially more sensitive to opioid antagonists in general, including neutral antagonists, apparently because a smaller degree of displacement of morphine from its receptor is needed for full effects. A 6β-naltrexol dose of 0.5 mg iv appears to be sufficient initially to cause laxation in methadone maintenance patients, demonstrating high potency while lacking serious withdrawal symptoms. Considering an opioid analgesic/antagonist oral co-formulation, this is optimally designed for opioid-naïve subjects, while opioid-dependent subjects require first administration of lower 6β-naltrexol doses for several days until the fully effective combination dose can be taken.

Tables 8A and 8B show the results from a preliminary eIND experiments in 4 methadone-dependent subjects. In two subjects the 0.5 mg 6β-naltrexol led to an immediate bowel movement obviously related to the drug dose. One subject was more sensitive to 6β-naltrexol and would not have tolerated a dose above 1 mg 6β-naltrexol i.v. Pupillometry measures (a CNS effect) were unaffected by up to 1 mg 6β-naltrexol (not shown), supporting the conclusion that 6β-naltrexol had no significant CNS effects at that dose.

TABLE 8A

Clinical characteristics of the four patients.

| | Age (Years) | Race | Daily methadone dose (mg) | Time at current methadone dose (days) | Highest 6β-naltrexol Dose (mg) | GI Transit Testing | Lowest dose producing laxation (mg) | Would continue after highest dose |
|---|---|---|---|---|---|---|---|---|
| Female | 27 | African-American | 70 | 14 | 1.0 | Yes | 0.05 | Yes |
| Female | 45 | African-American | 19 | 180 | 1.0 | Yes | 0.5 | No |
| Female | 44 | Caucasian | 40 | 90 | 1.0 | No | NA | Yes |
| Male | 46 | African-American | 40 | 30 | 0.5 | Yes | 0.5 | Yes |

TABLE 8B

Peak Values on Withdrawal Scales, visual analog scale (VAS) items, and vital signs

| | Naloxone | 6β-naltrexol | | | | |
|---|---|---|---|---|---|---|
| Dose | 0.05 mg | 0.0 mg | 0.05 mg | 0.15 mg | 0.5 mg | 1.0 mg |
| Withdrawal Scales | | | | | | |
| OOWS (total) | 2.5 ± 0.6 | 0.7 ± 0.6 | 0.8 ± 0.5 | 1.5 ± 0.6 | 3.5 ± 1.3 | 5.3 ± 4.0* |
| SOWS (total) | 3.0 ± 2.8 | 1.3 ± 1.5 | 0.8 ± 1.0 | 1.3 ± 1.9 | 4.3 ± 2.2 | 4.3 ± 2.8 |
| VAS | | | | | | |
| Any Drug Effect | 15.4 ± 23.7 | 2.0 ± 1.7 | 0.5 ± 1.0 | 1.5 ± 1.7 | 34.3 ± 15.7* | 24.0 ± 21.7* |
| Bad Drug Effect | 13.5 ± 25.0 | 1.3 ± 1.2 | 0.8 ± 1.5 | 17.9 ± 32.5 | 42.5 ± 23.7 | 26.9 ± 33.0 |
| Good Drug Effect | 10.4 ± 18.9 | 1.3 ± 1.2 | 0.3 ± 0.5 | 2.2 ± 2.8 | 6.5 ± 12.3 | 1.0 ± 0.0 |
| Opioid Withdrawal | 5.6 ± 8.2 | 1.7 ± 1.5 | 1.3 ± 2.5 | 1.4 ± 1.3 | 21.0 ± 29.7 | 13.1 ± 8.1 |
| Sickness | 4.6 ± 6.5 | 0.7 ± 0.6 | 0.50 ± 1.00 | 9.3 ± 17.2 | 15.8 ± 18.1 | 9.0 ± 5.6 |

TABLE 8B-continued

Peak Values on Withdrawal Scales, visual analog scale (VAS) items, and vital signs

| | Naloxone | 6β-naltrexol | | | | |
|---|---|---|---|---|---|---|
| Dose | 0.05 mg | 0.0 mg | 0.05 mg | 0.15 mg | 0.5 mg | 1.0 mg |
| Vital Signs | | | | | | |
| Systolic blood pressure (BP) (mmHg) | 114.0 ± 1.8 | 121.7 ± 2.9 | 121.3 ± 7.0 | 118.5 ± 10.0 | 118.8 ± 7.6 | 134.7 ± 26.4 |
| Diastolic BP (mmHg) | 76.5 ± 3.8 | 83.7 ± 4.9 | 83.0 ± 5.9 | 76.5 ± 5.1 | 80.3 ± 5.7 | 88.3 ± 12.7 |
| Heart Rate (bpm) | 63.5 ± 8.0 | 65.0 ± 4.4 | 61.8 ± 6.2 | 59.5 ± 2.9 | 61.8 ± 5.7 | 71.7 ± 4.9 | mean ± standard deviation;
*p < .05 vs. placebo
OOWS is the objective opiate withdrawal scale
SOWS is the subjective opiate withdrawal scale
(For OOWS and SOWS, see (see, e.g., Handelsman et al. (1987) Two New Rating Scales for Opiate Withdrawal. American Journal of Alcohol Abuse, 13, 293-308).

The published patents, patent applications, websites, company names, and scientific literature referred to herein establish the knowledge that is available to those with skill in the art and are hereby incorporated by reference in their entirety to the same extent as if each was specifically and individually indicated to be incorporated by reference. Any conflict between any reference cited herein and the specific teachings of this specification shall be resolved in favor of the latter.

While this invention has been particularly shown and described with references to preferred embodiments thereof, it will be understood by those skilled in the art that various changes in form and details may be made therein without departing from the scope of the invention encompassed by the appended claims.

The invention claimed is:

1. A method of providing an opioid agonist to a mammalian subject in a manner that inhibits peripheral effects of the opioid agonist, without blocking substantial central effects, the method comprising:
    orally administering to the subject at least one unit dosage of an analgesic composition, formulated for oral administration, the unit dosage including:
    (a) the opioid agonist in an amount sufficient to confer analgesia in the subject;
    (b) a non-aversive neutral opioid antagonist in an amount sufficient to substantially inhibit peripheral effects and insufficient to block substantial central effects of the agonist in the subject, the opioid antagonist selected to have an access to a central nervous system of the subject that is weak compared to access by the opioid agonist;
    wherein the amounts of the neutral opioid antagonist and the opioid agonist are selected so that a weight/weight (w/w) ratio of (1) an amount of 6β-naltrexol equivalent to the amount of neutral opioid antagonist divided by (2) an amount of morphine equivalent to the opioid agonist is at least 0.15; and
    (c) a pharmaceutically acceptable carrier.

2. The method of claim 1, wherein oral bioavailability to circulation of the subject of at least about 25%.

3. The method of claim 1, the mammalian subject is a human.

4. The method of claim 1, wherein the opioid agonist is morphine.

5. The method of claim 1, wherein the opioid agonist is not morphine.

6. The method of claim 1, wherein the blood half-life of the non-aversive neutral opioid antagonist is at least 2-fold longer than the blood half-life of the opioid agonist.

7. The method of claim 1, wherein the opioid agonist is selected from the group consisting of alfentanil, allylprodine, alphaprodine, anileridine, benzylmorphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, fentanyl, heroin, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, narceine, nicomorphine, norlevorphanol, normethadone, noroxycodone, nalorphine, nalbuphene, normorphine, norpipanone, opium, oxycodone, oxymorphone, papaveretum, pentazocine, phenadoxone, phenomorphan, phenazocine, phenoperidine, piminodine, piritramide, propheptazine, promedol, properidine, propoxyphene, sufentanil, tilidine, and tramadol.

8. The method of claim 1, wherein the non-aversive neutral opioid antagonist is a naltrexone analog represented by formula Iα or Iβ:

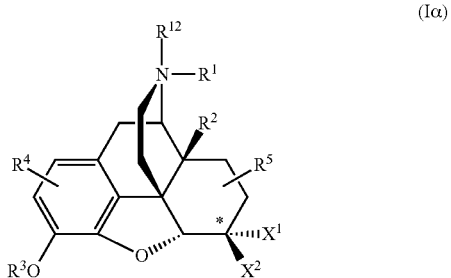

(Iα)

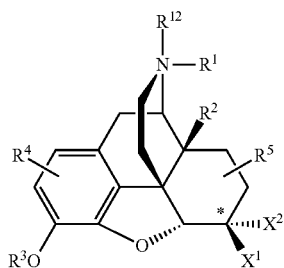

(Iβ)

wherein:
- $R^1$ is $C_3$-$C_6$ (cycloalkyl)(alkyl) or $C_5$-$C_7$ (cycloalkenyl) alkyl;
- $R^2$ is H, OH or esters thereof;
- $R^3$ is H, alkyl or $C_1$-$C_6$ alkyl-C=O;
- $R^4$ and $R^5$ are independently H, halogen, $C_1$-$C_6$ alkyl, $C_1$-$C_4$ alkoxy, nitro, amino, cyano, carboxyl or acyl which may be substituted for one or more hydrogens on the ring;
- $X^1$ and $X^2$ are the same or different, and may be H, alkyl, —$OR_6$, —$NR^7R^8R^9$, —$NCOR^{10}$, —$NO_2$, or —$SR^{11}$;
- $R^6$ and $R^{11}$ are independently H, alkyl, substituted alkyl, cycloalkyl, substituted cycloalkyl, aryl, substituted aryl, acyl, aroyl, polyethyleneglycyl (PEGyl) or a polyether group;
- $R^7$, $R^8$ and $R^{10}$ are independently hydrogen, alkyl, substituted alkyl, cycloalkyl, substituted cycloalkyl, aryl, or substituted aryl;
- $R^9$ can be present or absent and is independently hydrogen, alkyl, substituted alkyl, cycloalkyl, substituted cycloalkyl, aryl, or substituted aryl;
- $R^{12}$ is hydrogen; or pharmaceutically acceptable salts thereof.

9. The method of claim 1, wherein the non-aversive neutral opioid antagonist is a naloxone analog represented by formula Iα or Iβ:

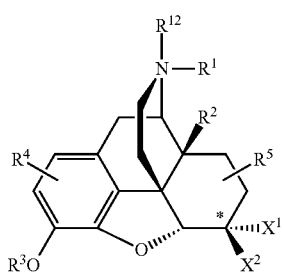

(Iα)

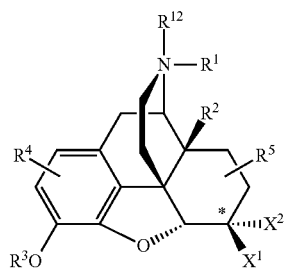

(Iβ)

wherein:
- $R^1$ is $C_3$-$C_6$ alkenyl;
- $R^2$ is H, OH or esters thereof;
- $R^3$ is H, alkyl or $C_1$-$C_6$ alkyl-C=O;
- $R^4$ and $R^5$ are independently H, halogen, $C_1$-$C_6$ alkyl, $C_1$-$C_4$ alkoxy, nitro, amino, cyano, carboxyl or acyl which may be substituted for one or more hydrogens on the ring;
- $X^1$ and $X^2$ are the same or different, and may be H, alkyl, —$OR_6$, —$NR^7R^8R^9$, —$NCOR^{10}$, —$NO_2$, or —$SR^{11}$;
- $R^6$ and $R^{11}$ are independently H, alkyl, substituted alkyl, cycloalkyl, substituted cycloalkyl, aryl, substituted aryl, acyl, aroyl, polyethyleneglycyl (PEGyl) or a polyether group;
- $R^7$, $R^8$ and $R^{10}$ are independently hydrogen, alkyl, substituted alkyl, cycloalkyl, substituted cycloalkyl, aryl, or substituted aryl;
- $R^9$ can be present or absent and is independently hydrogen, alkyl, substituted alkyl, cycloalkyl, substituted cycloalkyl, aryl, or substituted aryl;
- $R^{12}$ is hydrogen; or pharmaceutically acceptable salts thereof.

10. The method of claim 1, wherein the non-aversive neutral opioid antagonist is selected from the group consisting of 6β-naltrexol, 6β-naltrexamide, 6β-naloxol, 6α-naltrexol, 6α-naloxol, 6α-naltrexamine, 6β-naltrexamine, 6-deoxynaltrexone, and 6α-naltrexamide, pharmaceutically acceptable physical isomorphs thereof, and pharmaceutically acceptable salts thereof.

11. The method of claim 1, wherein the non-aversive neutral opioid antagonist is 6β-naltrexol.

12. The method of claim 1, wherein the non-aversive neutral opioid antagonist is 6β-naltrexamine.

13. The method of claim 1, wherein the non-aversive neutral opioid antagonist is not 6β-naltrexol.

14. The method of claim 1, wherein the unit dosage is in a slow-release formulation.

* * * * *